(12) United States Patent
Berthon-Jones et al.

(10) Patent No.: US 11,666,725 B2
(45) Date of Patent: Jun. 6, 2023

(54) MASK AND COMPONENTS THEREOF

(71) Applicant: ResMed Pty Ltd, Bella Vista (AU)

(72) Inventors: Michael Berthon-Jones, Sydney (AU); Michael Kassipillai Gunaratnam, Sydney (AU); Richard Sokolov, Sydney (AU); Robin Garth Hitchcock, Sydney (AU); David John Bassin, Sydney (AU); Gordon Joseph Malouf, Sydney (AU); Peter Edward Bateman, Sydney (AU); Philip Rodney Kwok, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/873,545

(22) Filed: Jul. 26, 2022

(65) Prior Publication Data
US 2022/0355058 A1 Nov. 10, 2022

Related U.S. Application Data

(63) Continuation of application No. 17/131,973, filed on Dec. 23, 2020, now Pat. No. 11,406,784, which is a
(Continued)

(51) Int. Cl.
*A61M 16/06* (2006.01)
*A61M 16/00* (2006.01)
(Continued)

(52) U.S. Cl.
CPC .... *A61M 16/0683* (2013.01); *A61M 16/0003* (2014.02); *A61M 16/0051* (2013.01);
(Continued)

(58) Field of Classification Search
CPC .......... A61M 16/0616; A61M 16/0605; A61M 16/0622; A61M 16/06
See application file for complete search history.

(56) References Cited

U.S. PATENT DOCUMENTS

| 443,191 A | 12/1890 | Illing |
|---|---|---|
| 781,516 A | 1/1905 | Guthrie, Jr. |

(Continued)

FOREIGN PATENT DOCUMENTS

| AU | 199651130 | 10/1996 |
|---|---|---|
| AU | 2005100738 | 11/2005 |

(Continued)

OTHER PUBLICATIONS

Office Action dated Mar. 2, 2016 issued in U.S. Appl. No. 12/461,448 (25 pages).
(Continued)

*Primary Examiner* — Timothy A Stanis
(74) *Attorney, Agent, or Firm* — Nixon & Vanderhye P.C.

(57) ABSTRACT

A patient interface includes a shell with a central opening configured to receive the pressurized flow of air, a foam cushion, and an elastomeric support portion that is attached to the shell, supports the foam cushion, and forms at least part of a chamber together with the shell and the foam cushion. The elastomeric support portion includes a side wall that forms a continuous perimeter around the chamber and a resiliently flexible lip that supports the foam cushion and extends from the side wall toward an interior of the chamber. The resiliently flexible lip has an outer perimeter that is anchored to the side wall and an unsupported inner perimeter. The foam cushion overhangs the inner perimeter of the resiliently flexible lip, and the shell is more rigid than the elastomeric support portion. In addition, the foam cushion is configured to directly contact and engage a portion of the patient's skin in use.

23 Claims, 92 Drawing Sheets

Related U.S. Application Data continuation of application No. 14/471,525, filed on Aug. 28, 2014, now Pat. No. 10,940,283, which is a continuation of application No. 12/461,448, filed on Aug. 12, 2009, now Pat. No. 10,307,554, which is a continuation of application No. 10/533,928, filed as application No. PCT/AU03/01471 on Nov. 6, 2003, now Pat. No. 8,490,623.

(60) Provisional application No. 60/503,896, filed on Sep. 22, 2003, provisional application No. 60/488,752, filed on Jul. 22, 2003, provisional application No. 60/447,327, filed on Feb. 14, 2003, provisional application No. 60/424,005, filed on Nov. 6, 2002.

(51) Int. Cl.
*A61M 16/08* (2006.01)
*A61M 16/20* (2006.01)

(52) U.S. Cl.
CPC ...... *A61M 16/0057* (2013.01); *A61M 16/022* (2017.08); *A61M 16/06* (2013.01); *A61M 16/0605* (2014.02); *A61M 16/0616* (2014.02); *A61M 16/0622* (2014.02); *A61M 16/0633* (2014.02); *A61M 16/0875* (2013.01); *A61M 16/0825* (2014.02); *A61M 16/20* (2013.01); *A61M 2016/0027* (2013.01); *A61M 2016/0661* (2013.01); *A61M 2205/0266* (2013.01); *A61M 2205/10* (2013.01); *A61M 2205/15* (2013.01); *A61M 2205/3344* (2013.01)

(56) References Cited

U.S. PATENT DOCUMENTS

| | | |
|---|---|---|
| 1,081,745 A | 12/1913 | Johnston |
| 1,125,542 A | 1/1915 | Humphries |
| 1,192,186 A | 7/1916 | Greene |
| 1,229,050 A | 6/1917 | Donald |
| 1,282,527 A | 10/1918 | Bidonde |
| 1,362,766 A | 12/1920 | McGargill |
| 1,445,010 A | 2/1923 | Feinberg |
| 1,610,793 A | 12/1926 | Kaufman |
| 1,873,160 A | 8/1932 | Sturtevant |
| 2,353,643 A | 7/1944 | Bulbulian |
| 2,415,846 A | 2/1947 | Randall |
| 2,433,565 A | 12/1947 | Korman |
| 2,625,155 A | 1/1953 | Engelder |
| 2,706,983 A | 4/1955 | Matheson et al. |
| 2,931,356 A | 4/1960 | Schwarz |
| 3,013,556 A | 12/1961 | Galleher |
| 3,330,273 A | 7/1967 | Bennett |
| 3,556,097 A | 1/1971 | Wallace |
| 3,670,726 A | 3/1972 | Mahon et al. |
| 3,682,171 A | 8/1972 | Dali et al. |
| 3,739,774 A | 6/1973 | Gregory |
| 3,754,552 A | 8/1973 | King |
| 3,815,596 A | 6/1974 | Keener |
| 3,844,286 A | 10/1974 | Cowen |
| 3,861,385 A | 1/1975 | Carden |
| 3,901,228 A | 8/1975 | Brown |
| 3,902,486 A | 9/1975 | Guichard |
| 3,905,361 A | 9/1975 | Hewson et al. |
| 3,938,614 A | 2/1976 | Ahs |
| 3,972,321 A | 8/1976 | Proctor |
| 4,006,744 A | 2/1977 | Steer |
| 4,142,527 A | 3/1979 | Garcia |
| 4,153,051 A | 5/1979 | Shippert |
| 4,156,426 A | 5/1979 | Gold |
| 4,248,218 A | 2/1981 | Fischer |
| 4,263,908 A | 4/1981 | Mizerak |
| 4,264,743 A | 4/1981 | Maruyama et al. |
| 4,267,845 A | 5/1981 | Robertson, Jr. et al. |
| 4,273,124 A | 6/1981 | Zimmerman |
| 4,312,359 A | 1/1982 | Olson |
| 4,367,735 A | 1/1983 | Dali |
| 4,367,816 A | 1/1983 | Wilkes |
| 4,406,283 A | 9/1983 | Bir |
| 4,414,973 A | 11/1983 | Matheson et al. |
| 4,422,456 A | 12/1983 | Teip |
| 4,449,526 A | 5/1984 | Elam |
| 4,455,675 A | 6/1984 | Bose et al. |
| 4,493,614 A | 1/1985 | Chu et al. |
| 4,548,200 A | 10/1985 | Wapner |
| 4,549,542 A | 11/1985 | Chein |
| 4,572,323 A | 2/1986 | Randall |
| 4,587,967 A | 5/1986 | Chu et al. |
| 4,601,465 A | 7/1986 | Roy |
| 4,617,637 A | 11/1986 | Chu et al. |
| 4,630,604 A | 12/1986 | Montesi |
| 4,641,647 A | 2/1987 | Behan |
| 4,660,555 A | 4/1987 | Payton |
| 4,671,271 A | 6/1987 | Bishop et al. |
| 4,676,241 A | 6/1987 | Webb et al. |
| 4,699,139 A | 10/1987 | Marshall et al. |
| 4,706,664 A | 11/1987 | Snook et al. |
| 4,711,636 A | 12/1987 | Bierman |
| 4,713,844 A | 12/1987 | Westgate |
| D293,613 S | 1/1988 | Wingler |
| 4,739,755 A * | 4/1988 | White ................ A61M 16/0611 128/206.12 |
| 4,753,233 A | 6/1988 | Grimes |
| 4,767,411 A | 8/1988 | Edmunds |
| 4,770,169 A * | 9/1988 | Schmoegner ......... A61M 16/08 128/206.28 |
| 4,774,946 A | 11/1988 | Ackerman et al. |
| 4,782,832 A | 11/1988 | Trimble et al. |
| 4,790,829 A | 12/1988 | Bowden et al. |
| 4,802,857 A | 2/1989 | Laughlin |
| 4,803,981 A | 2/1989 | Vickery |
| 4,811,730 A | 3/1989 | Milano |
| 4,830,138 A | 5/1989 | Palmaer et al. |
| 4,838,878 A | 6/1989 | Kalt et al. |
| 4,899,740 A | 2/1990 | Napolitano |
| 4,907,584 A | 3/1990 | McGinnis |
| 4,915,105 A | 4/1990 | Lee |
| 4,919,128 A | 4/1990 | Kopala et al. |
| 4,919,654 A | 4/1990 | Kalt |
| 4,944,310 A | 7/1990 | Sullivan |
| 4,945,907 A | 8/1990 | Tayebi |
| 4,960,121 A | 10/1990 | Nelson |
| 4,969,880 A | 11/1990 | Zamierowski |
| 4,971,051 A | 11/1990 | Toffolon |
| 4,976,698 A | 12/1990 | Stokley |
| 4,989,599 A | 2/1991 | Carter |
| 4,996,983 A | 3/1991 | Amrhein |
| 5,000,173 A | 3/1991 | Zalkin et al. |
| 5,005,571 A | 4/1991 | Dietz |
| 5,020,163 A | 6/1991 | Aileo et al. |
| 5,022,900 A | 6/1991 | Bar-Yona et al. |
| 5,023,955 A | 6/1991 | Murphy, II et al. |
| 5,025,805 A | 6/1991 | Nutter |
| 5,038,772 A | 8/1991 | Kolbe et al. |
| 5,042,478 A | 8/1991 | Kopala et al. |
| 5,046,491 A | 9/1991 | Derrick |
| 5,074,297 A | 12/1991 | Venegas |
| 5,113,857 A | 5/1992 | Dickerman et al. |
| 5,117,818 A | 6/1992 | Palfy |
| 5,121,745 A | 6/1992 | Israel |
| 5,127,397 A | 7/1992 | Kohnke |
| 5,137,017 A | 8/1992 | Salter |
| 5,138,722 A | 8/1992 | Urella et al. |
| D333,015 S | 2/1993 | Farmer et al. |
| 5,188,101 A | 2/1993 | Tumolo |
| 5,207,665 A | 5/1993 | Davis et al. |
| 5,220,699 A | 6/1993 | Farris |
| 5,243,709 A | 9/1993 | Sheehan et al. |
| 5,243,971 A | 9/1993 | Sullivan |
| 5,245,995 A | 9/1993 | Sullivan et al. |
| 5,261,893 A | 11/1993 | Zamierowski |
| 5,263,939 A | 11/1993 | Wortrich |
| 5,265,592 A | 11/1993 | Beaussant |
| 5,265,595 A | 11/1993 | Rudolph |

(56) References Cited

U.S. PATENT DOCUMENTS

| | | |
|---|---|---|
| 5,267,557 A | 12/1993 | Her-Mou |
| 5,269,296 A | 12/1993 | Landis |
| 5,271,391 A | 12/1993 | Graves |
| 5,304,146 A | 4/1994 | Johnson et al. |
| 5,299,599 A | 5/1994 | Farmer et al. |
| 5,335,656 A | 8/1994 | Bowe et al. |
| 5,349,949 A | 9/1994 | Schegerin |
| 5,355,878 A | 10/1994 | Griffiths et al. |
| 5,355,893 A | 10/1994 | Mick et al. |
| 5,364,367 A | 11/1994 | Banks et al. |
| 5,372,130 A | 12/1994 | Stem et al. |
| 5,372,388 A | 12/1994 | Gargiulo |
| 5,372,389 A | 12/1994 | Tam et al. |
| 5,372,390 A | 12/1994 | Conway et al. |
| 5,372,391 A | 12/1994 | Bast et al. |
| 5,375,593 A | 12/1994 | Press |
| 5,385,141 A | 1/1995 | Granatiero |
| 5,394,568 A | 3/1995 | Brostrom et al. |
| 5,396,885 A | 3/1995 | Nelson |
| 5,398,676 A | 3/1995 | Press et al. |
| 5,400,776 A | 3/1995 | Bartholomew |
| 5,419,318 A | 5/1995 | Tayebi |
| 5,425,359 A | 6/1995 | Liou |
| 5,429,683 A | 7/1995 | Le Mitouard |
| 5,437,267 A | 8/1995 | Weinstein et al. |
| 5,441,046 A | 8/1995 | Starr et al. |
| 5,462,528 A | 10/1995 | Roewer |
| 5,477,852 A | 12/1995 | Landis et al. |
| 5,526,806 A | 1/1996 | Sansoni |
| 5,488,948 A | 2/1996 | Dubruille et al. |
| 5,509,409 A | 4/1996 | Weatherholt |
| 5,513,634 A | 5/1996 | Jackson |
| 5,513,635 A | 5/1996 | Bedi |
| 5,533,506 A | 7/1996 | Wood |
| 5,538,000 A | 7/1996 | Rudolph |
| 5,538,001 A | 7/1996 | Bridges |
| 5,560,354 A | 10/1996 | Berthon-Jones et al. |
| 5,570,684 A | 11/1996 | Behr |
| 5,592,938 A | 1/1997 | Scarberry et al. |
| 5,623,923 A | 4/1997 | Bertheau et al. |
| 5,647,357 A | 7/1997 | Barnett et al. |
| 5,653,228 A | 8/1997 | Byrd |
| 5,655,527 A | 8/1997 | Scarberry et al. |
| 5,660,174 A | 8/1997 | Jacobelli |
| 5,662,101 A | 9/1997 | Ogden et al. |
| 5,682,881 A | 11/1997 | Winthrop et al. |
| 5,704,345 A | 1/1998 | Berthon-Jones et al. |
| 5,707,342 A | 1/1998 | Tanaka |
| 5,724,965 A | 3/1998 | Handke et al. |
| 5,735,272 A | 4/1998 | Dillon et al. |
| 5,740,799 A | 4/1998 | Nielson |
| 5,752,511 A | 5/1998 | Simmons et al. |
| 5,794,619 A | 8/1998 | Edeiman et al. |
| 5,807,341 A | 9/1998 | Heim |
| 5,842,469 A | 12/1998 | Rapp et al. |
| 5,906,203 A | 5/1999 | Klockseth et al. |
| 5,918,598 A | 7/1999 | Belfer et al. |
| 5,921,239 A | 7/1999 | McCall et al. |
| 5,954,049 A | 9/1999 | Foley et al. |
| 5,975,079 A | 11/1999 | Hellings et al. |
| 6,019,101 A | 1/2000 | Cotner et al. |
| 6,026,811 A | 2/2000 | Settle |
| 6,039,737 A | 3/2000 | Dyer |
| 6,044,844 A | 4/2000 | Kwok et al. |
| 6,082,360 A | 7/2000 | Rudolph et al. |
| 6,086,118 A | 7/2000 | McNaughton et al. |
| 6,095,996 A | 8/2000 | Steer et al. |
| 6,098,205 A | 8/2000 | Schwartz et al. |
| 6,109,263 A | 8/2000 | Feuchtgruber |
| 6,112,746 A | 9/2000 | Kwok et al. |
| 6,119,693 A | 9/2000 | Kwok et al. |
| 6,119,694 A | 9/2000 | Correa et al. |
| 6,123,071 A | 9/2000 | Berthon-Jones et al. |
| 6,123,082 A | 9/2000 | Berthon-Jones |
| 6,139,787 A | 10/2000 | Harrison |
| 6,152,137 A | 11/2000 | Schwartz et al. |
| 6,193,914 B1 | 2/2001 | Harrison |
| 6,196,223 B1 | 3/2001 | Belfer et al. |
| 6,211,263 B1 | 4/2001 | Cinelli et al. |
| 6,231,548 B1 | 5/2001 | Bassett |
| 6,241,930 B1 | 6/2001 | Harrison |
| 6,258,066 B1 | 7/2001 | Urich |
| 6,295,366 B1 | 9/2001 | Haller et al. |
| 6,328,038 B1 | 12/2001 | Kessler et al. |
| 6,341,606 B1 | 1/2002 | Bordewick et al. |
| 6,347,631 B1 | 2/2002 | Hansen et al. |
| 6,357,441 B1 | 3/2002 | Kwok et al. |
| 6,358,279 B1 | 3/2002 | Tahi et al. |
| 6,374,826 B1 | 4/2002 | Gunaratnam et al. |
| 6,412,487 B1 | 7/2002 | Gunaratnam et al. |
| 6,412,488 B1 | 7/2002 | Barnett et al. |
| 6,412,593 B1 | 7/2002 | Jones |
| 6,419,660 B1 | 7/2002 | Russo |
| 6,422,238 B1 | 7/2002 | Lithgow |
| 6,423,036 B1 | 7/2002 | Van Huizen |
| 6,431,172 B1 | 8/2002 | Bordewick |
| 6,434,796 B1 | 8/2002 | Speirs |
| 6,439,234 B1 | 8/2002 | Curti et al. |
| 6,448,303 B1 | 9/2002 | Paul |
| 6,467,482 B1 | 10/2002 | Boussignac |
| 6,467,483 B1 | 10/2002 | Kopacko et al. |
| 6,470,886 B1 | 10/2002 | Jestrabek-Hart |
| 6,470,887 B1 | 10/2002 | Martinez |
| 6,478,026 B1 | 11/2002 | Wood |
| 6,482,178 B1 | 11/2002 | Andrews et al. |
| 6,491,034 B1 | 12/2002 | Gunaratnam et al. |
| 6,513,526 B2 | 2/2003 | Kwok et al. |
| 6,530,373 B1 | 3/2003 | Patron et al. |
| 6,532,961 B1 | 3/2003 | Kwok et al. |
| 6,536,435 B1 | 3/2003 | Fecteau |
| 6,561,188 B1 | 5/2003 | Ellis |
| 6,561,190 B1 | 5/2003 | Kwok et al. |
| 6,561,192 B2 | 5/2003 | Palmer |
| 6,561,193 B1 | 5/2003 | Noble |
| 6,571,798 B1 | 6/2003 | Thornton |
| 6,579,267 B2 | 6/2003 | Lynch et al. |
| 6,581,601 B2 | 6/2003 | Ziaee |
| 6,581,602 B2 | 6/2003 | Kwok et al. |
| 6,584,975 B1 | 7/2003 | Taylor |
| 6,595,214 B1 | 7/2003 | Hecker et al. |
| 6,595,215 B2 | 7/2003 | Wood |
| 6,607,516 B2 | 8/2003 | Cinelli et al. |
| 6,627,289 B1 | 9/2003 | Dilnik et al. |
| 6,631,718 B1 | 10/2003 | Lovell |
| 6,634,358 B2 | 10/2003 | Kwok et al. |
| 6,637,434 B2 | 10/2003 | Noble |
| 6,644,315 B2 | 11/2003 | Ziaee |
| 6,655,385 B1 | 12/2003 | Curti et al. |
| 6,663,600 B2 | 12/2003 | Bierman et al. |
| 6,669,712 B1 | 12/2003 | Cardoso |
| D485,905 S | 1/2004 | Moore et al. |
| 6,679,257 B1 | 1/2004 | Robertson et al. |
| 6,679,265 B2 | 1/2004 | Strickland et al. |
| 6,684,882 B1 | 2/2004 | Morine |
| 6,701,927 B2 | 3/2004 | Kwok et al. |
| 6,710,099 B2 | 3/2004 | Cinelli et al. |
| 6,766,800 B2 | 7/2004 | Chu et al. |
| 6,766,817 B2 | 7/2004 | da Silva |
| 6,776,162 B2 | 8/2004 | Wood |
| 6,776,163 B2 | 8/2004 | Dougill et al. |
| 6,789,543 B2 | 9/2004 | Cannon |
| 6,805,117 B1 | 10/2004 | Ho |
| 6,807,967 B2 | 10/2004 | Wood |
| 6,817,362 B2 | 11/2004 | Gelinas et al. |
| 6,820,617 B2 | 11/2004 | Robertson et al. |
| 6,823,865 B2 | 11/2004 | Drew et al. |
| 6,823,869 B2 | 11/2004 | Raje et al. |
| 6,834,650 B1 | 12/2004 | Fini |
| 6,860,270 B2 | 3/2005 | Sniadach |
| 6,886,183 B2 | 5/2005 | Dehaan |
| 6,895,965 B2 | 5/2005 | Scarberry et al. |
| 6,907,882 B2 | 6/2005 | Ging et al. |
| 6,918,404 B2 | 7/2005 | Dias da Silva |
| 6,926,004 B2 | 8/2005 | Schumacher |

(56) References Cited

U.S. PATENT DOCUMENTS

| | | |
|---|---|---|
| 6,932,089 B1 | 8/2005 | Cinquin |
| 6,938,620 B2 | 9/2005 | Payne, Jr. |
| 6,968,844 B2 | 11/2005 | Liland |
| 6,972,003 B2 | 12/2005 | Bierman et al. |
| 6,986,352 B2 | 1/2006 | Frater et al. |
| 6,997,177 B2 | 2/2006 | Wood |
| 7,011,090 B2 | 3/2006 | Drew et al. |
| 7,018,362 B2 | 3/2006 | Bierman et al. |
| 7,052,127 B2 | 5/2006 | Harrison |
| 7,066,586 B2 | 6/2006 | da Silva |
| 7,076,282 B2 | 7/2006 | Munro et al. |
| 7,080,645 B2 | 7/2006 | Genger et al. |
| 7,101,359 B2 | 9/2006 | Kline et al. |
| 7,107,989 B2 | 9/2006 | Frater et al. |
| 7,146,976 B2 | 12/2006 | McKown |
| 7,152,599 B2 | 12/2006 | Thomas |
| 7,152,601 B2 | 12/2006 | Barakat et al. |
| 7,178,525 B2 | 2/2007 | Matula, Jr. et al. |
| 7,191,781 B2 | 3/2007 | Wood |
| 7,207,328 B1 | 4/2007 | Altemus |
| 7,210,481 B1 | 5/2007 | Lovell et al. |
| 7,237,551 B2 | 7/2007 | Ho et al. |
| 7,243,723 B2 | 7/2007 | Surjaatmadja |
| D550,836 S | 9/2007 | Chandran et al. |
| D552,733 S | 10/2007 | Criscuolo et al. |
| 7,285,255 B2 | 10/2007 | Kadlec et al. |
| 7,302,950 B2 | 12/2007 | Berthon-Jones et al. |
| 7,318,437 B2 | 1/2008 | Gunaratnam et al. |
| 7,523,754 B2 | 4/2009 | Lithgow |
| 7,658,189 B2 | 2/2010 | Davidson |
| 8,490,623 B2 | 7/2013 | Berthon-Jones et al. |
| 10,307,554 B2 | 6/2019 | Berthon-Jones et al. |
| 10,940,283 B2 | 3/2021 | Berthon-Jones et al. |
| 2001/0020474 A1 | 9/2001 | Hecker et al. |
| 2002/0005198 A1 | 1/2002 | Kwok et al. |
| 2002/0020416 A1* | 2/2002 | Namey ............... B29C 45/1676 128/205.25 |
| 2002/0023649 A1 | 2/2002 | Gunaratnam |
| 2002/0029780 A1 | 3/2002 | Frater et al. |
| 2002/0046755 A1 | 4/2002 | Devoss |
| 2002/0053347 A1 | 5/2002 | Ziaee |
| 2002/0061692 A1 | 5/2002 | Steckmann |
| 2002/0066452 A1 | 6/2002 | Kessler et al. |
| 2002/0069872 A1 | 6/2002 | Gradon et al. |
| 2002/0096178 A1 | 7/2002 | Ziaee |
| 2002/0100479 A1 | 8/2002 | Scarberry |
| 2002/0124849 A1 | 9/2002 | Billette De Villemeur |
| 2002/0143296 A1 | 10/2002 | Russo |
| 2002/0157673 A1 | 10/2002 | Kessler et al. |
| 2002/0174868 A1 | 11/2002 | Kwok et al. |
| 2002/0185134 A1 | 12/2002 | Bishop |
| 2003/0000526 A1 | 1/2003 | Goebel |
| 2003/0019495 A1 | 1/2003 | Palkon et al. |
| 2003/0056795 A1 | 3/2003 | Michelson |
| 2003/0075182 A1 | 4/2003 | Heidmann |
| 2003/0079749 A1 | 5/2003 | Strickland et al. |
| 2003/0089373 A1 | 5/2003 | Gradon et al. |
| 2003/0111080 A1 | 6/2003 | Olsen et al. |
| 2003/0154980 A1 | 8/2003 | Berthon-Jones et al. |
| 2003/0168063 A1 | 9/2003 | Gambone et al. |
| 2003/0196656 A1 | 10/2003 | Moore et al. |
| 2003/0196658 A1 | 10/2003 | Ging et al. |
| 2004/0025885 A1 | 2/2004 | Payne, Jr. |
| 2004/0045551 A1 | 3/2004 | Eaton |
| 2004/0065328 A1 | 4/2004 | Amarasinghe et al. |
| 2004/0106891 A1 | 6/2004 | Langan et al. |
| 2004/0111104 A1 | 6/2004 | Schein et al. |
| 2004/0112384 A1 | 6/2004 | Lithgow et al. |
| 2004/0118406 A1 | 6/2004 | Lithgow et al. |
| 2004/0127856 A1 | 7/2004 | Johnson |
| 2004/0211428 A1 | 10/2004 | Jones |
| 2004/0226564 A1 | 11/2004 | Persson |
| 2004/0226566 A1 | 11/2004 | Gunaratnam et al. |
| 2004/0255950 A1* | 12/2004 | Gradon ............. A61M 16/0638 128/206.26 |
| 2005/0011523 A1 | 1/2005 | Aylsworth et al. |
| 2005/0028822 A1 | 2/2005 | Sleeper et al. |
| 2005/0033247 A1 | 2/2005 | Thompson |
| 2005/0039757 A1 | 2/2005 | Wood |
| 2005/0051171 A1 | 3/2005 | Booth |
| 2005/0051176 A1 | 3/2005 | Riggins |
| 2005/0056286 A1 | 3/2005 | Huddart et al. |
| 2005/0061326 A1 | 3/2005 | Payne, Jr. |
| 2005/0101933 A1 | 5/2005 | Marrs et al. |
| 2005/0150495 A1 | 7/2005 | Rittner et al. |
| 2005/0155604 A1 | 7/2005 | Ging et al. |
| 2005/0211252 A1 | 9/2005 | Lang et al. |
| 2005/0241644 A1 | 11/2005 | Gunaratnam et al. |
| 2005/0284481 A1 | 12/2005 | Meyer |
| 2006/0060200 A1 | 3/2006 | Ho et al. |
| 2006/0081250 A1 | 4/2006 | Bordewick et al. |
| 2006/0095008 A1 | 5/2006 | Lampropoulos et al. |
| 2006/0095009 A1 | 5/2006 | Lampropoulos et al. |
| 2006/0118117 A1 | 6/2006 | Berthon-Jones |
| 2006/0124131 A1 | 6/2006 | Chandran et al. |
| 2006/0137690 A1 | 6/2006 | Gunaratnam et al. |
| 2006/0174887 A1 | 8/2006 | Chandran et al. |
| 2006/0207597 A1 | 9/2006 | Wright |
| 2006/0237017 A1 | 10/2006 | Davidson et al. |
| 2006/0283461 A1 | 12/2006 | Lubke et al. |
| 2007/0023044 A1 | 2/2007 | Kwok et al. |
| 2007/0125387 A1 | 6/2007 | Zollinger et al. |
| 2007/0144525 A1 | 6/2007 | Davidson et al. |
| 2007/0186930 A1 | 8/2007 | Davidson et al. |
| 2007/0272249 A1 | 11/2007 | Chandran et al. |
| 2007/0282272 A1 | 12/2007 | Bannon et al. |
| 2008/0004573 A1 | 1/2008 | Kaufmann et al. |
| 2008/0006277 A1 | 1/2008 | Worboys et al. |
| 2008/0047560 A1 | 2/2008 | Veliss et al. |
| 2008/0060649 A1 | 3/2008 | Veliss et al. |
| 2008/0065022 A1 | 3/2008 | Kyvik et al. |
| 2008/0110469 A1 | 5/2008 | Weinberg |
| 2008/0200880 A1 | 8/2008 | Kyvik et al. |
| 2008/0257354 A1 | 10/2008 | Davidson et al. |
| 2009/0044808 A1 | 2/2009 | Guney et al. |
| 2010/0000534 A1 | 1/2010 | Kooij et al. |
| 2010/0000543 A1 | 1/2010 | Berthon-Jones et al. |
| 2010/0018534 A1 | 1/2010 | Veliss et al. |
| 2015/0007822 A1 | 1/2015 | Berthon-Jones et al. |
| 2021/0113800 A1 | 4/2021 | Berthon-Jones et al. |

FOREIGN PATENT DOCUMENTS

| | | |
|---|---|---|
| CN | 2056858 U | 5/1990 |
| DE | 185017 | 5/1906 |
| DE | 30 11 900 | 10/1980 |
| DE | 146 688 | 2/1981 |
| DE | 37 19 009 | 12/1988 |
| DE | 3927038 | 2/1991 |
| DE | 297 23 101 | 7/1998 |
| DE | 197 03 526 | 8/1998 |
| DE | 199 44 242 | 3/2001 |
| DE | 100 02 571 | 7/2001 |
| DE | 10213905 | 10/2002 |
| DE | 10 2004 055 433 | 11/2004 |
| EP | 0 288 937 | 11/1988 |
| EP | 0 427 474 | 5/1991 |
| EP | 0 466 960 | 1/1992 |
| EP | 0 303 090 | 4/1992 |
| EP | 0 658 356 | 6/1995 |
| EP | 0 776 679 | 6/1997 |
| EP | 1 099 452 | 5/2001 |
| EP | 1 258 266 A1 | 11/2002 |
| EP | 1 481 702 | 12/2004 |
| FR | 2720280 | 12/1995 |
| GB | 532214 | 1/1941 |
| GB | 2176404 | 12/1986 |
| GB | 2 368 533 | 5/2002 |
| GB | 2 385 533 | 8/2003 |
| WO | WO 1982/003548 | 10/1982 |
| WO | WO 1987/001950 | 4/1987 |
| WO | WO 1992/020392 | 11/1992 |
| WO | WO 1992/020395 | 11/1992 |
| WO | WO 1996/028207 | 9/1996 |

(56) References Cited

FOREIGN PATENT DOCUMENTS

| | | |
|---|---|---|
| WO | WO 1998/004310 | 2/1998 |
| WO | WO 1998/012965 | 4/1998 |
| WO | WO 1998/023305 | 6/1998 |
| WO | WO 1999/016327 | 4/1999 |
| WO | WO 1999/025410 | 5/1999 |
| WO | WO 1999/043375 A1 | 9/1999 |
| WO | WO 1999/061088 | 12/1999 |
| WO | WO 2000/020072 | 4/2000 |
| WO | WO 2000/038772 | 7/2000 |
| WO | WO 2000/050121 | 8/2000 |
| WO | WO 00/57942 A1 | 10/2000 |
| WO | WO 2000/069521 | 11/2000 |
| WO | WO 00/78384 A1 | 12/2000 |
| WO | WO 2000/072905 | 12/2000 |
| WO | WO 2000/074758 | 12/2000 |
| WO | WO 2000/076568 | 12/2000 |
| WO | WO-0078381 A1 * 12/2000 ........ A61M 16/0066 |
| WO | WO 01/32250 | 5/2001 |
| WO | WO 2001/062326 | 8/2001 |
| WO | WO 01/95965 A1 | 12/2001 |
| WO | WO 2001/095965 A1 | 12/2001 |
| WO | WO 2001/097892 | 12/2001 |
| WO | WO 2001/097893 | 12/2001 |
| WO | WO 02/05883 | 1/2002 |
| WO | WO 2002/038221 | 5/2002 |
| WO | WO 02/45784 A1 | 6/2002 |
| WO | WO 2003/090827 | 11/2003 |
| WO | WO 2003/105921 | 12/2003 |
| WO | WO 2004/022146 | 3/2004 |
| WO | WO 2004/041342 | 5/2004 |
| WO | WO 2004/073778 | 9/2004 |
| WO | WO 2004/078230 | 9/2004 |
| WO | WO 2005/053781 | 6/2005 |
| WO | WO 2005/063328 | 7/2005 |
| WO | WO 2005/086943 | 9/2005 |
| WO | WO 2005/099801 | 10/2005 |
| WO | WO 2005/110220 | 11/2005 |
| WO | WO 2005/118040 | 12/2005 |
| WO | PCT/AU2006/000031 | 1/2006 |
| WO | PCT/AU2006/000417 | 3/2006 |
| WO | PCT/AU2006/000770 | 6/2006 |
| WO | WO 2006/069415 | 7/2006 |
| WO | WO 2006/074513 | 7/2006 |
| WO | WO 2006/074516 | 7/2006 |
| WO | WO 2006/099658 | 9/2006 |
| WO | WO 2006/130903 | 12/2006 |
| WO | WO 2007/009182 | 1/2007 |
| WO | WO 2007/041751 | 4/2007 |
| WO | WO 2007/041786 | 4/2007 |
| WO | WO 2007/048174 | 5/2007 |
| WO | WO 2007/053878 | 5/2007 |
| WO | PCT/AU2007/001936 | 12/2007 |
| WO | WO 2007/143772 | 12/2007 |
| WO | WO 2007/145534 | 12/2007 |
| WO | WO 2008/011682 | 1/2008 |
| WO | WO 2008/011683 | 1/2008 |
| WO | WO 2008/040050 | 4/2008 |
| WO | WO 2008/070929 | 6/2008 |
| WO | WO 2009/108994 | 9/2009 |
| WO | WO 2009/109004 | 9/2009 |
| WO | WO 2010/028425 | 3/2010 |

OTHER PUBLICATIONS

Office Action dated Sep. 2, 2015 issued in U.S. Appl. No. 12/461,448 (23 pages).
U.S. Appl. No. 10/385,701, filed Aug. 2003, Berthon-Jones et al.
U.S. Appl. No. 10/584,711, filed Dec. 2004, Davidson.
U.S. Appl. No. 10/655,622, filed Sep. 2003, Lithgow.
U.S. Appl. No. 10/781,929, filed Jan. 2008, Gunaratnam et al.
U.S. Appl. No. 10/871,929, filed Feb. 2004, Surjaatmadja.
U.S. Appl. No. 11/080,446, filed Jul. 2005, Ging et al.
U.S. Appl. No. 11/447,295, filed Jun. 2006, Lubke et al.
U.S. Appl. No. 11/474,415, filed Jun. 2006, Davidson et al.
U.S. Appl. No. 11/491,016, filed Feb. 2007, Kwok et al.
U.S. Appl. No. 11/597,909, filed Jul. 2007, Worboys.
U.S. Appl. No. 11/703,082, filed Feb. 2007, Davidson.
U.S. Appl. No. 11/878,932, filed Jul. 2007, Veliss et al.
U.S. Appl. No. 11/878,933, filed Jul. 2007, Veliss et al.
U.S. Appl. No. 12/081,696, filed Apr. 2008, Davidson et al.
U.S. Appl. No. 12/085,191, filed May 2008, Kwok et al.
U.S. Appl. No. 12/219,852, filed Jul. 2008, Guney et al.
U.S. Appl. No. 12/309,696, filed Jan. 2009, Kwok et al.
U.S. Appl. No. 12/382,517, filed Mar. 2009, Lithgow.
U.S. Appl. No. 12/448,250, filed Jun. 2009, Veliss et al.
U.S. Appl. No. 12/478,537, filed Jun. 2009, Kooij et al.
U.S. Appl. No. 12/656,466, filed Jan. 2010, Biener et al.
U.S. Appl. No. 12/700,878, filed Feb. 2010, Davidson et al.
U.S. Appl. No. 60/424,686, filed Nov. 2002, Lithgow.
U.S. Appl. No. 60/483,622, filed Jul. 2003, Kwok et al.
U.S. Appl. No. 60/533,214, filed Dec. 2003, Drew.
U.S. Appl. No. 60/634,802, filed Dec. 2004, Chandran.
U.S. Appl. No. 60/645,672, filed Jan. 2005, Chandran.
U.S. Appl. No. 60/795,615, filed Apr. 2006, Judson et al.
U.S. Appl. No. 60/833,841, filed Jul. 2006, Veliss.
U.S. Appl. No. 60/835,442, filed Aug. 2006, Selvarajan et al.
U.S. Appl. No. 60/852,649, filed Oct. 2006, Selvarajan et al.
U.S. Appl. No. 60/874,968, filed Dec. 2006, Kwok et al.
U.S. Appl. No. 60/907,856, filed Apr. 2007, Davidson et al.
U.S. Appl. No. 60/924,241, filed May 2007, Kwok et al.
U.S. Appl. No. 60/929,393, filed Jun. 2007, Kwok et al.
U.S. Appl. No. 60/935,179, filed Jul. 2007, Guney et al.
U.S. Appl. No. 60/935,336, filed Aug. 2007, Davidson et al.
U.S. Appl. No. 60/996,160, filed Nov. 2007, Guney et al.
U.S. Appl. No. 61/006,409, filed Jan. 2008, Guney et al.
U.S. Appl. No. 61/064,818, filed Mar. 2008, Guney et al.
U.S. Appl. No. 61/071,512, filed May 2008, Guney et al.
U.S. Appl. No. 61/213,326, filed May 2009, Dravitzki et al.
U.S. Appl. No. 61/222,711, filed Jul. 2009, Dravitzki et al.
U.S. Appl. No. 61/263,175, filed Nov. 2009, Dravitzki et al.
U.S. Appl. No. 61/272,162, filed Aug. 2009, Dravitzki et al.
U.S. Appl. No. 61/272,250, filed Sep. 2009, Dravitzki et al.
Webster's Third New International Dictionary, 1993, Dictionary definition for adjustable, bendable, and mild steel.
Merriam-Webster Online Dictionary definition of moveable from the $14^{th}$ century.
Webster's New World Dictionary, Third College Edition 1988, definition for engaged and flexible.
ComfortLite™ 2, Respironics, http://comfortlite2.respironics.com.
ComfortLite™, Respironics, http://comfortlite.respironics.com.
Examination Report filed in New Zealand Application 539836, dated Aug. 25, 2005.
Examiner's Report No. 3 dated Nov. 18, 2009 in New Zealand Application No. 2003275762.
Examination Report dated Mar. 23, 2011 in New Zealand Application No. 591788 (2 pages).
First Office Action dated Aug. 12, 2011 in Chinese Patent Application No. 200910135465.7 (13 pages).
Second Office Action dated Jun. 11, 2012 in Chinese Application No. 200910135465.7 (9 pages).
Third Office Action dated Nov. 5, 2012 in Chinese Application No. 200910135465.7 (5 pages).
Fourth Office Action dated May 28, 2013 in Chinese Application No. 200910135465.7 including May 17, 2013 Chinese Search Report (14 pages).
Fifth Office Action dated Oct. 30, 2013 in Chinese Application No. 200910135465.7 (4 pages).
Extended European Search Report dated Dec. 3, 2013 in European Application No. 12190847.9 (7 pages).
Extended European Search Report dated Dec. 3, 2013 in European Application No. 12190857.8 (7 pages).
Supplementary Search Report dated Dec. 18, 2009 in European Patent Appln. No. 03810331.3.
Supplementary Search Report dated Dec. 18, 2009 issued in European Patent Appl. No. 03810331.3.
"Ear Loop Face Mask".

(56) References Cited

OTHER PUBLICATIONS

Office Action dated Mar. 2, 2010 issued in Japanese Application No. 2005-502078.
Adam J. Singer MD et al. "The Cyanoacrylate Topical Skin Adhesives," American Journal of Emergency Medicine, vol. 26, 2008, pp. 490-496.
"If You Hate CPAP! You Need CPAP Pro®," www.cpappro.com.
EP Supplementary Search Report issued in EP Application 03793493, dated Dec. 2, 2009.
European Search Report filed on Jul. 27, 2009 in EP Application No. 07784697.0.
European Search Report issued in EP 07845378.4, dated Dec. 1, 2009.
Extended European Search Report dated Mar. 19, 2009 in European Application No. EP 08161249.
Extended European Search Report dated Sep. 3, 2009 in corresponding EP Application No. 09161984.1.
Extended European Search Report. Application No. EP 08154854, dated Nov. 27, 2008.
Fisher and Paykel Col.—Product Family—http://www.fphcare.com/osa/products.asp/.
Hans Rudolph, Inc.—Mask Products—http://www.rudolphkc.com/products.php?category=MASKS.
International Preliminary Report on Patentability for PCT/AU2004/001832, dated Jul. 3, 2006.
International Search Report for PCT/AU2005/000803, dated Jun. 30, 2005.
International Search Report filed in PCT/AU2006/000770, dated Aug. 3, 2006.
International Search Report for PCT/AU2004/001832, dated Mar. 24, 2005.
International Search Report for PCT/AU2007/001051, dated Nov. 5, 2007.
International Search Report for PCT/AU2007/001052, dated Oct. 9, 2007.
International Search Report for PCT/AU2007/001936, dated Mar. 4, 2008.
International Search Report PCT/AU2003/001163, dated Nov. 4, 2003.
International Search Report PCT/AU2003/001471, dated Feb. 12, 2004.
International Search Report PCT/AU2009/000240, dated May 21, 2009.
International Search Report PCT/AU2009/000262, dated Jun. 9, 2009.
International Search Report PCT/AU2009/001144, dated Dec. 18, 2009.
Joel W. Beam, "Tissue Adhesives for Simple Traumatic Lacerations," Journal of Athletic Training, 2008, vol. 43, No. 2, pp. 222-224.
Office Action dated Dec. 22, 2009 in European Appln. No. 04802133.1.
ResMed Co.—Mask Products—http://resmed.com/portal/site/ResMedUS/index.jsp?. . . .
Respironics Co.—Mask Family—http://masksfamily.respironics.com/.
Snapp Nasal Interface, Tiara Medical Systems, Inc.—http://www.tiaramed.com/asp_shops/shopdisplayproducts.asp?id=109&cat=SNAPP%2A+Nasal+Interface.
Subbu Venkatraman et al., "Review Skin Adhesives and Skin Adhesion 1. Transdermal Drug Delivery Systems," Biomaterials, vol. 19, 1998, pp. 1119-1136.
Supplementary European Search Report dated Sep. 8, 2009 in European Appln. No. 04802133.1.
Supplementary Search Report issued in European Appln. 05746824.1, dated Dec. 17, 2009.
Unsolicited email from Elson Silva, PhD, dated Mar. 28, 2008, "Requesting IDS of U.S. Pat. No. 6,766,817 for patents on fluids moving on porosity by Unsaturated Hydraulic Flow," (email provided in both HTML and plain text format).

\* cited by examiner

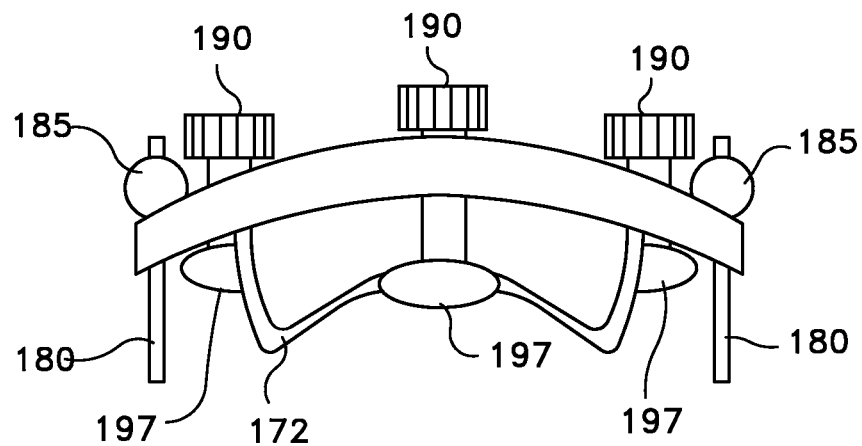
Fig. 42B
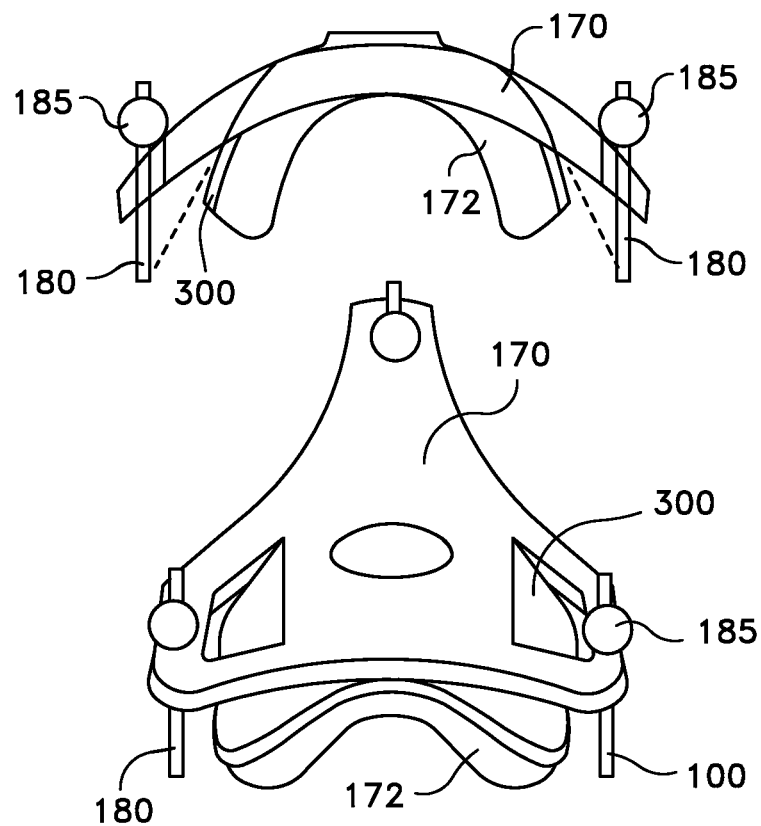
Fig. 43A
Fig. 43B

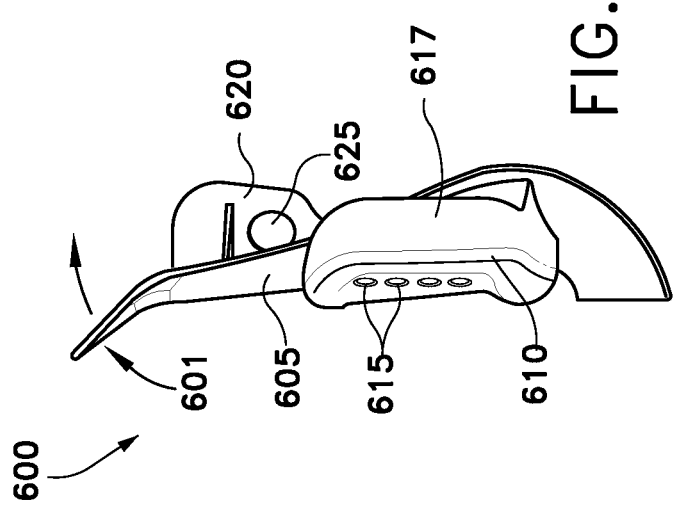
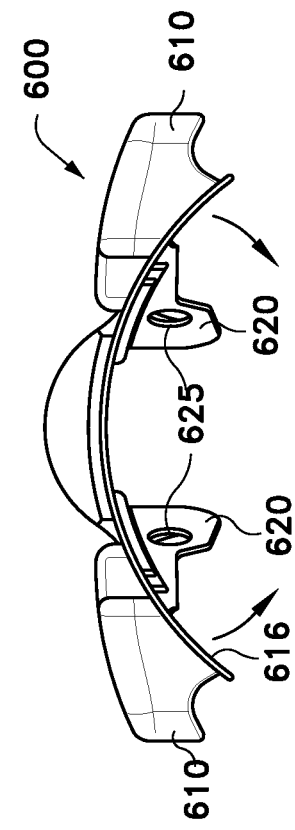
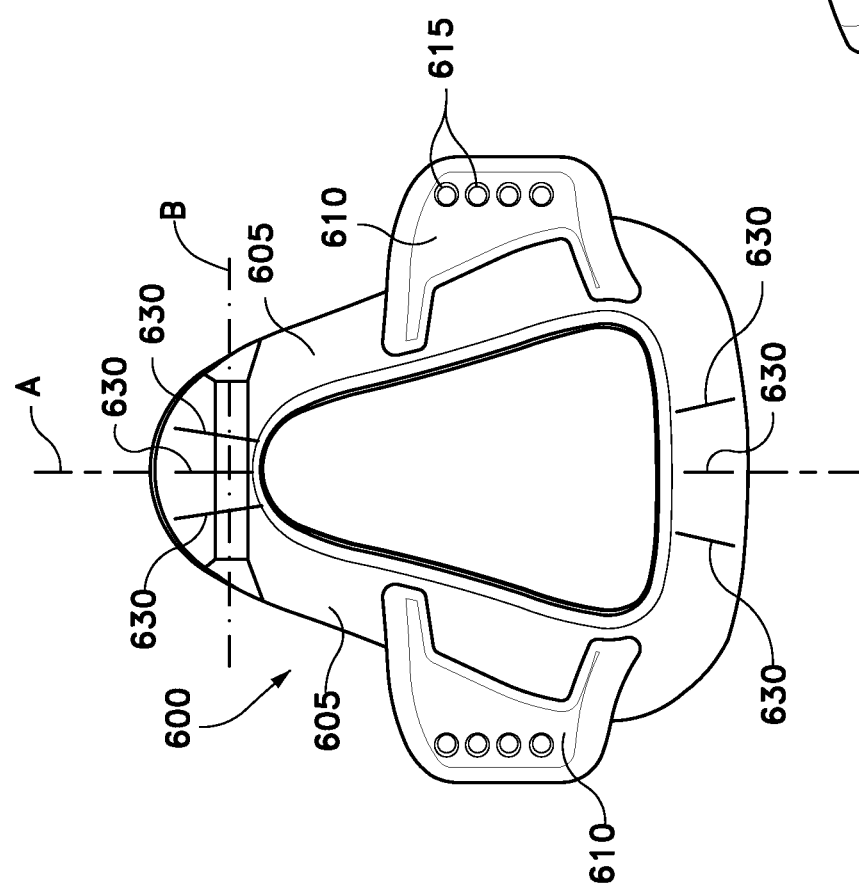
FIG. 53B
FIG. 53C
FIG. 53A

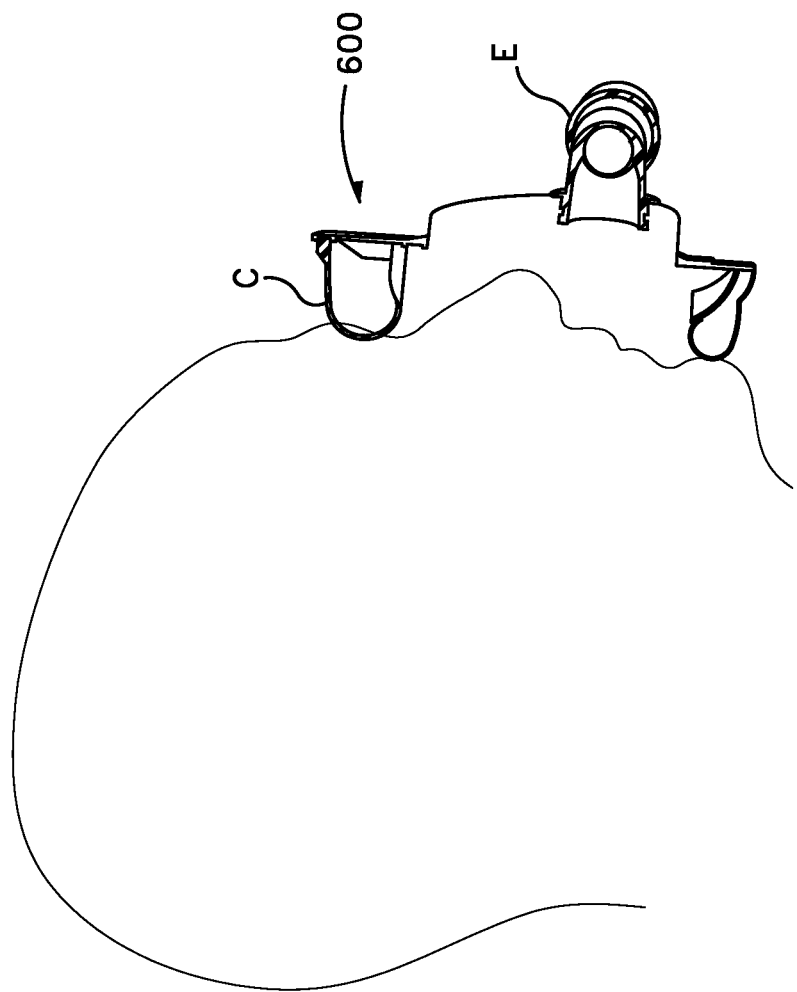

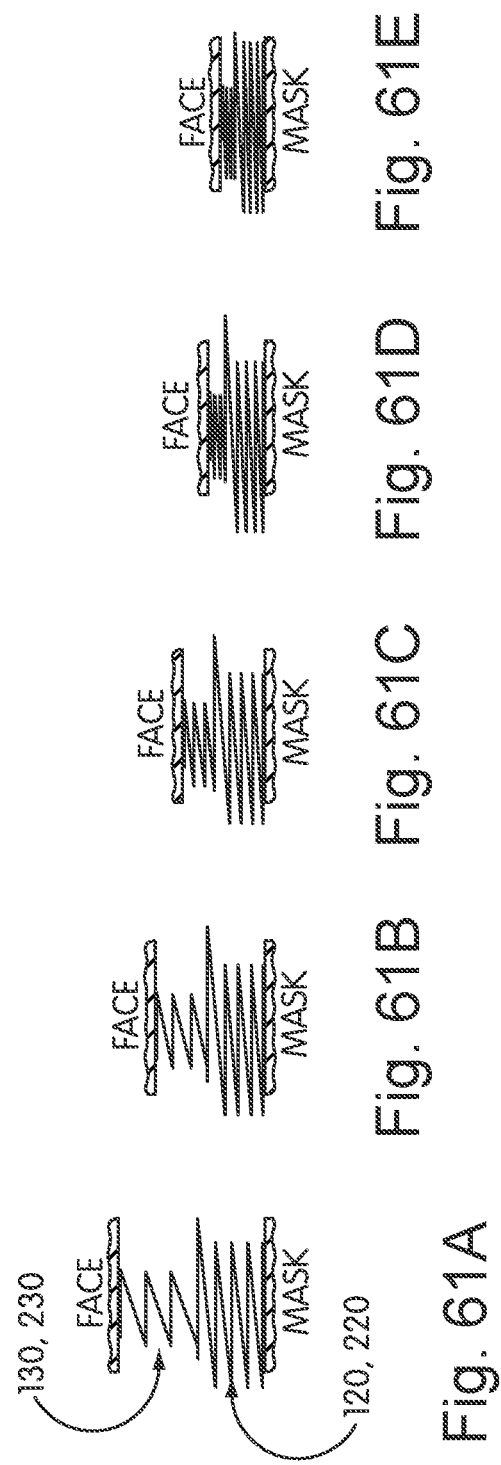

MASK AND COMPONENTS THEREOF

CROSS-REFERENCES TO RELATED APPLICATIONS

This is a continuation of U.S. application Ser. No. 17/131,973, filed Dec. 23, 2020, which is a continuation of U.S. application Ser. No. 14/471,525, filed Aug. 28, 2014, now U.S. Pat. No. 10,940,283, which is a continuation of U.S. application Ser. No. 12/461,448, filed Aug. 12, 2009, now U.S. Pat. No. 10,307,554, which is a continuation of U.S. application Ser. No. 10/533,928, filed Jul. 29, 2005, now U.S. Pat. No. 8,490,623, which is a U.S. national phase of international application PCT/AU2003/01471, filed Nov. 6, 2003, which designated the U.S. and claims benefit of U.S. Application No. 60/424,005, filed Nov. 6, 2002; U.S. Application No. 60/447,327, dated Feb. 14, 2003; U.S. Application No. 60/488,752, dated Jul. 22, 2003; and U.S. Application No. 60/503,896, filed Sep. 22, 2003, each of which is incorporated by reference in its entirety.

BACKGROUND OF THE INVENTION

The invention relates to a full-face mask for use with Non-Invasive Positive Pressure Ventilation (NIPPV), Continuous Positive Airway Pressure (CPAP) and ventilators generally.

The delivery of a supply of breathable gas at positive pressure to a patient from a ventilator requires some sort of interface between machine and patient. An endo-tracheal tube is typically used as a patient interface in invasive ventilation. In non-invasive ventilation, some form of mask is used as a patient interface.

A mask typically comprises a chamber having a nose-receiving cavity defined by a shell or frame. The mask typically further comprises a comfortable face-contacting portion, such as a cushion, which may be secured to an edge of the shell or frame. Masks are typically held in position on a patient's face using an arrangement of headgear, such as a set of elastic straps. It is a continuing challenge for mask designers to improve the comfort of masks, particularly where the mask has to be worn for many hours.

Unless a mask is constructed for each user, because of the wide variety of shapes, most designs of masks represent a compromise. One design of mask might be a good fit for a sub-group of patients with one shape of nose (e.g., with a high nasal bridge), but poorly fit another sub-group with a different shape of nose (e.g., with a low nasal bridge). It can be particularly difficult to design a mask which provides a good seal in the nasal bridge region because that region of the face is particularly sensitive.

Folds and creases in the mask cushion can become very uncomfortable on a patient's face with prolonged wear. Furthermore, in spite of the use of a cushion, the edge of a mask frame can be felt through the cushion and present an uncomfortable surface to the patient's face, particularly if the cushion is compressed.

In some cases it is appropriate for a mask to include a vent which amongst other things can allow a controlled leak flow of gas from the mask to prevent a build up of $CO_2$ within the mask. There may also be inadvertent or unintentional leak from the mask, for example, at a junction between the mask and the patient's skin. The functioning of sophisticated control algorithms in ventilators, particularly those responding to a respiratory flow signal, is improved with the use of a mask which provides low or zero unintentional leak flow.

Patients move during sleep. In addition, the shape of their head can change during sleep, due to, for example, swelling. While a mask may fit a patient well when initially fitted, because of such movement, the mask may not fit well later in the night. Prior art masks typically include elastic headgear straps that can be shortened or stretched or otherwise rearranged on the head to return the mask to a comfortable low-leak position.

The level of pressure support provided by the ventilator can vary during the course of treatment. Some Continuous Positive Airway Pressure (CPAP) devices provide an initial ramp from a low pressure up to a therapeutic pressure. Other CPAP devices automatically adjust the pressure in accordance with indications of flow limitations. Other devices vary the level of pressure support within a respiratory cycle of the patient, for example, by providing a higher level during inhalation and a lower level during exhalation. Elastic headgear straps must be arranged to suit the level of pressure. If the elastic straps are arranged to suit a high pressure level, there is a risk that the straps will be too tight and uncomfortable for a low pressure level.

BRIEF SUMMARY OF THE INVENTION

It is an aspect of the invention to provide a comfortable low-leak mask for use with Non-Invasive Positive Pressure Ventilation that overcomes the limitations of prior art masks.

In another aspect, it is desirable to provide a mask system that has one or more of the following features, each of which may assist with improving patient compliance and/or treatment: headgear including straps that are substantially inextensible and/or micro-adjustable; and/or a mask and/or cushion that includes various structures to allow enhanced/tailored sealing and/or fit at selected locations on the patient's face.

In the description that follows, the following anatomical terms may be used:

Cephalic: In the direction of a vector running from feet to head, and beyond. The nose is cephalad to the lips and chin.

Caudal: In the direction of a vector running from head to feet, and beyond.

Anterior: In the direction of a vector running from the back of the body to the front of the body, and beyond. The nose is anterior to the ears, and the mask is anterior to the nose.

Posterior: In the direction of a vector running from the front of the body to the back. The ears are posterior to the nose.

Coronal plane: A plane parallel to the plane containing the head, feet, and tips of the shoulders. A strap passing from the left ear, over the top of the head, to the right ear would be a coronal strap.

Sagittal plane: A plane parallel to a plane passing through the head, feet, back of the spine, and tip of the nose.

Nuchal: Pertaining to the (muscles of the) back of the neck.

Occipital: Pertaining to the bony prominence where the muscles at the back of the neck insert into the back of the base of the skull.

External auditory meatus: Ear hole.

KgF: Kilograms force.

Zygoma: The roughly half-apricot sized anterior protrusion of the cheekbone (Strictly body of zygoma).

Inner canthus: The point where the upper and lower eyelid meet next to the bridge of the nose.

These and other aspects will be described in or apparent from the following detailed description of illustrated embodiments.

BRIEF DESCRIPTION OF THE DRAWINGS

The illustrated embodiments will be described in relation to the following drawings; wherein like reference numbers may refer to like parts, in which:

FIGS. 41-53 illustrate alternative embodiments of the present invention showing frames/cushions enabling enhanced sealing along the sides of the patient's nose;

FIGS. 53A-G illustrate further embodiments of a frame in which fins are provided to support the cushion;

FIG. 61A-61E are graphical representations of the operation of the cushion assemblies according to the first and second embodiments under a compressive force;

DETAILED DESCRIPTION OF THE INVENTION

The following detailed description of the invention includes disclosure of a number of different features which are applied to various embodiments of mask assemblies. It is to be understood that any feature described in relation to one embodiment may be used in conjunction with one or more features in another embodiment.

Headgear

A. Inextensible Straps

Figure 1:
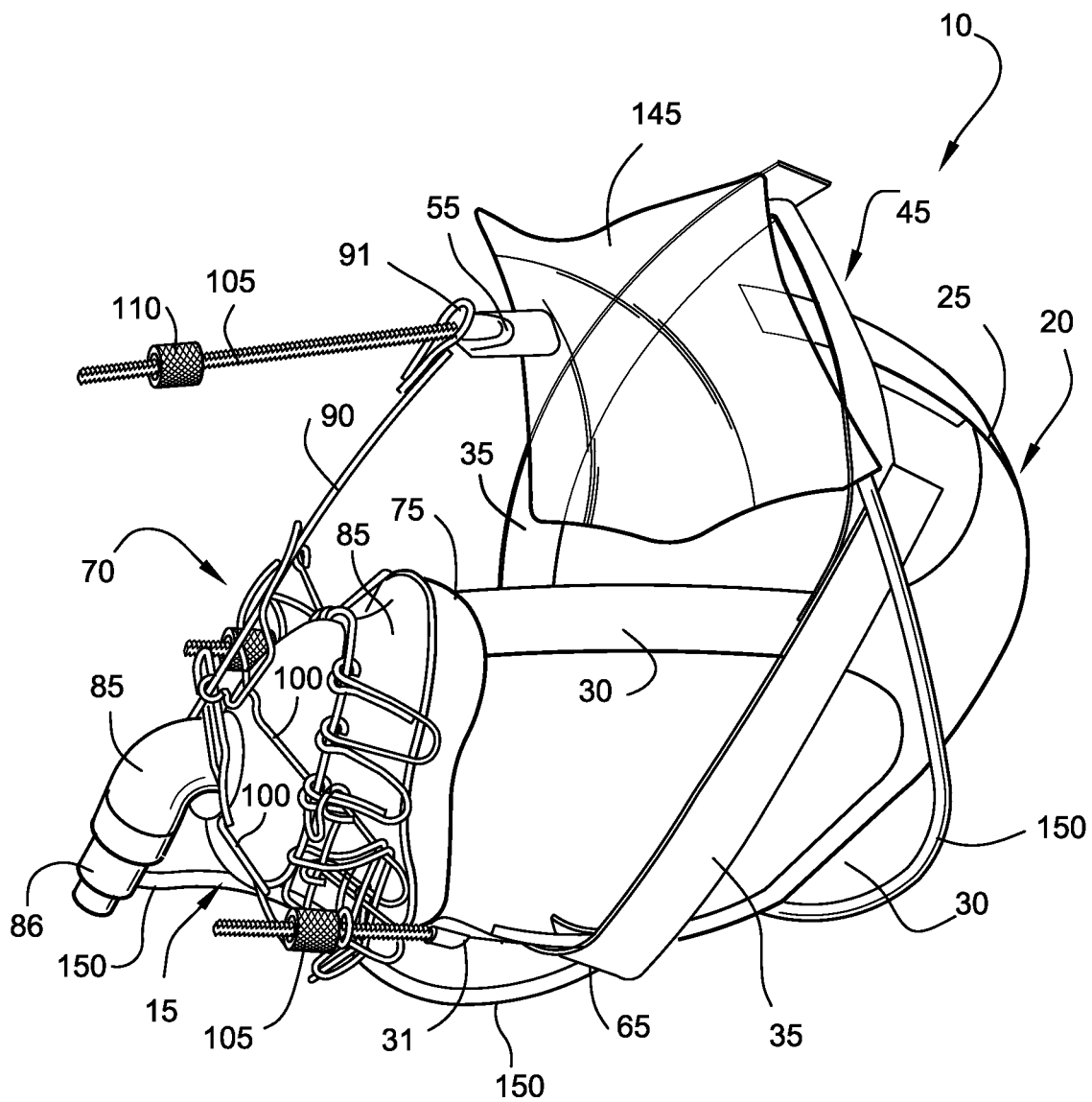
FIGS. 1-5 illustrate a first embodiment of the present invention.

FIGS. 1-5 show one embodiment of a mask system, including a mask assembly 15 and a headgear assembly 20. As shown in FIG. 1, the headgear assembly 20 includes a plurality of straps that are configured and arranged so as to substantially surround the patient's head. These straps are connected to the mask assembly 15 to thereby retain the mask assembly 15 in relation to the patient's face. The mask assembly 15 is shown merely as an example to demonstrate the application of the headgear assembly 20. The mask assembly 15 may be substituted by any suitable respiratory mask, as would be apparent to one of ordinary skill in the art.

To retain the mask assembly 15 in position, the headgear assembly 20 utilizes a sagittal strap 25 and a horizontal strap 30. The horizontal strap 30 is arranged generally horizontally and is wrapped circumferentially around the patient's head. Each end 31 of each horizontal strap 30 is coupled to the mask assembly 15. The arrangement between the horizontal strap 30 and the mask assembly 15 will be discussed in further detail below. The horizontal strap 30 is preferably arranged to pass just inferiorly to each ear and across the insertion area of the neck muscles into the base of the skull which is generally indicated at 36 in FIG. 2.

A posterior end 40 of the sagittal strap 25 is provided generally at a midpoint of the horizontal strap 30 so as to be positioned at an intermediate posterior area of the patient's head. As can be seen in FIG. 1, the width of the sagittal strap 25 at the posterior area of the patient's head is relatively wide, e.g., about twice the width of the remaining portions of the sagittal strap 25. This increase in surface area is advantageous as it helps to prevent the strap from sinking into a very fatty or compliant back portion of the patient's head as pressure changes, or as strap tension changes. Of course, the strap 25 should not be so wide and/or thick that it becomes uncomfortable. The strap may be made from a cool material, such as BREATHOPRENE™.

Figure 2:
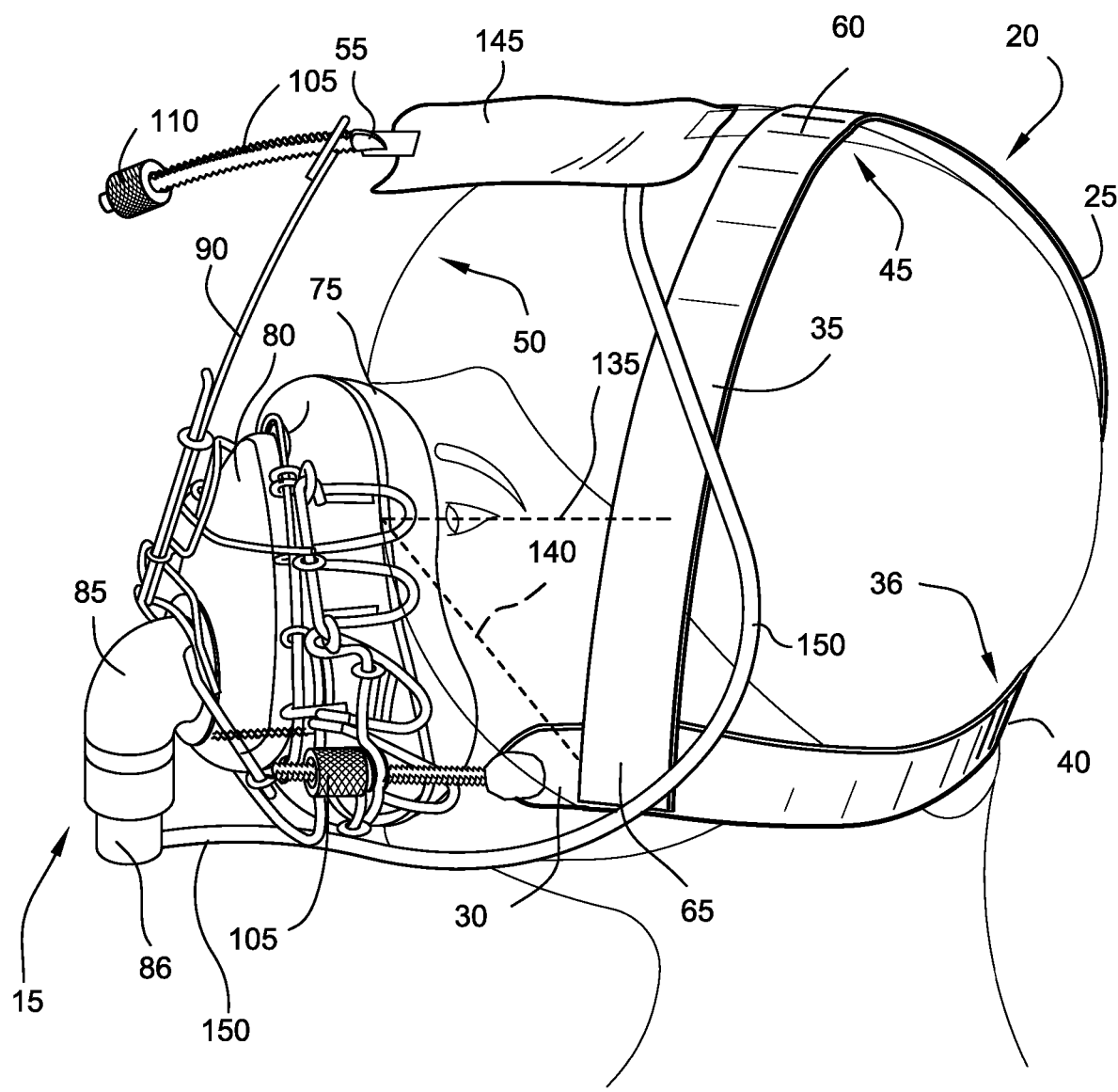

The sagittal strap 25 extends from the horizontal strap 30, e.g., the posterior end 40f, across the vertex of the skull, generally indicated at 45, and extends generally interiorly across a forehead of the patient's head, generally indicated at 50 (see FIG. 2). The sagittal strap 25 has an anterior end 55 coupled to the mask assembly 15, as will be discussed in further detail below.

It may also be preferable for the headgear assembly 20 to include a pair of coronal straps 35 that interconnect the sagittal and horizontal straps 25, 30. A superior end 60 of each coronal strap 35 is connected to the sagittal strap 25 proximate the vertex 45 of the patient's head. Each coronal strap 35 extends from the vertex 45, e.g., the superior end 60, laterally and inferiorly across the head and connects to the horizontal strap 30 just anteriorly to and just inferiorly to each ear at inferior ends 65 of the coronal straps 35.

Each inferior end 65 of the coronal straps 35 may be connected to the horizontal strap 30 via stitching and/or an adhesive. Alternatively, the horizontal strap 30 can be connected with both the coronal straps 35 and/or the sagittal strap 25 with one or more clip elements which will allow adjustability between one or more of the strap portions. Alternatively, it is possible that one or more of the straps of the headgear assembly 20 may be formed from a single piece of material.

To maintain a secure and comfortable fit of the mask assembly 15, the straps of the headgear assembly 20 are preferably formed to be substantially inextensible. Stated differently, the straps may be somewhat flexible, however, the straps are preferably not capable of significant elongation. The straps have sufficient stiffness or rigidity to retain their shape. Contemplative materials for the straps include polyvinylchloride (PVC), leather, polypropylene, or polyurethane. Other materials are, of course, possible. For example, another contemplated suitable material may be a relatively strong cloth tape. It is also contemplated that the straps may be lined with a felt material to add a degree of comfort to the patient. Other alterations may include perforations or holes to allow cooling through the straps.

B. Micro-Adjustment of Straps

1. First Embodiment

Referring to FIG. 1, the headgear assembly 20 is coupled to the mask assembly 15, preferably in a manner so as to allow adjustment of the position of the mask assembly 15 relative to the straps of the headgear assembly 20. The mask assembly 15 includes a frame assembly 70, a cushion 75 to interface or make contact with the patient, and a cushion support 80 interposed between the frame assembly 70 and the cushion 75. The cushion support 80 includes an aperture (not shown) by which pressurized air is provided to a pressurized chamber of the mask assembly 70, which is delivered to the airways of the patient. Typically, an elbow 85 is releasably connected to the aperture of the cushion support 80. The swivel elbow includes a quick release connector 86 that is provided to an air delivery tube (not shown) which in turn is coupled to an air delivery device, e.g., a flow generator (not shown).

The frame assembly 70 includes a chassis 95 (best shown in FIG. 3) provided with one or more cross members 100. The cross members 100 support a cantilevered extension 90 which is coupled to the anterior end 55 of the sagittal strap 25. The anterior end 55 of the sagittal strap 25 is provided with a threaded portion 105 that is guided through a receiving aperture 91 provided on the extension 90, as best shown in FIGS. 1 and 2. A nut 110 can be rotated about the threaded portion 105 to thereby adjust the distance between the extension 90 and the forehead 50 of the patient. Accordingly, the strap tension can be finely adjusted especially if the sagittal strap 25 is made of a substantially inextensible material, as described above.

Figure 3:
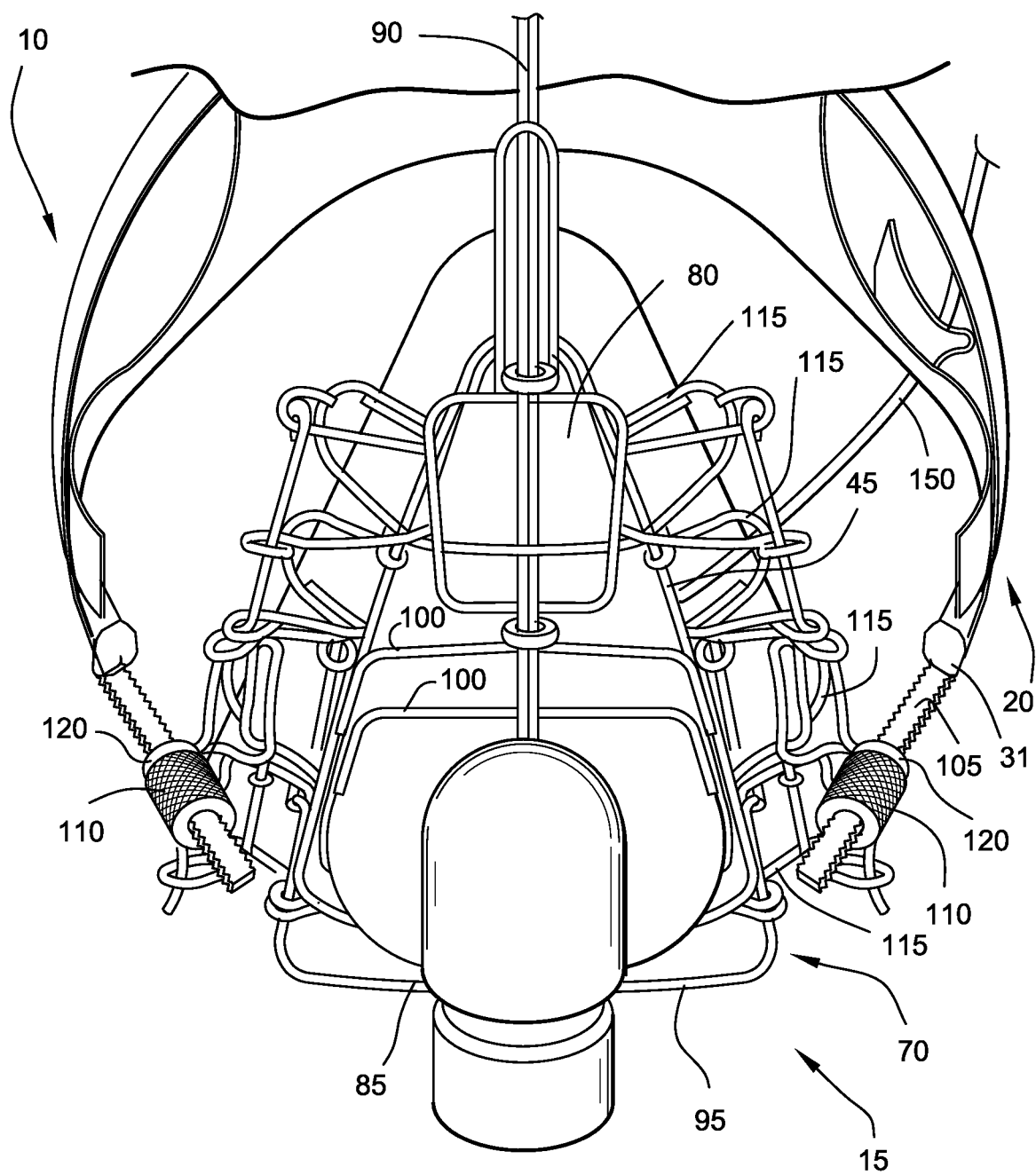

FIG. 3 shows a front view of the mask assembly 10. In FIG. 3, it can be seen that the chassis 95 includes a plurality of finger portions 115 extending away from the chassis 95. The lower most finger member 115 on each side of the chassis 95 includes an aperture 120 configured to receive a threaded portion 105 extending from each end 31 of the horizontal strap 30. A nut 110 is threadedly secured to the threaded portion 105 so that the distance between the mask assembly 15 and the face of the patient can be finely tuned. Accordingly, the straps can be tightened to a high degree of accuracy so that the forces applied to the face are appropriate over a given pressure range, from about 2 to 40 cmH$_2$O.

Figure 4:
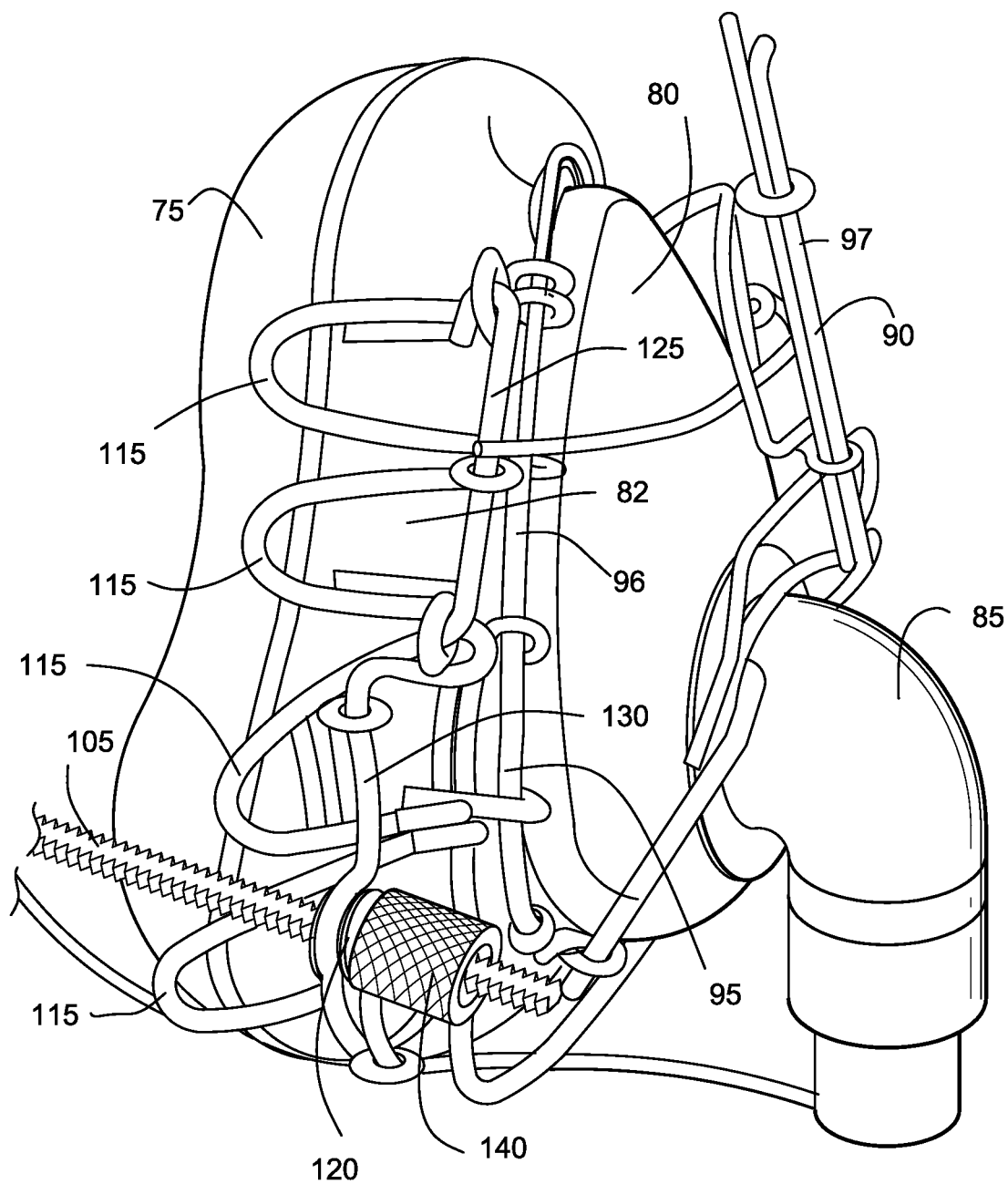

As best shown in FIGS. 3 and 4, the threaded portion 105 has a substantially rectangular cross section, including two relatively flat sides and two sides having threaded sections. The apertures 91 and 120 may have a shape that is relatively complimentary to the shape of the threaded portion 105. For example, the receiving apertures 91, 120 may have a substantially rectangular shape to thereby prevent rotation of the threaded portion 105 when adjusting the nuts 110. This. Although not shown, the end of the threaded portion 105 may also include an element, e.g., a member with a rectangular aperture, to help prevent rotation of the threaded portion 105.

FIG. 4 shows a side view and more clearly shows the connection between each horizontal strap 30 and the frame assembly 70. In addition, FIG. 4 shows that each of the finger portions 115 is movably, e.g., pivotably, connected to transverse portions 96, 97 of the chassis 95. In this particular example, the top two finger portions 115 are interconnected with a cross bar 125 while the bottom two finger members 115 are connected with a similar cross bar 130. Accordingly, the top two finger members and the bottom two finger members, on each side of the chassis, respectively, can move in unison, which may be advantageous from the perspective of force distribution. However, it is contemplated that each of the finger members can be independently movable with respect to the transverse members 96, 97 of the chassis 95.

In this example, the threaded portion 105 which extends from the end 31 of each horizontal strap 30 is threaded through the receiving aperture 120 which is provided to the lower two finger portions 115. As such, as the nut 110 is tightened, any slack which is left in the horizontal strap 30 will be taken up. When all of the slack is taken up, any further tightening of the nut 110 will cause the lower two finger portions 115 on the right hand side to rotate in a clockwise sense (as viewed from above) against the cushion support 80. The lower two portions on the left hand side will rotate in a counter-clockwise sense, as viewed from above.

The cushion support 80 in at least the lateral portions 82 adjacent the finger portions 115 is flexible. Due to this flexibility, the lateral portions 82 impose a force on the corresponding section of the cushion 75 to thereby pinch against the sides of the nose of the patient.

As shown in FIG. 4, the cushion 75 is integrated with the cushion support 80 is flexible or deformable, for example by the fingers 115, in order to better fit the contours of the individual face. There is a trade-off between making the cushion support very flexible to allow better fitting of the face, versus so extremely flexible that the internal volume of the mask changes excessively (e.g., >20 mL) with each breath, which would make measurement of tidal volume difficult. A typical silicone of 1-3 mm thickness is suitable.

Figure 5:
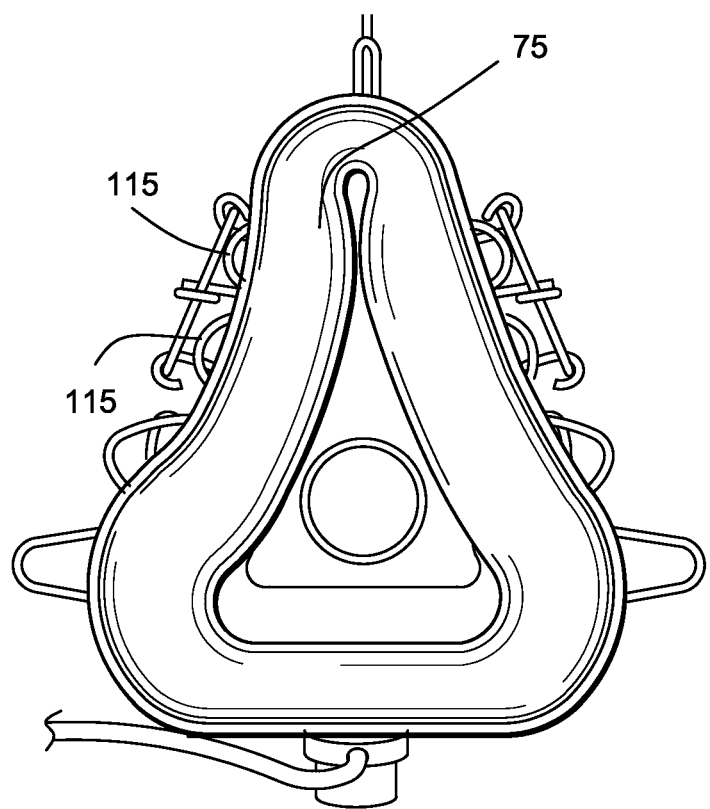

FIG. 5 shows a rear view of the mask assembly 15 in which the upper two finger portions 115 on the left side of the patient's face are manually pushed in against one of the lateral portions 82 of the cushion support 80. The force which is applied from the upper two finger portions 115 to the lateral portion 82 of the cushion 80 causes deformation of the cushion 75 such that it pinches against the side of the nose, thereby accommodating differently shaped noses and enhancing seal performance of the cushion 75.

In FIGS. 1-5, tension in the straps, along with flexibility of the lateral sides 82 of the support 80, causes the fingers to rotate and pinch together thereby squeezing the sides of the nose and possibly a portion of the patient's face. Accordingly, any irregular face structures can be accommodated by the independent rotating capability. This also helps to evenly distribute the load on the face, thereby relieving areas of high contact force.

FIG. 5 shows the effect of increasing tension in the top strap (not shown), which results in pinching in the nasal bridge region of the patient. This is particularly useful for bi-level treatment so that at low pressures only low forces are applied and at high pressures high forces are applied, which is helpful for improved comfort and sealing. The provision of headgear made of an inelastic material helps prevent "pistoning" of the mask on the face, that is to say lifting off the face at high pressure, and/or digging into the face at low pressure during bi-level treatment.

In the embodiment of FIGS. 1-5, the two upper finger portions 115 provided on each transverse portion 96, 97 of the chassis 95 are not shown as being connected to any strap member of the headgear assembly 20. However, the positioning of such upper strap portions may be as shown by the imaginary lines 135, 140 in FIG. 2. In particular, the imaginary line 135 represents a situation where an upper strap portion would be connected to a midsection of the coronal strap 35. Imaginary line 140 represents a situation where an upper strap portion would be connected to the horizontal strap 30 on each side of the headgear.

2. Second Embodiment

Figure 5A:
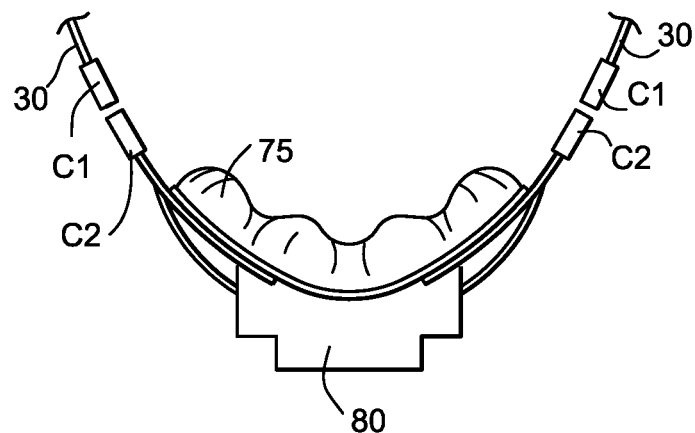
FIGS. 5A and 5B illustrate an alternative embodiment of the present invention.
Figure 5B:
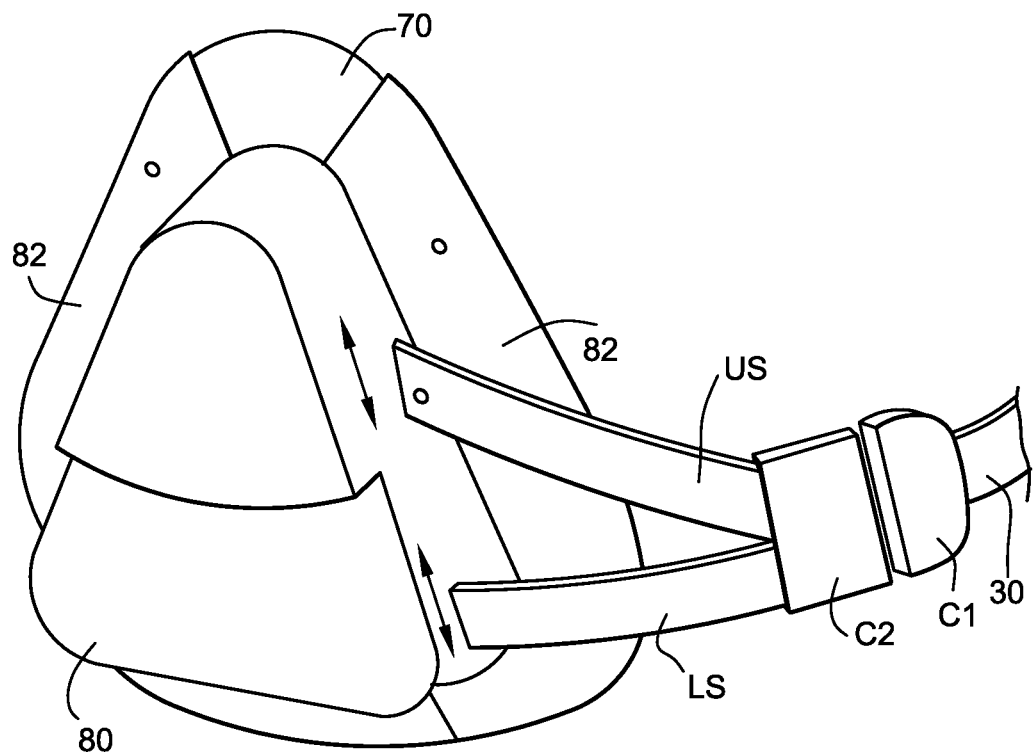

FIGS. 5A and 5B depict an alternative embodiment of the present invention in which a horizontal strap 30 includes a first connector portion C1 that is selectively coupled with a second connector portion C2. The second connector portion C2 is attached to a lower strap LS and an upper strap US. The upper and lower straps LS, US may be tightened to the point where they bear against the transverse portions 82 of the frame 70, thereby imparting an inward force on the cushion 75 to seal laterally against the sides of the patient's nose. The upper and lower straps LS, US can be adjustably fixed to the frame 70 (as indicated by the arrows) to best position the area where the inward force will be applied. In this embodiment, the lateral portions 82 of the support 80 are made of flexible material, while the apex is more rigid.

3. Third Embodiment

Figure 5C:
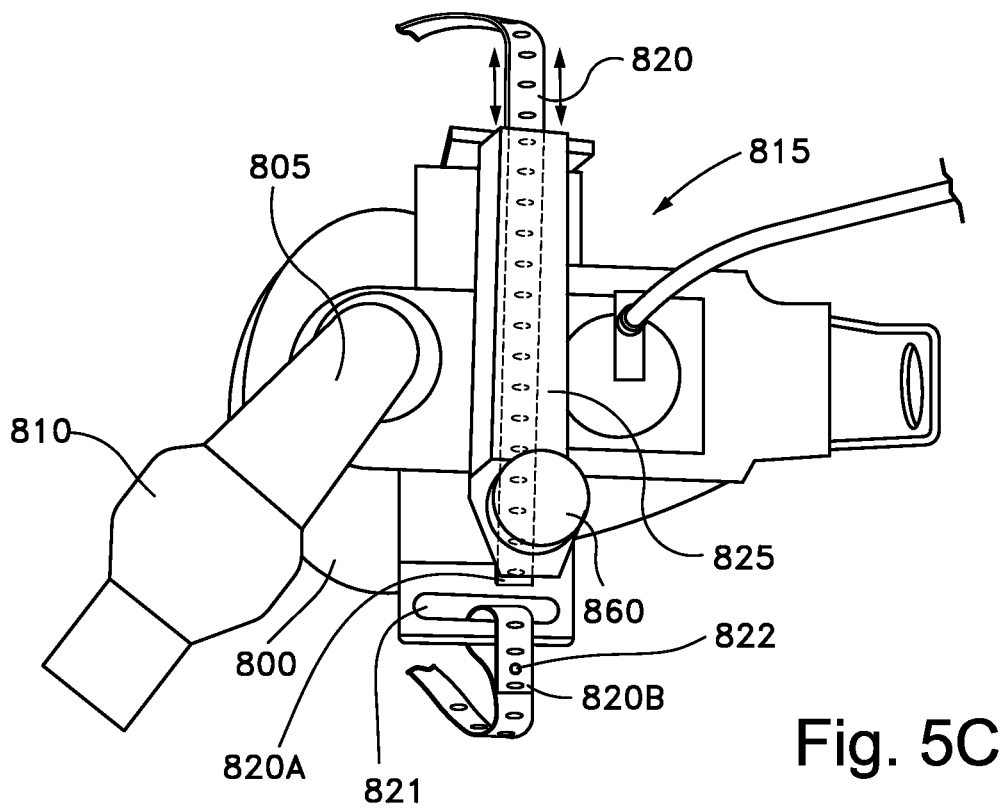
FIGS. 5C-5H illustrate an alternative embodiment of the present invention with micro adjustability and quick-release capability.
Figure 5D:
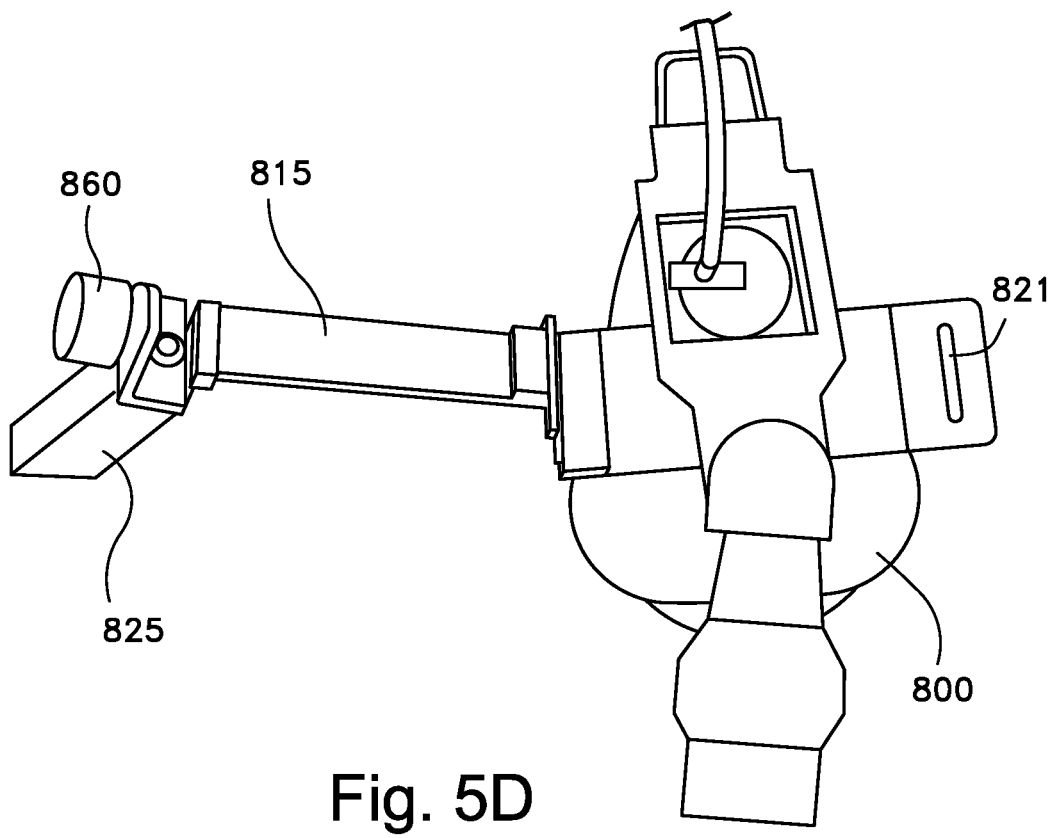
Figure 5E:
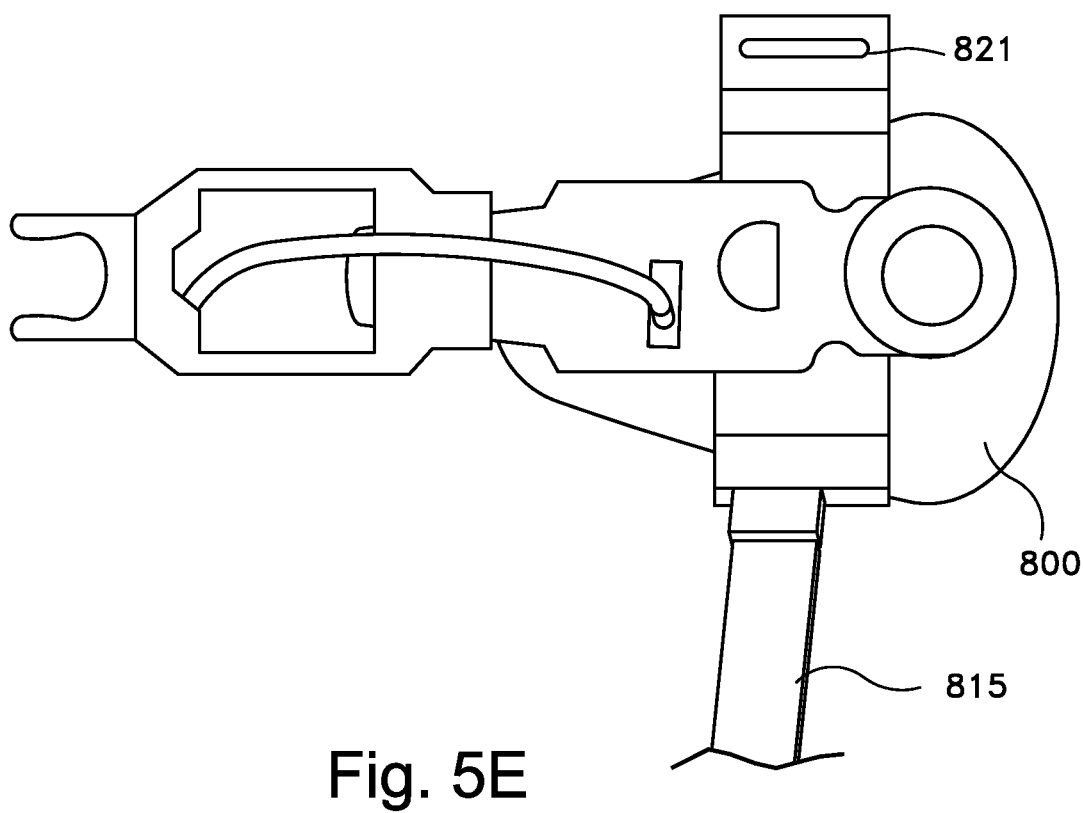

FIGS. 5C-5H illustrate yet another embodiment of the present invention in which an adjustment mechanism allows coarse and fine adjustment of the head strap tension. FIG. 5C shows the overall mask assembly, including a mask frame 800 and which is provided with an elbow 805 including an anti-asphyxia valve 810. A quick release clamp 815 is provided to allow the patient to quickly remove the headgear, as described in U.S. patent application Ser. No. 10/235,846, filed Sep. 6, 2002, incorporated herein by reference in its entirety. FIG. 5D shows the quick release mechanism in a partially opened position, while FIG. 5E shows the quick release mechanism fully opened.

A strap 820 includes a pair of strap ends 820A, 820B provided to hold the mask assembly on the patient's head. One of the strap ends, e.g., 820B may be releasably connected, e.g., via a slot 821, to one end of the mask frame in a fixed position, thereby avoiding variation in length of the strap 820 which could occur with repeated removal and re-placing of the mask assembly. The other strap 820A is positioned and configured to be adjustable. Of course, both ends of the strap 820 may be adjustable. The strap end 820B may be looped through the slot 821 by creating a loop in the strap 820 that is fixed, e.g., via a rivet 822 or other fastener.

Figure 5F:
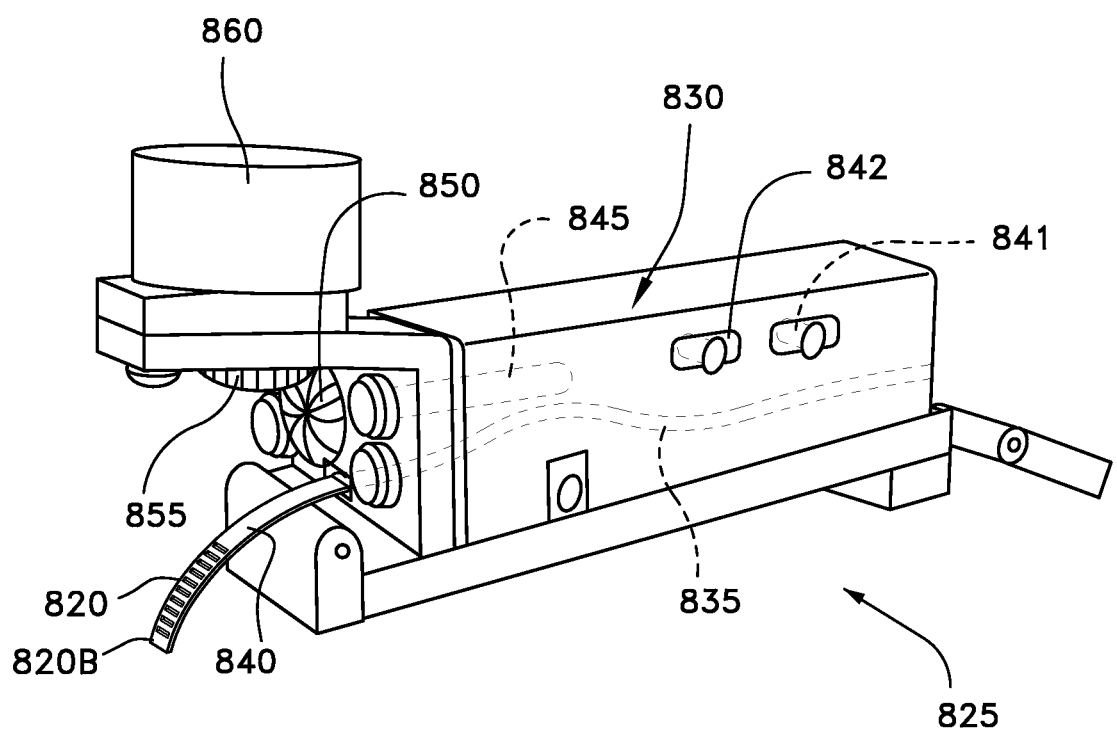
Figure 5G:
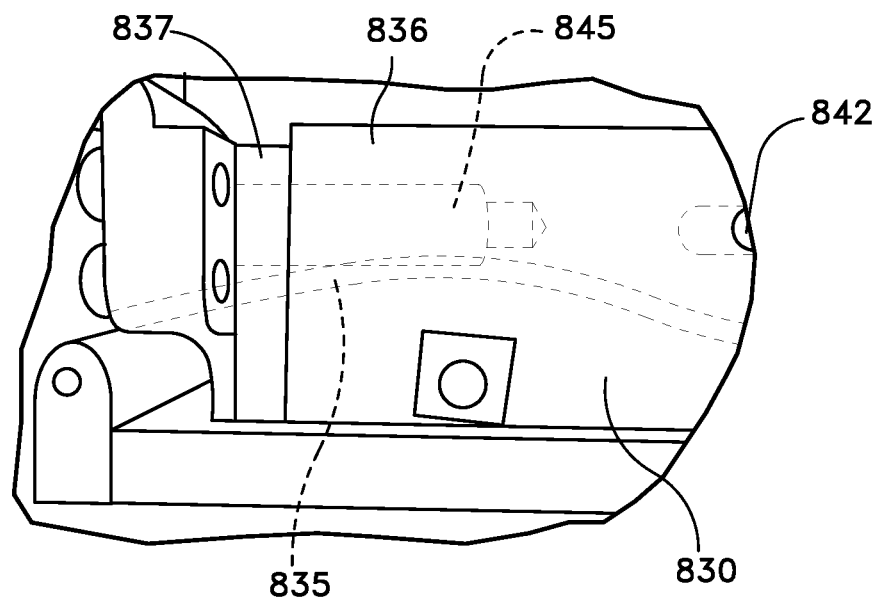
Figure 5H:
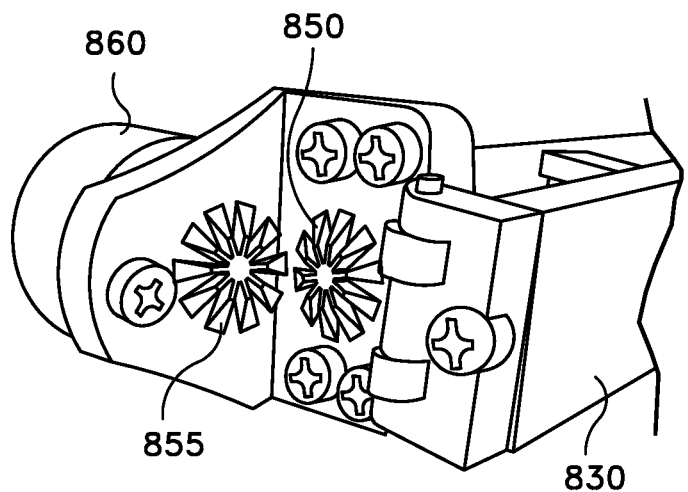

An adjustment assembly 825 may be provided to adjust the strap 820. In particular, as shown in FIG. 5F, the adjustment assembly 825 may include a generally rectangular prism 830 having a strap-receiving slot 835 through its entire length. The slot has an opening 840 shown in the end face of the prism. The prism has an upper portion 836, a lower portion 837 and a threaded screw 845, best shown in FIG. 5G. The upper and lower portions 836, 837 can assume a first position, adapted for coarse adjustment of the strap length, in which the strap end 820A can be pulled through the length of the slot 835. In a second position, adapted for fine adjustment, the upper and lower portions 836, 837 are brought together so that the threaded screw 845 engages with the strap end 820A, preventing its movement through the slot 835. The screw 845, upon rotation, translates the strap end 820A to tighten or loosen the headgear. The upper and lower portions 836, 837 translate via a slot and pin arrangement 841, 842, to enable the screw 845 to move into and out of engagement with the slot 835. The threaded screw 845 has one end extending beyond the length of the prism 835 having a first gear portion 850. As shown in FIG. 5H, the first gear portion 850 in turn engages with a second gear portion 855 at right angles thereto. The second gear portion 855 has a cylindrical knob 860 attached to it. By rotating the cylindrical knob 860, the second gear portion 855 rotates, driving the first gear portion 850 and therefore the screw 845. Depending on the direction of rotation, the strap is either pulled or pushed through the slot, thus enabling fine adjustment of strap length.

C. Inflatable Bladder—Raviolus and Occipital Pneumatic Pillow

1. First Embodiment

Referring to FIG. 1, the headgear assembly 20 is illustrated as including a particular form of bladder which shall be referred to as a "raviolus" 145 provided along, e.g., the sagittal strap 25 of the headgear assembly 20. The raviolus 145 is provided to apply a relatively constant strap force against the patient's face over an entire range of mask pressures. The raviolus 145 is an active component that does pneumatic work to pull the mask onto the face at higher pressure. The raviolus 145 is in communication with pressure in the mask via a small diameter silicone tube 150 attached to a port either on or in close proximity to the mask assembly 15. In this example, the tube 150 is provided to the elbow 85. Tension in the sagittal strap 25 is at least partially driven by flow generator pressure via the raviolus 145, which causes greater strap tension/displacement at higher pressures and less strap tension/displacement at lower pressures.

Although raviolus 145 is shown as the preferred embodiment, variation in strap tension/displacement can be achieved by other mechanisms, including electrical and mechanical systems. As the mask pressure rises, the raviolus pressure rises, causing the raviolus to inflate to a more spherical shape, shortening it anteroposteriorly and therefore pulling posteriorly on cantilever 90, thereby pressing the mask more firmly against the face.

To a first approximation, the posteriorly directed force generated by the raviolus or cantilever 90 is linear on mask pressure. The constant of proportionality is greater as nut 110 is tightened, causing the raviolus to be more elongated at any given mask pressure. Accordingly, the raviolus 145 can be considered an automatic compensating mechanism which if set so that the mask seals at one pressure it will seal at all pressures and it will constantly balance the air pressure in the mask.

Inflating the raviolus by volume ΔV as pressure rises by ΔP does work ΔVΔP to pull the attachment point 91 on cantilever 90 backwards through a distance against a force.

Although the raviolus 145 is only provided on the top strap, others could also be provided on the remaining straps, including the horizontal straps 30. However, no raviolus 145 is applied to the lower straps in this embodiment since the natural tendency of the patient's cheeks and bottom lip to billow somewhat approximates the action of the raviolus 145 to create a good seal in that area over the range of operating pressures. In other words, the sealing mechanism for the top of the mask and the sealing mechanism for the bottom of the mask are different. For the bottom of the mask, the mask designer can rely on the bottom lip and cheeks of the patient to inflate whereas at the top of the mask a different mechanism is used because in part, the facial structure of the nasal bridge region is very bony and rigid.

2. More Details on Raviolus

Having explained the raviolus 145 in general terms, attention is now directed to FIGS. 6-15A which describe more specific principles of the raviolus in detail.

Figure 6:
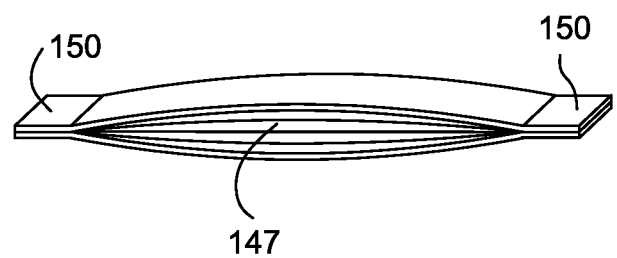
FIGS. 6-15C schematically illustrate a mechanism and principles thereof for changing strap tension in accordance with air pressure supplied to the patient.
Figure 7:
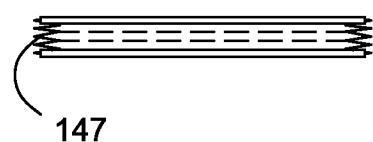
Figure 8:
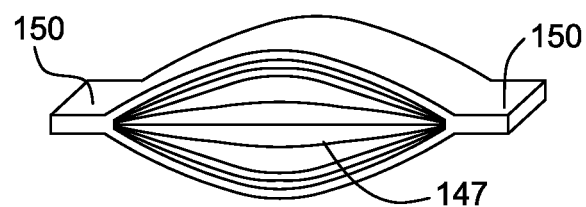
Figure 9:
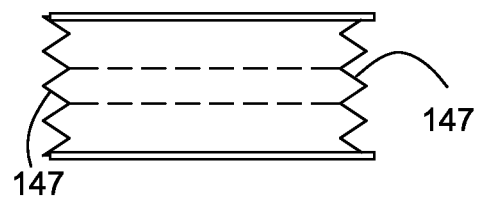

The raviolus 145 may be a rectangular thin walled tube of elastomer such as silicone, pleated along two sides 147, and then sealed at the non-pleated ends 150. The non-pleated sealed ends 150 are inserted into a headstrap of the mask assembly 15, e.g., the sagittal strap 25. FIGS. 6 and 7 show the raviolus 145 in a relaxed state, with little or no pressure, e.g., during expiration of the patient, while FIGS. 8 and 9 show the raviolus 145 under treatment pressure, e.g., during inspiration of the patient. In relation to bilevel ventilation, where the patient is exposed to relatively higher pressure during inspiration and relatively lower pressure during expiration, inflating the raviolus 145 to pressure p, the raviolus 145 will shorten and/or widen, and the headstrap 25 will be pulled tighter.

In the following, the raviolus 145 is assumed to be floppy in the longitudinal direction and stiff transversely, so that it maintains the above flat topped cross section at all pressures. This could be achieved in manufacture, for example, by gluing rigid rods transversely to the top and bottom surfaces, or moulding the top and bottom surfaces to have transverse ridges, and/or by using internal tie wires between the right and left concertina walls. In practice, the basic idea and the following discussion works to a loose approximation without these refinements.

Figure 10:
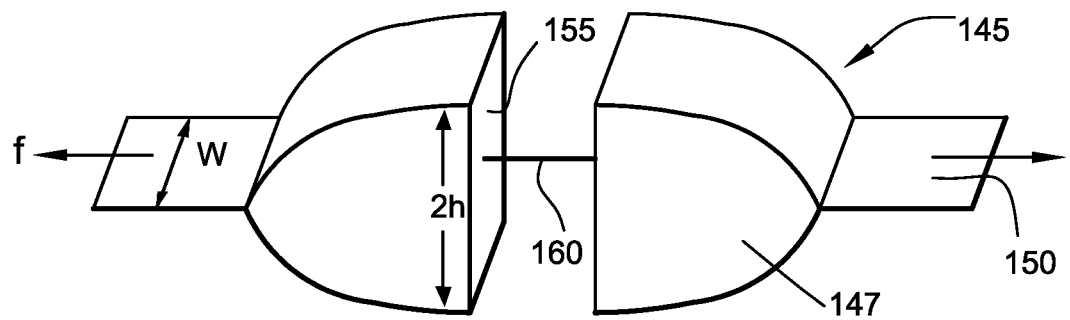
Figure 11:
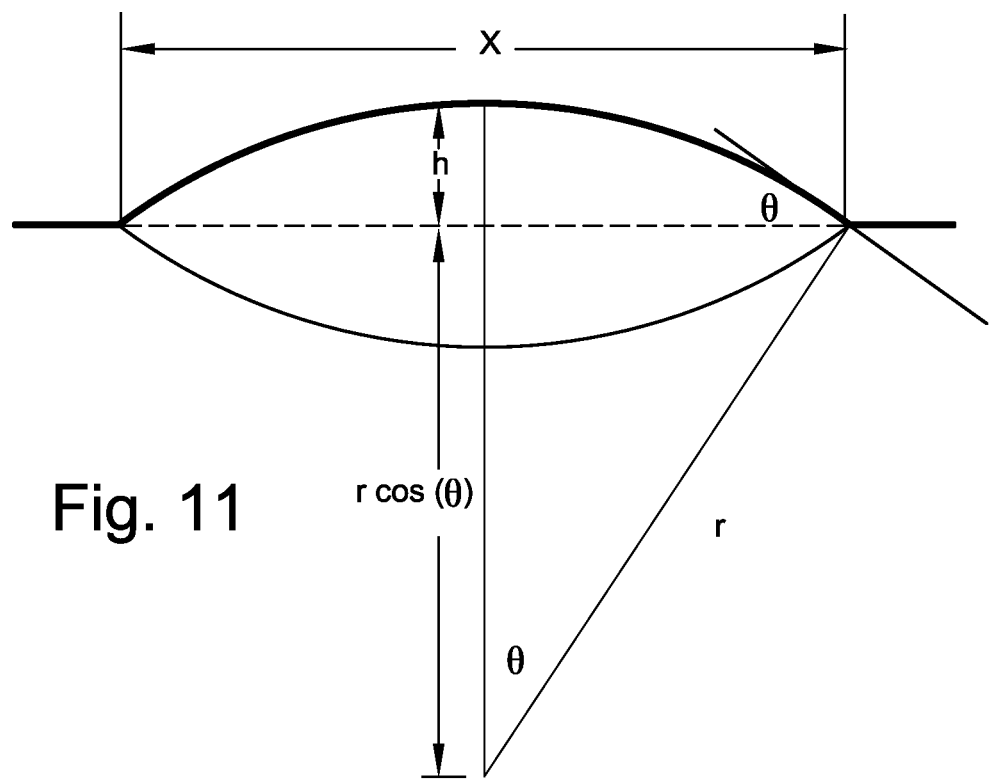

In the example of FIG. 10, the raviolus 145 has a width W and an inflated height 2h. The concertina sides are assumed to exert negligible force and are not included in the calculations. The force in the strap is f. In FIG. 10, the raviolus 145 is sliced in half transversely, and a pair of rigid plates, one of which is shown above as reference number 155, are attached to the cut line. The two plates are connected by a rigid rod 160. The force in the rigid rod 160 is also f.

Let the axial surface tension (force per unit length) in the top strap be t. Because the assembly does not move with time, the forces acting on the visible plate 155 must sum to zero. These forces comprise 2tW acting to the left, 2pWh acting to the right, and f in the rigid rod 160 acting to the right:

$$2tW = f + 2pWh \qquad (\text{eqn 1})$$

If there were no tension in the straps, for p>0, then the top and bottom surfaces of the raviolus 145 would together form a cylinder (θ=π/2). When the strap 25 is under tension, the surface becomes two incomplete symmetrical segments of a cylinder of radius r, as shown in cross section in FIG. 11.

The line where the two surfaces meet the strap is under equilibrium, i.e., has no net force on it. Because the surface of the raviolus 145 beyond the attachment point is irrelevant, the universe beyond the attachment point can be replaced with the remainder of a cylinder of radius r.

The cross section of the top or bottom surface is an arc of a circle, radius r, and subtending an angle 2θ at the center of the circle.

Figure 12:
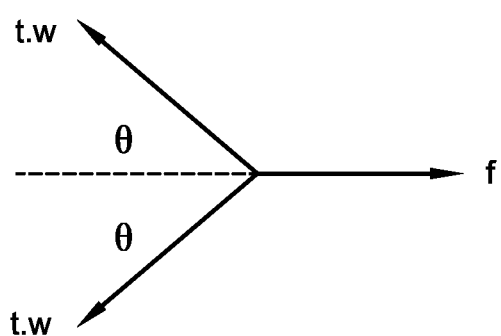

From simple geometry, the angle between the top or bottom surface of the raviolus 145 and the continuation of the strap is also θ, as shown in FIG. 12. Therefore, since the net force at the junction is zero, we have:

$$f = 2wt \cos(\theta) \qquad (\text{eqn 2})$$

A further constraint obvious from FIG. 12 is:

$$h = r(1 - \cos(\theta)) \qquad (\text{eqn 3})$$

Finally, if the raviolus 145 has a flattened length (distance between straps) of L, then the circumference of the arc is given by:

$$L = 2r\theta \qquad (\text{eqn 4})$$

Accordingly, there are four simultaneous equations, five unknowns p, h, t, f, and θ, and the constants W and L. Solving for f:

$$f = pWL \cos(\theta)/\theta \quad (0 < \theta < \pi/2) \qquad (\text{eqn 5})$$

Note the following special features:

(i) If the raviolus is flattened, i.e., θ→0, then any positive pressure generates infinite force.

(ii) If θ=π/2, i.e., the raviolus is cylindrical, then f is zero for all p. Ignoring the behaviour of the concertina sides, W and L play an equal role in force generation. Doubling either will double the force.

The force generated varies with the length of the raviolus 145. From FIG. 11, it can be seen that the distance x between the ends of the raviolus is given by:

$$x = 2r \sin(\theta) \quad \text{(eqn 6)}$$

and substituting r from equation 4 gives:

$$x = L \sin(\theta)/\theta \quad \text{(eqn 7)}$$

Recall that:

$$f = pWL \cos(\theta)/\theta \quad \text{(eqn 5)}$$

Table 1 was plotted using the above equations. Column 2 of Table 1 shows the length "x" of the raviolus (see FIG. 11), as a fraction of the resting length L, for various angles $\theta$. Column 3 shows the force "f" generated (see FIG. 10) as a fraction of the product of pressure p, width W, and resting length L.

TABLE 1

| $\theta$ (degrees) | $x/L = \sin(\theta)/\theta$ | $f/p\ WL = \cos(\theta)/\theta$ |
|---|---|---|
| 0 | 1.00 | infinite |
| 10 | 0.995 | 5.64 |
| 20 | 0.980 | 2.69 |
| 30 | 0.955 | 1.65 |
| 40 | 0.921 | 1.10 |
| 50 | 0.878 | 0.737 |
| 60 | 0.827 | 0.478 |
| 70 | 0.769 | 0.280 |
| 80 | 0.705 | 0.124 |
| 90 | 0.637 | 0.000 |

Figure 13:
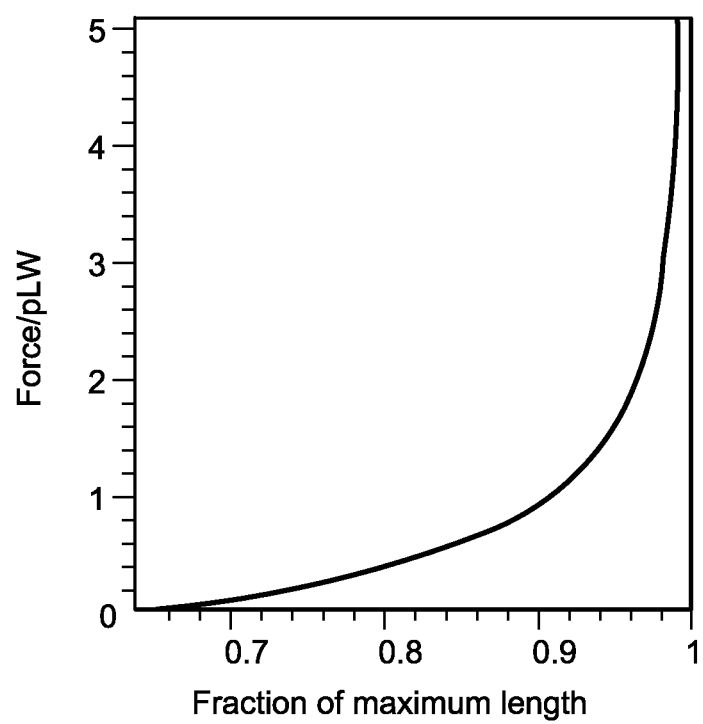
Figure 14A:
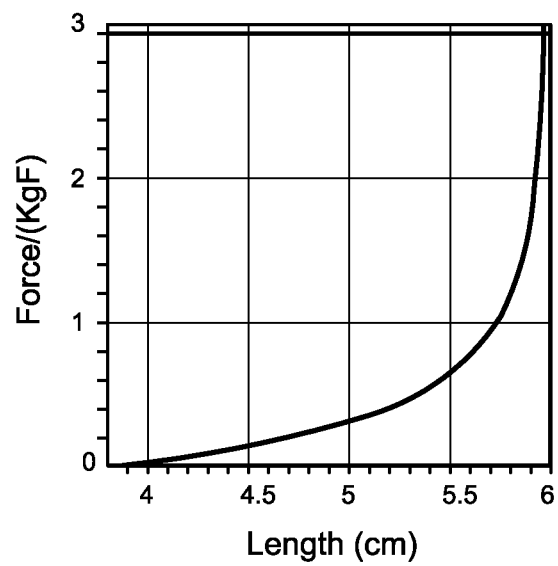
Figure 14B:
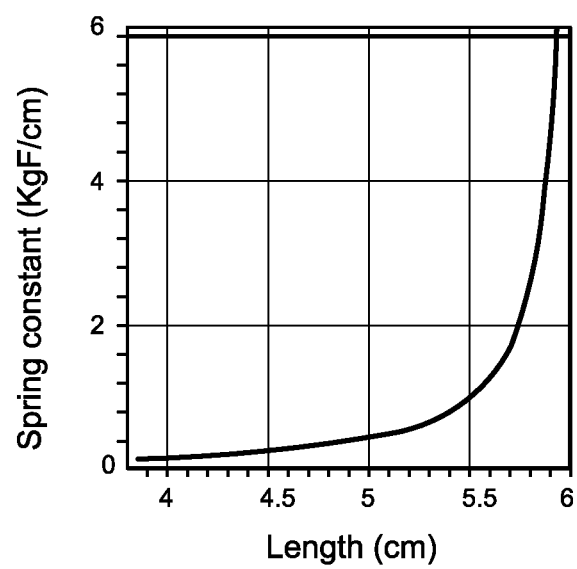

FIG. 13 plots the force f (as a fraction of pLW) against the length x (as a fraction of the resting length L).

Differentiating equations 5 and 7 with respect to $\theta$ gives:

$$df/d\theta = -pWL[\sin(\theta)/\theta + \cos(\theta)/\theta^2] \quad \text{(eqn 5a)}$$

$$dx/d\theta = L[\cos(\theta)/\theta - \sin(\theta)\theta^2] \quad \text{(eqn 7a)}$$

and dividing 5a by 7a gives (for $0 < \theta \leq \pi/2$):

$$df/dx = pW[\cos(\theta)/\theta + \sin(\theta)]/[\sin(\theta)/\theta - \cos(\theta)] \quad \text{(eqn 8a)}$$

In the limit as $\theta \to 0$ (empty raviolus), the denominator goes to unity, but the numerator goes to infinity, so the spring has infinite positive stiffness. For a fully inflated raviolus ($\theta = \pi/4$) the stiffness is $+4pW/\pi$. Table 2 adds the stiffness to the previous table.

TABLE 2

| $\theta$ (degrees) | Distance between straps (fraction of maximum) | Force generated (coefficient of pWL) | Stiffness (coefficient of pW) |
|---|---|---|---|
| 0 | 1.00 | infinite | infinite |
| 10 | 0.995 | 5.64 | 592 |
| 20 | 0.980 | 2.69 | 78 |
| 30 | 0.955 | 1.65 | 25 |
| 40 | 0.921 | 1.10 | 11 |
| 50 | 0.878 | 0.737 | 6.2 |
| 60 | 0.827 | 0.478 | 3.9 |
| 70 | 0.769 | 0.280 | 2.8 |
| 80 | 0.705 | 0.124 | 2.1 |
| 90 | 0.637 | 0.000 | 1.57 |

EXAMPLE

A practical raviolus might have:
W=5 cm=0.05 meters
L=6 cm=0.06 meters
P=20 $cmH_2O$=1960 $N/m^2 \sim$2,000 $N/m^2$ If the raviolus 145 is partially inflated and held between two rigid supports, then the strap tension increases linearly with pressure.

For any given geometry, the force generated is proportional to the resting length and breadth of the raviolus.

For any given pressure, the force generated is infinite when the raviolus is at its resting length, and falls off very rapidly thereafter.

As an example, a 6 cm long by 5 cm wide raviolus connected to 20 $cmH_2O$ generates about 0.633 KgF when it is shortened by 0.5 cm, 0.300 KgF when it is shortened by 1.0 cm, and 138 grams force when it is shortened by 1.5 cm.

An effect of this very strong dependence of force on length is that tightening the headstrap with a screw will permit any desired force to be generated at given pressure.

The mask assembly 15 is held onto the face at three points by two straps 25, 30. Take the mask assembly 15 to be an isosceles triangle of base 12 cm and height 12 cm, less two small triangles in the bottom corners of height 2 cm and base 2 cm. Thus the area of the mask is 70 $cm^2$.

At a pressure of 20 $cmH_2O$, the air pressure will be exerting 1400 grams force, and at 5 $cmH_2O$ it will be only 350 grams. Assume that in order to seal, it is necessary for the straps to exert a force 30% higher than this, or 1820 grams.

Per FIG. 15, assume that 1) the centroid C is about 4.5 cm up from the bottom of the mask, or 7.5 cm down from the top; 2) the bottom strap is attached around 3.5 cm up from the bottom of the mask, or 1 cm below the centroid; and 3) the top strap attaches to a long lever arm some 15 cm above the centroid.

Because the bottom strap attaches about 15 times closer to the centroid than the top strap, the bottom straps take 15/16 of the load, leaving only 100 grams to be borne by the top strap.

There is a 6 cm long by 5 cm wide raviolus in the top strap. It is connected to the mask by the tube 150. It will generate 100 grams force at 20 $cmH_2O$ when its length is reduced to 4.35 cm. Its stiffness at this length and pressure is 0.232 Kg force per cm.

Suppose the raviolus 145 is in series with a stretchy headgear strap of elastance $E_{STRAP}$. The free ends of the stretchy strap and raviolus are fixed. The elastance of the total system will be the elastance of the headgear plus the elastance of the raviolus.

For example, suppose the 5 cm wide by 6 cm long raviolus is mounted in series with a well-washed traditional ResMed® headstrap, with an elastance of 10 cm per KgF. The raviolus is at 20 $cmH_2O$, is 4.35 cm long, and exerting 0.1 Kg as before.

The spring constant of the raviolus under these conditions is 0.232 KgF/cm, so its elastance is 4.3 cm/Kg. Therefore total system has a (local) elastance of 14.3 cm/Kg. The elastance of the entire system is dominated by the traditional strap.

As another example, start with a 5 cm wide by 6 cm long raviolus, with pressure 20 $cmH_2O$. The length is therefore again $x_0$=4.35 cm, and generating a force of $f_0$=100 grams. The raviolus is again in series with a strap of elastance 0.1 Kg/cm, i.e., spring constant Kstrap=10 Kg/cm. The next step is to determine what happens when the pressure is reduced to 5 cm $H_2O$.

The equation for the force generated by the stretchy strap in terms of the length x of the raviolus will be:

$$\text{fstrap} = f_0 - \text{Kstrap}(x - x_0)$$

Figures 15A, 15B:
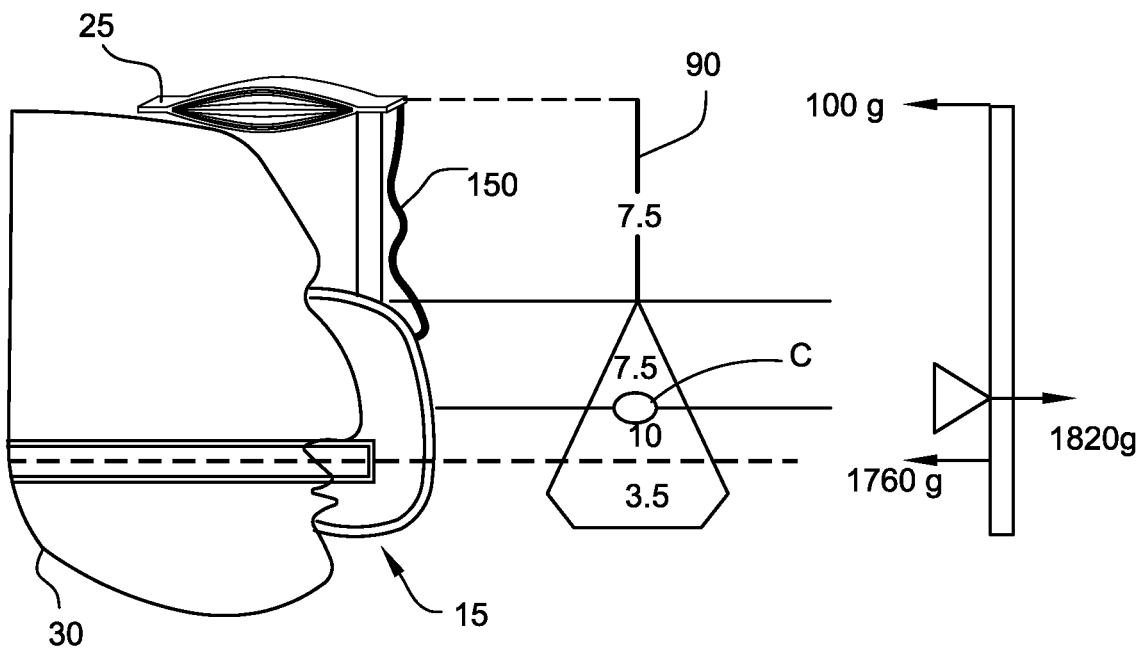
Figure 15C:
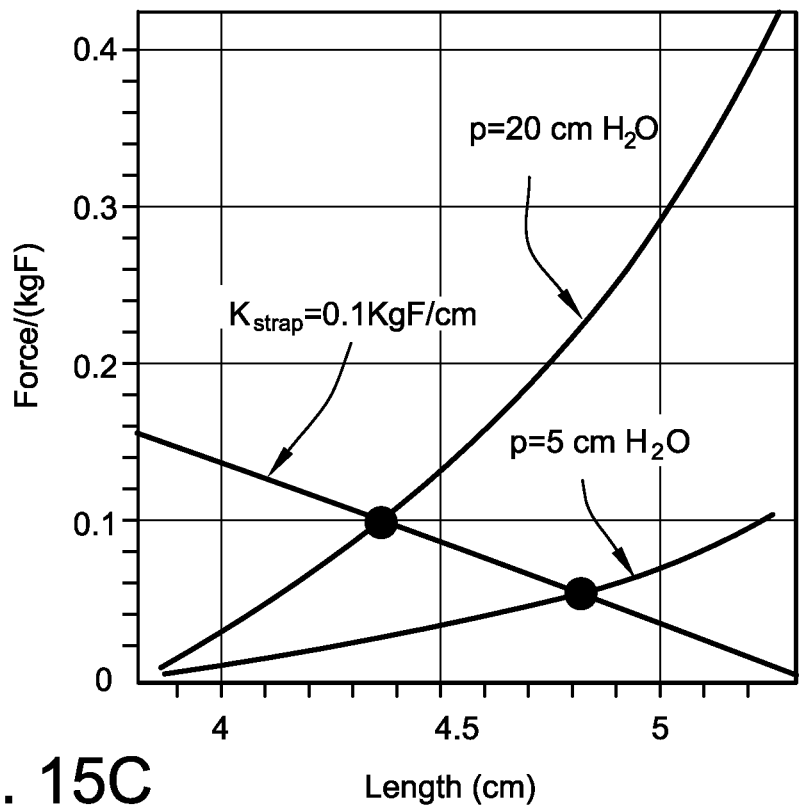

Plotting this on the graph for force generated by the raviolus at 20 cmH$_2$O and 5 cmH$_2$O, we obtain FIG. 15A.

The headgear will shrink, causing the raviolus to lengthen from 4.35 cm to about 4.8 cm, and instead of the tension in the strap reducing from 0.1 Kg to 0.05 Kg as desired, it will decrease to only about 0.55 Kg.

With no raviolus, the unnecessary strap tension to be borne by the bridge of the nose would be 75 grams. With a substantially inextensible or rigid headstrap, the raviolus, correctly adjusted, would reduce this to zero. But with a very sloppy headstrap, the unnecessary strap tension would be 45 grams, or a bit over half of what it would be with no raviolus.

2. Second Embodiment

FIGS. 16-35 illustrate another embodiment of the present invention.

Figure 16:
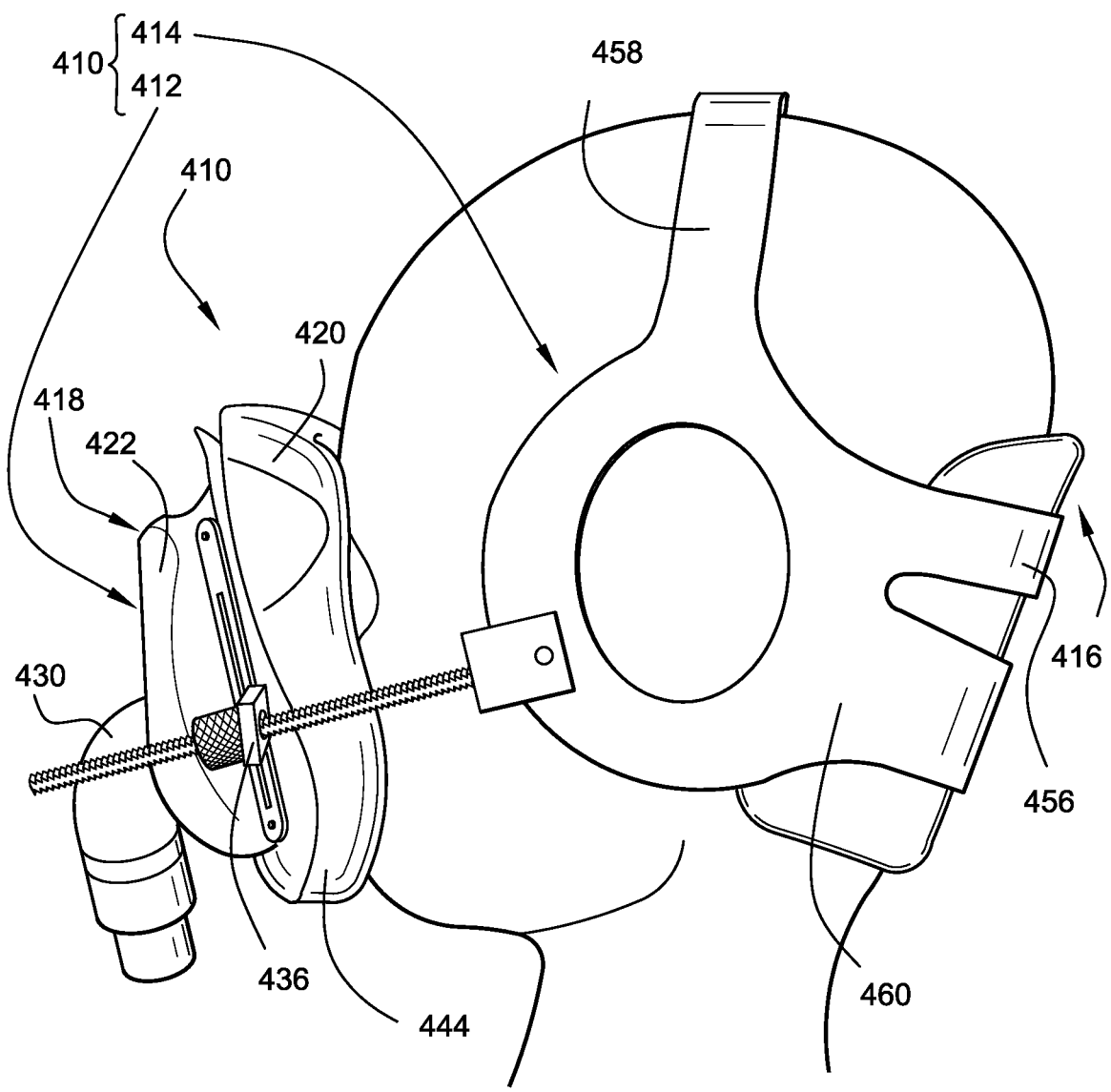
FIGS. 16-35 illustrate an alternative embodiment of the invention.
Figure 17:
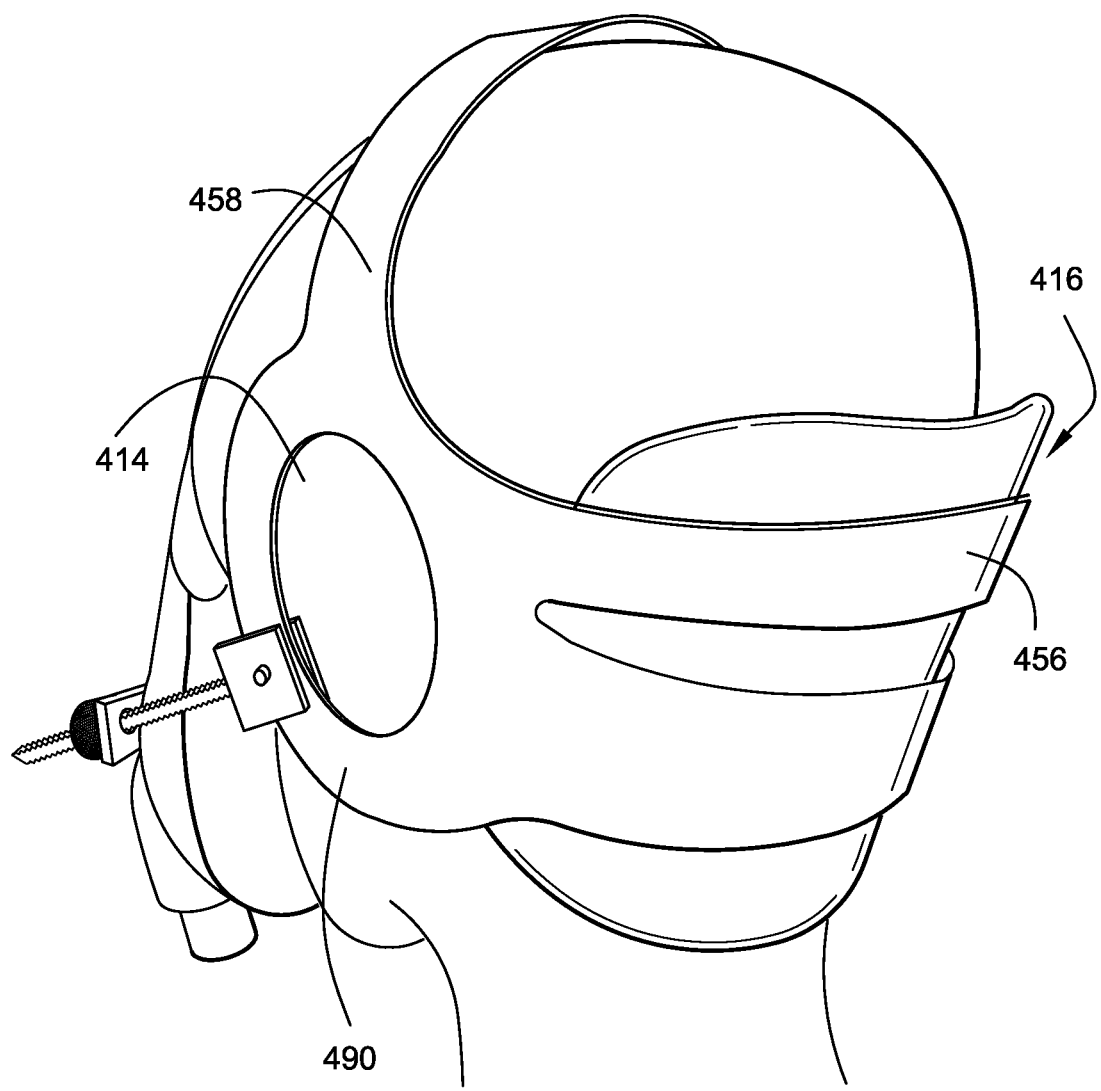
Figure 18:
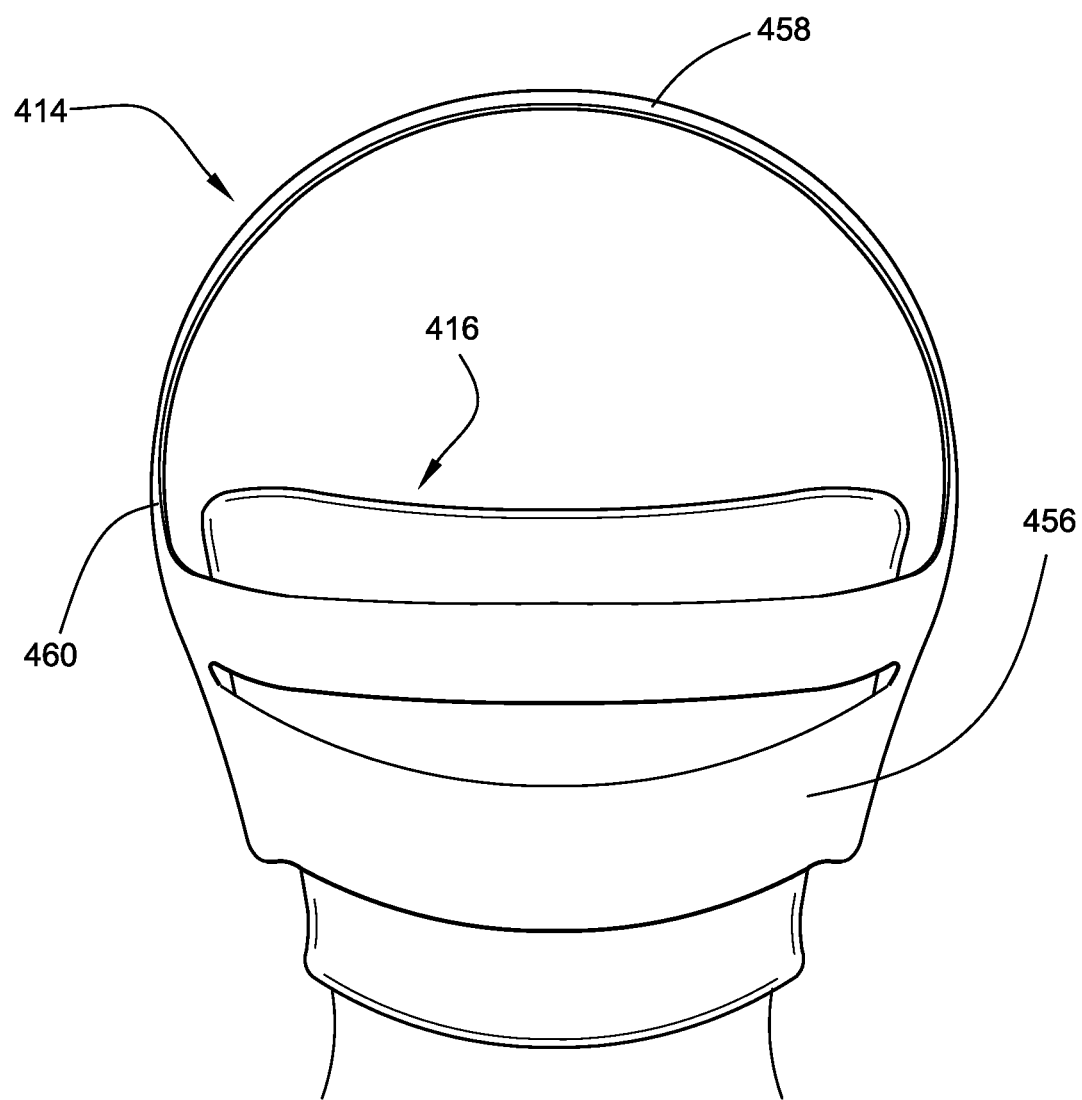

A mask and headgear assembly, generally indicated at 410, is shown in FIGS. 16-18 as installed on a model of a head. The mask and headgear assembly 410 comprises a mask assembly 412, headgear 414, and an inflatable bladder which takes the form of an occipital pneumatic pillow 416 coupled to the headgear 414 to adjust the fit of the headgear 414.

Figure 27:
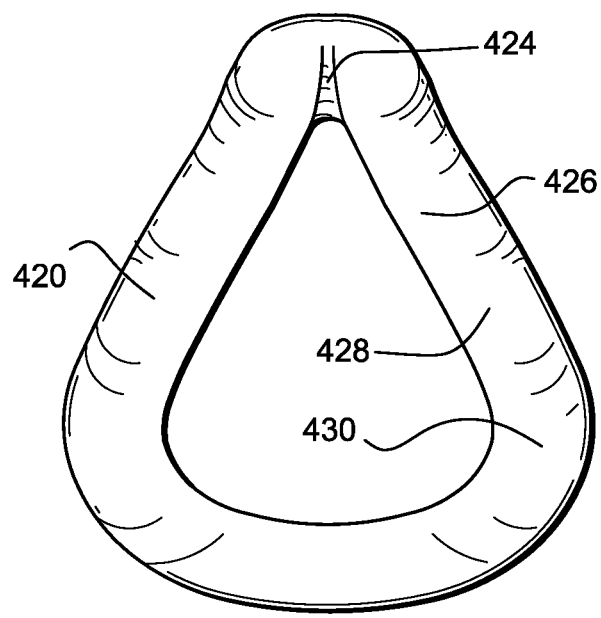
Figure 28:
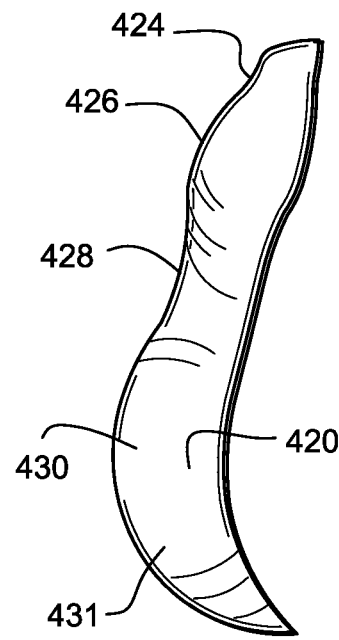
Figure 29:
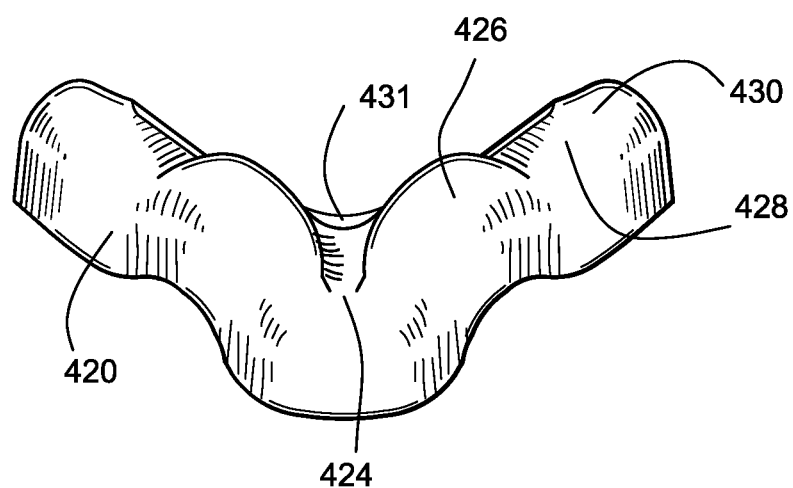
Figure 30:
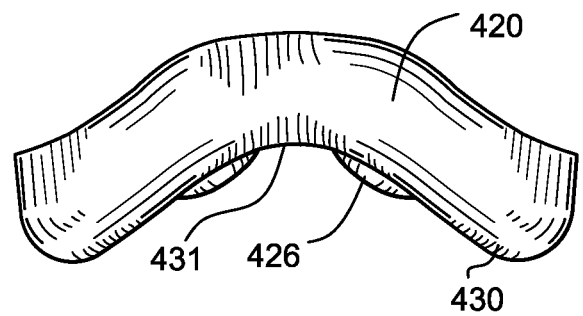
Figure 31:
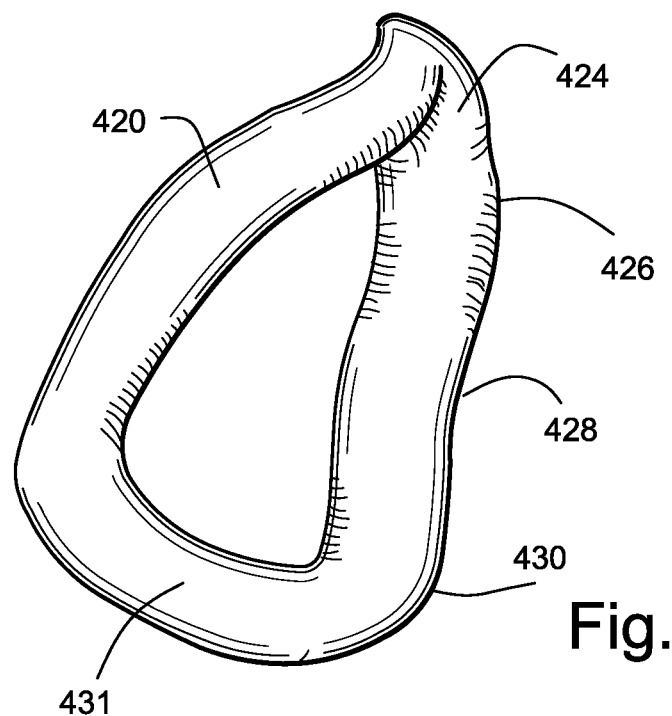

The mask assembly 412 includes a mask body assembly 418 and a mask frame 436 (which will be described in more detail below) that acts as a support or "skeleton" for the mask body assembly. The mask body assembly 418 has a generally triangular shape when viewed from the front, as shown in FIG. 27.

In one preferred form, the mask body assembly 418 comprises a face-contacting portion 420 and a body portion 422. The face-contacting portion 420 of the mask body assembly 418 is to provide a detailed fit without causing pain, discomfort or skin damage. In particular, the face-contacting portion 420 is designed to provide a seal around the bony parts of the nose. In order to avoid damage to the skin, it is preferable if no portion of the face-contacting portion 420 exerts an average pressure on the face that is greater than the average facial capillary blood pressure (typically about 25 mm Hg).

In general, the face-contacting portion 420 is contoured to pinch the sides of the nasal bone (above the nasal cartilage) and at the level of the inner canthus. The face-contacting portion 420 forms an inwardly-facing seal at the sides of the nasal bone. However, the face-contacting portion 420 is designed not to pinch the wings of the nose, either directly by pressing on the cartilages, or indirectly by pressing on soft tissues nearby. Furthermore, it is preferable that the face-contacting portion 420 not contact the eye, lashes, or tear duct mechanism at the inner canthus of the eye.

The face-contacting portion 420 of the mask body assembly 418 includes several major contoured features, which can be seen in the views of FIGS. 27-31. A notch 424 is provided to accommodate the bridge of the nose (nasion). A rise 426 is provided to fit the frontal process of the maxilla bone. A second notch 428 is provided to accommodate the cheek bone (i.e., maxillary process of the zygomatic bone). Additionally, a second rise 430 is provided to fit the jowl, and a third notch 431 is provided to accommodate the mandibular arch.

In one preferred form, the face-contacting portion 420 is constructed of a polyurethane foam covered by a silicone "skin" or sheet. It is preferable if the silicone material is the softest (i.e., lowest durometer value) material that can be made without a tacky or peeling character. Typically, the silicone skin would be adhesively bonded to the foam to prevent wrinkling of the skin relative to the foam.

The body portion 422 of the mask body assembly 418 supports the elbow 430, anti-asphyxia valve, and vent. It permits relatively free distortion or bending of the mask body assembly 418 relative to the frame 436 of the mask assembly 412, and also acts as a locating and constraining mechanism to prevent the frame 436 from sliding out of place. The mask body assembly 418 is shown in the plan view of FIG. 33A and in cross-section in FIG. 33B. In one preferred form, the body portion 422 is silicone, is co-molded with the face-contacting portion 420, and is contiguous with the face-contacting portion 422.

Figure 21:
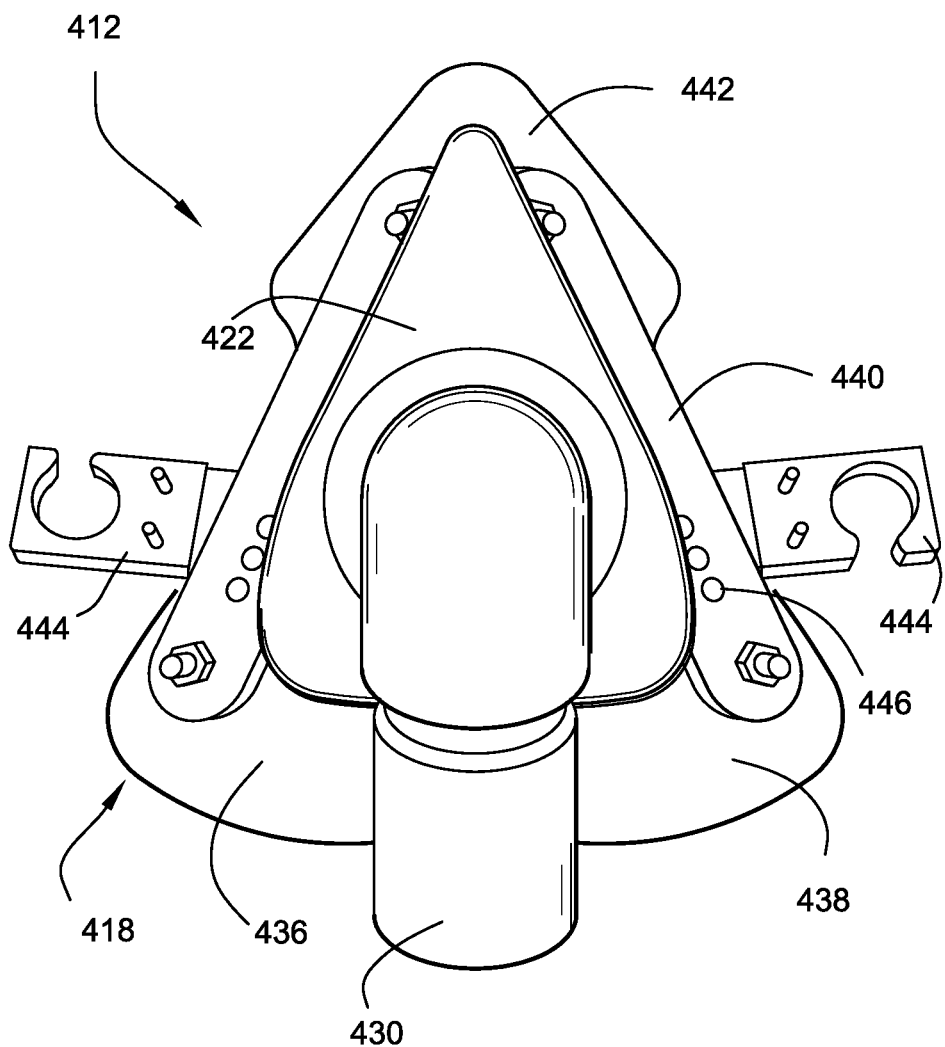
Figure 32:
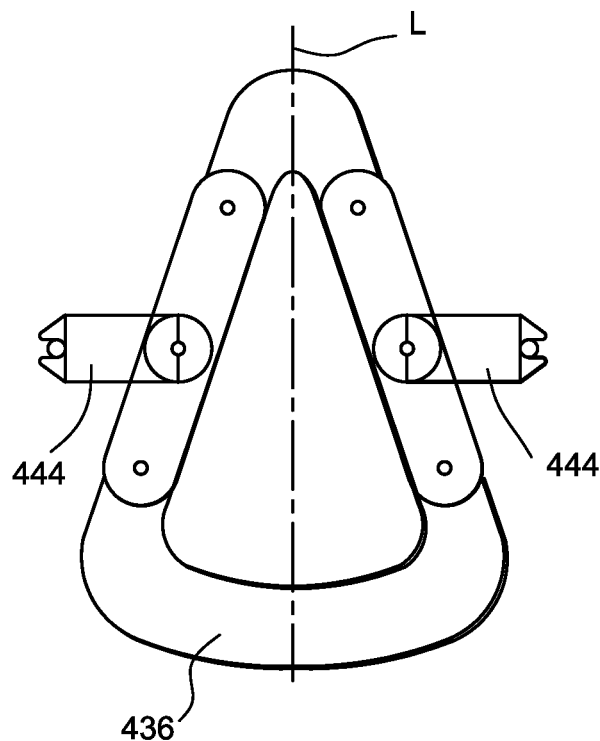
Figure 33A:
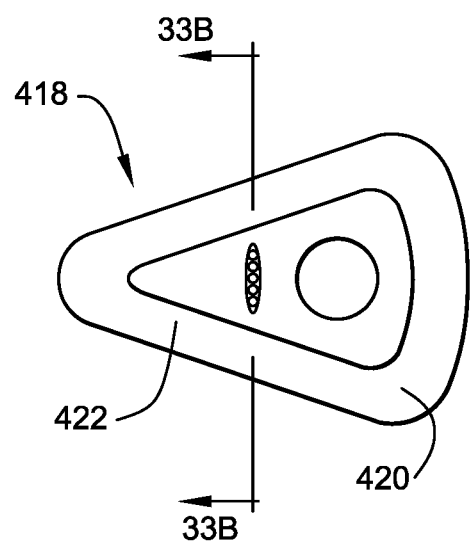
Figure 33B:
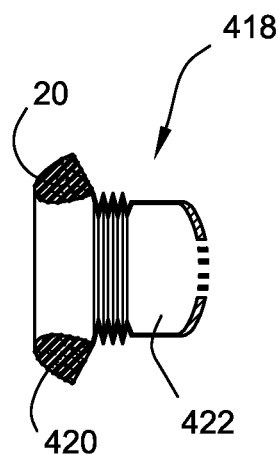
Figure 35:
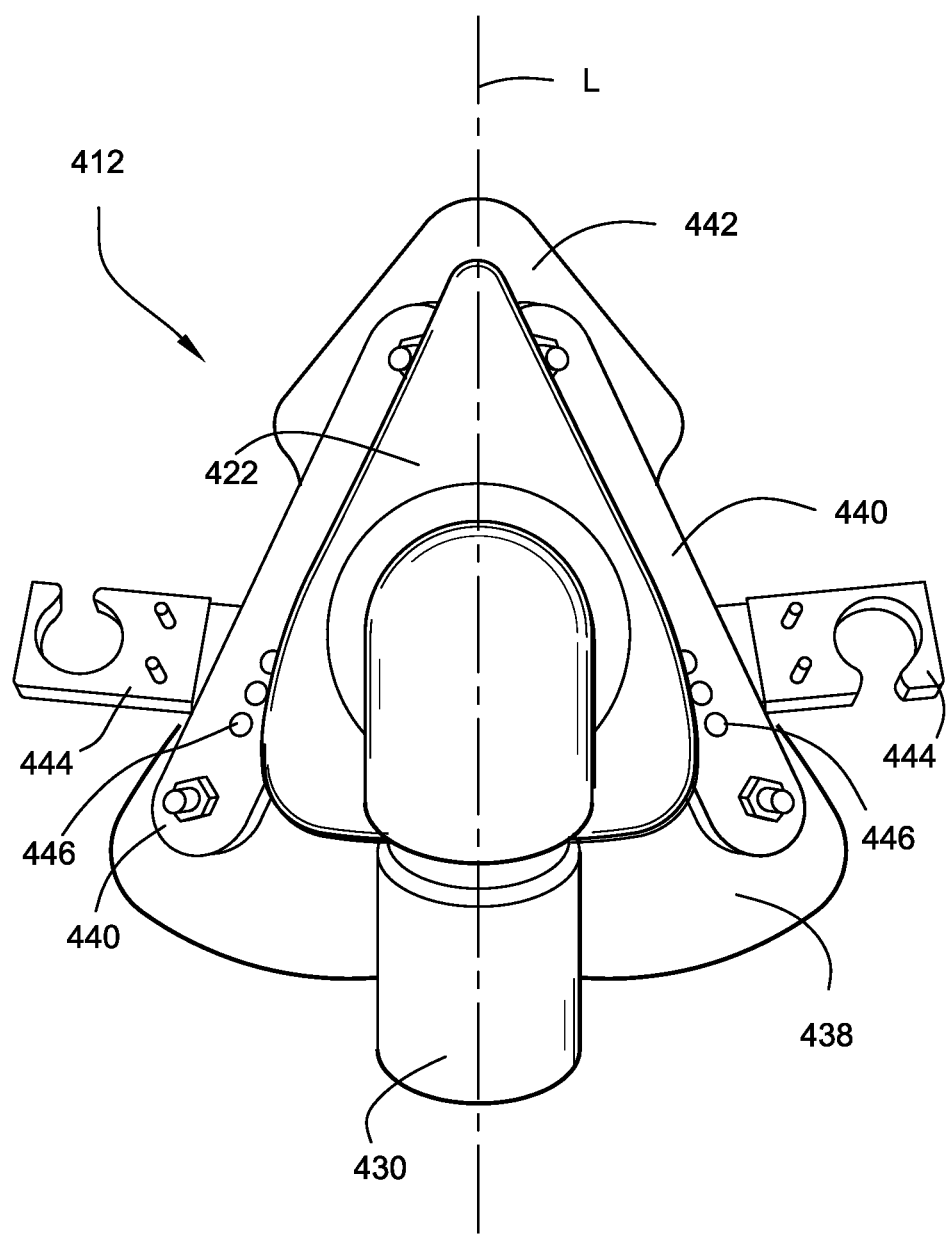

The mask assembly 412 includes a pressure plate or frame 436 which transmits the forces from the headgear to the cushion. As best shown in FIG. 21, the frame 436 is generally triangular in shape and comprises a base 438, side 440 and apex portions 442. The frame 436 is resiliently flexible, allowing the frame 436 to wrap around the jaw and nose of a patient. The base 438 and apex 442 portions of the frame 436 are generally constructed so as to be more flexible than the comparatively rigid side portions 440. The apex and base portions 442, 438 define a longitudinal axis L about which the frame 436 can resiliently flex, as shown in FIGS. 32 and 35. The resilient flexibility of the frame 436 allows the mask assembly 412 to more precisely fit a wider range of facial shapes. For example, the same mask assembly 412 could be used on patients with a narrow angular face (the so-called crocodile shape) as those with a wider flatter face (the so-called panda shape).

The base portion 438 of the frame 436 is generally "C" or crescent shaped. The apex portion 442 is generally boomerang or chevron shaped.

The flexible apex 442 and base 438 portions may be constructed from 1 mm polypropylene sheet approximately 2 cm wide. Each side portion 440 can be constructed from a pair of similarly shaped pieces of aluminum 100 mm×20 mm×1 mm. The frame 436 can be riveted together with 4 rivets, or joined by another known technique, such as adhesive bonding.

The frame 436, which is shown in isolation in the view of FIG. 32, includes a forked bracket 444 mounted on each side portion 440. Each bracket 444 is constructed of aluminum or another substantially rigid material. There are a series of holes 446 along the length of the side portions 440 which are adapted to receive a bolt to thereby secure the bracket 444. The angle of the bracket 444 with respect to the side portion 440 is adjustable by loosening the bolt, adjusting the angle, and tightening the bolt. The position of the bracket 444 along the side portion can be adjusted by securing within a different hole. Both brackets 444 need not be mounted in the same relative position along the side portions 440. In this way, some allowance can be made for any asymmetry in a patient's face. One bracket 444 is secured to each side portion. The bracket 444 is adapted to receive and engage the nut 448 of the threaded arm 450 of the headgear 414.

In addition, the frame 436 may include a wedge shaped spacer. In use, the spacer is operatively secured between the side 440 and/or apex 442 portions and the face-contacting portion 420 of the mask body assembly 418. The spacer is 1-2 cm thick at the top tapering to zero about half way down the mask. In addition, the wedge tapers to zero thickness from outside to inside. The wedge is constructed from a generally incompressible material. The wedge provides additional force to the top of the mask body assembly 418 to assist in sealing. In addition, the wedge pinches the mask body assembly 418 at the sides of the nasal bones, pressing harder on the outside edge of the mask body assembly 418 than on the inside.

The headgear 414 comprises a strap assembly 452, the occipital pneumatic pillow 416, or other active adjustable tensioning element, and the pair of threaded arms 450 that connect with the mask assembly 412. In general, the headgear 414 is constructed and arranged so that the force vector from the mask assembly 412 to headgear 414 which originates at the pneumatic center of the mask assembly 412 should pass through a point midway between the right and left external auditory meatus.

Figure 22:
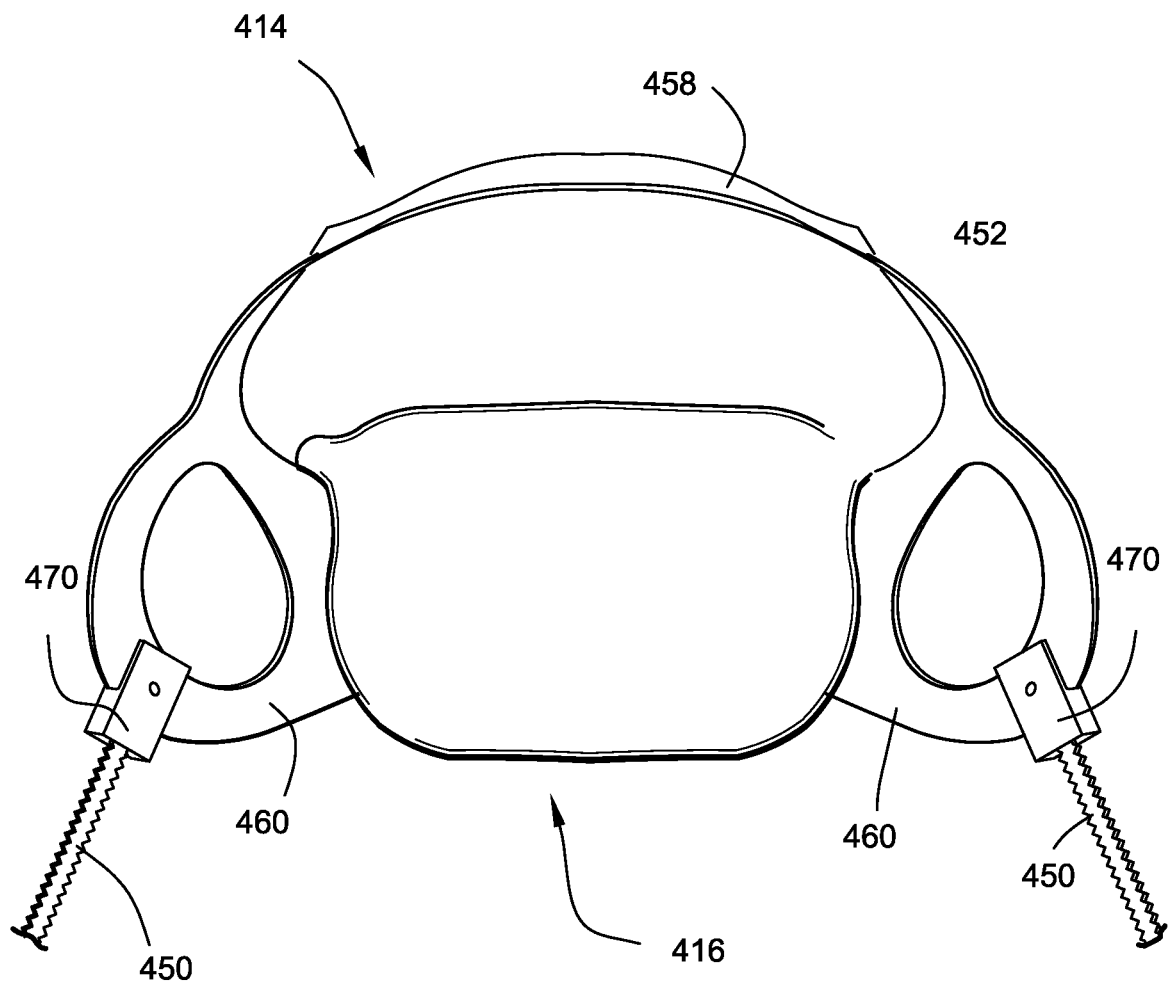
Figure 34:
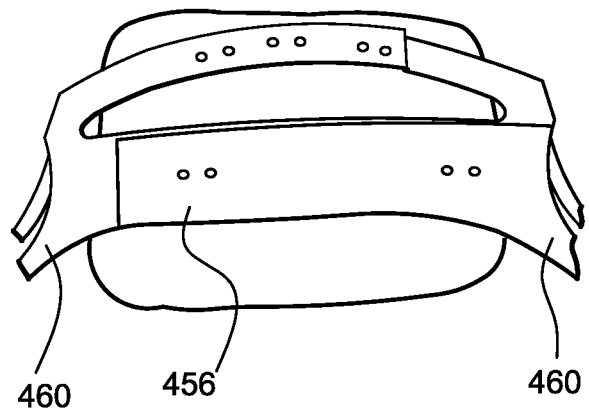

As shown best in FIGS. 22 and 34, the strap assembly 452 comprises a sub-occipital strap 456, a coronal (crown) strap 458, and a pair of ear pieces 460. In this embodiment, the straps 456, 458, 460 are ends of a single-piece headgear assembly, but in other embodiments of the invention, they may be unitary straps, optionally connected together at appropriate points. The straps 456, 458, 460 may be constructed from a flexible but generally inextensible plastic material, such as 1 mm polypropylene sheet, optionally covered on one or both sides with layers of foam, felt, or other cushioning material to increase comfort. Because they are formed of a flexible but inextensible material, the straps 56, 58, 60 can conform to the shape of a patient's head, but they would not generally extend more than 1-2 mm when subject to 2 KgF tension.

The sub-occipital strap 456 passes under the occiput but above the nuchal muscles and is approximately 4 cm in width. The crown strap 458 passes over the crown of the patient's head and is approximately 2 cm in width. The ear pieces 460 may be constructed so as to partially or fully surround the ears. The ear pieces 460 may be constructed from an eliptical annulus of plastic material, generally 2 cm in width, and lined with skin contact grade felt, which should slightly overlap the annulus to prevent cutting into the root of an ear.

Figure 19:
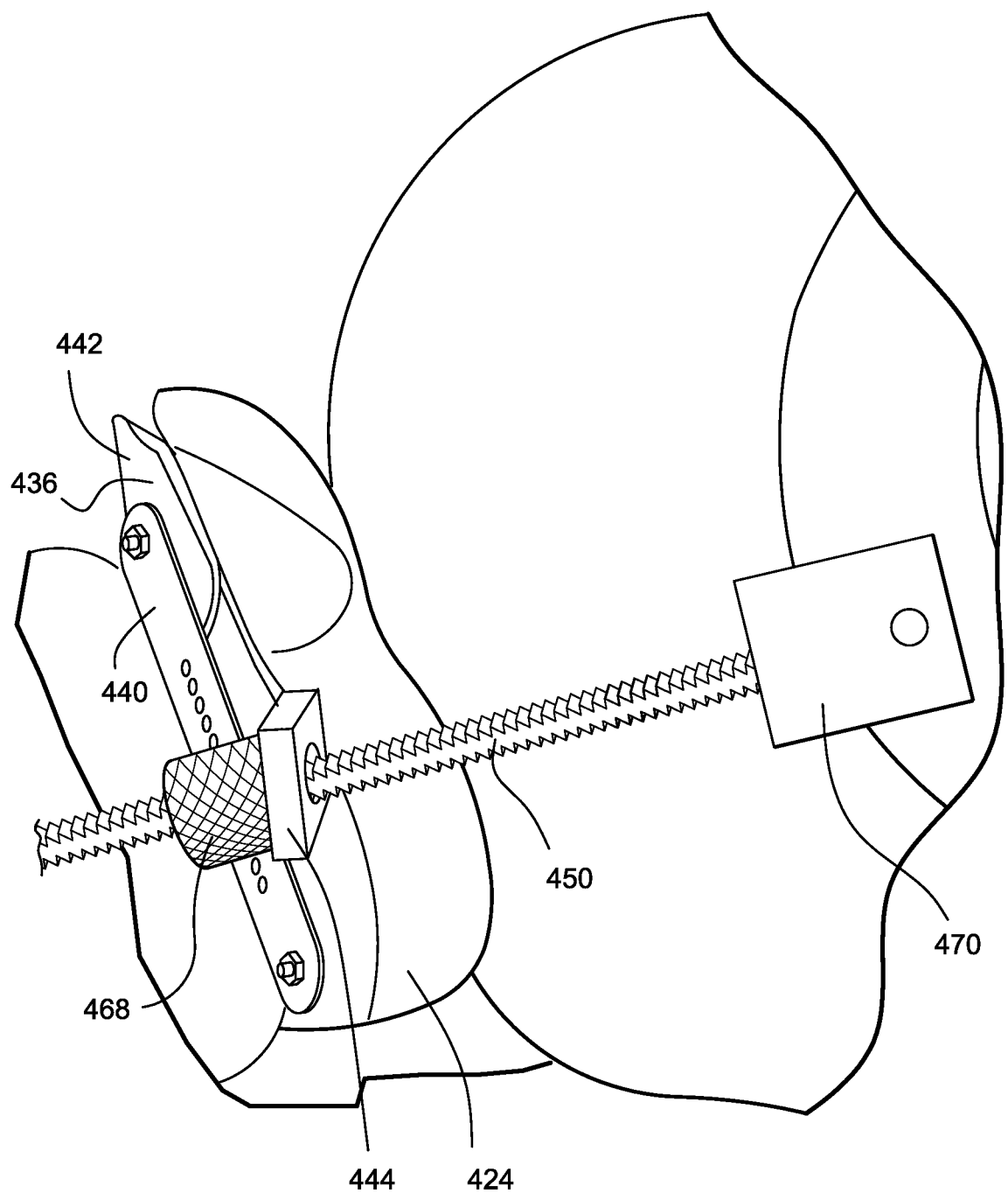
Figure 20:
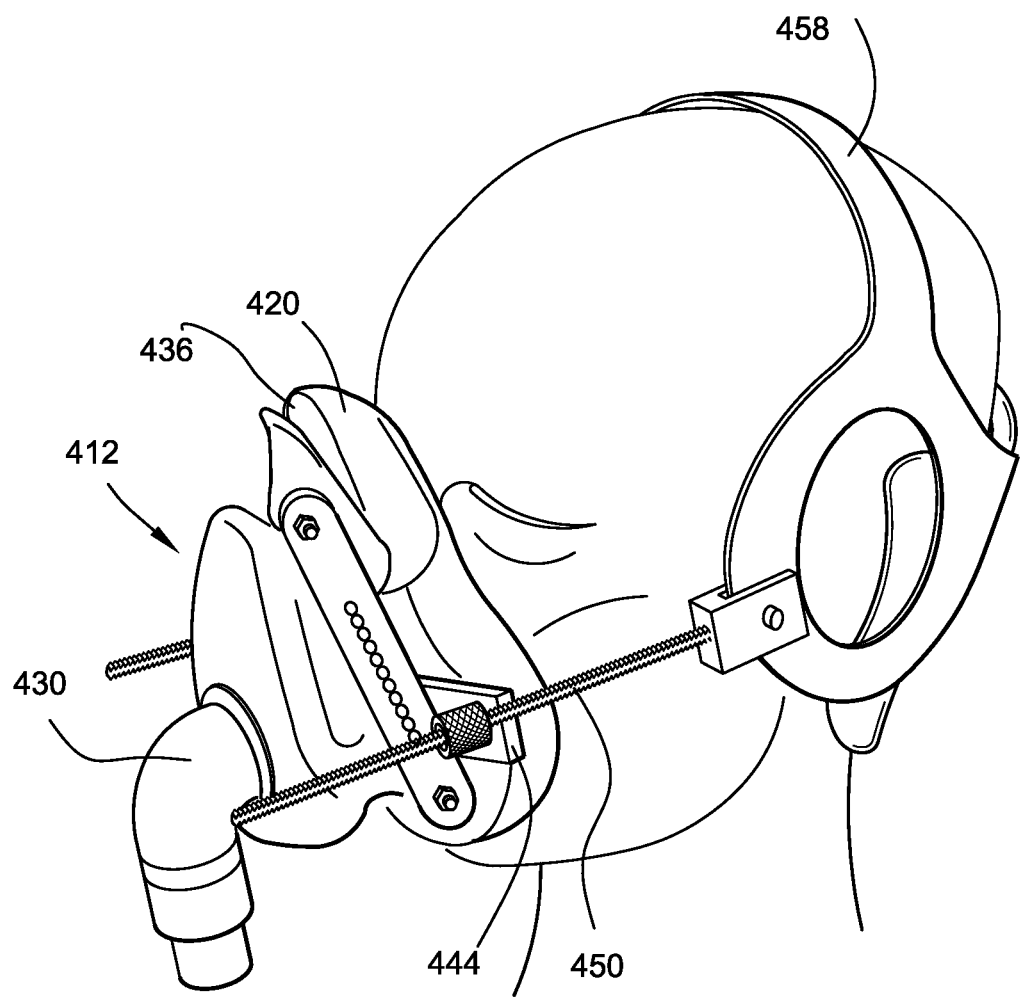
Figure 23:
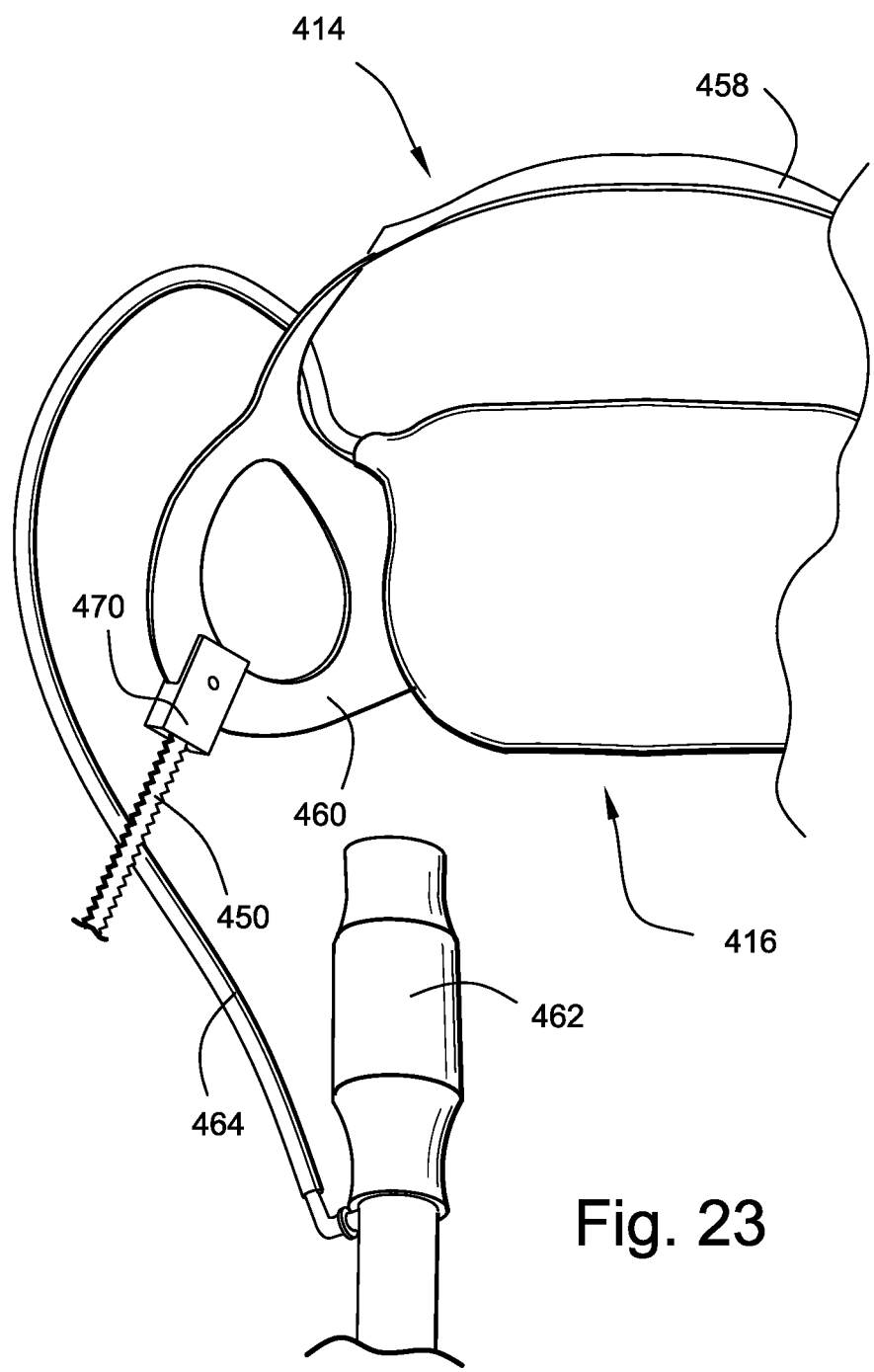
Figure 24:
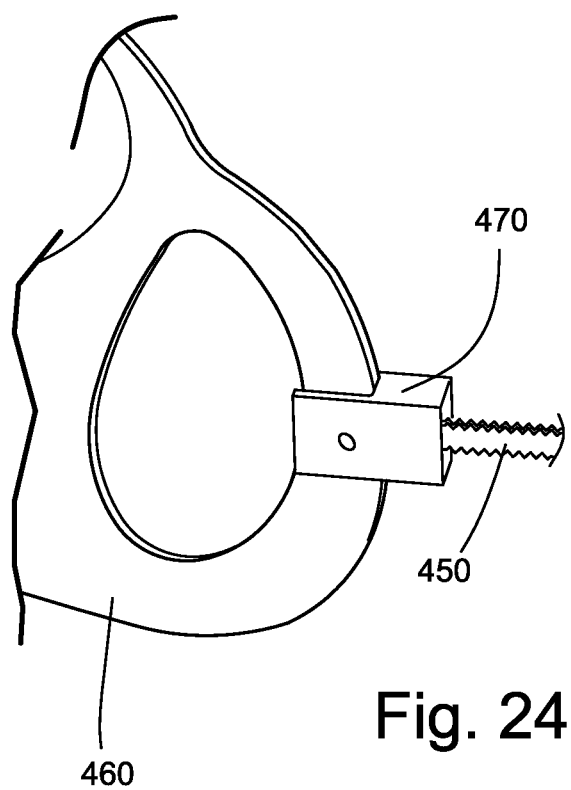
Figure 25:
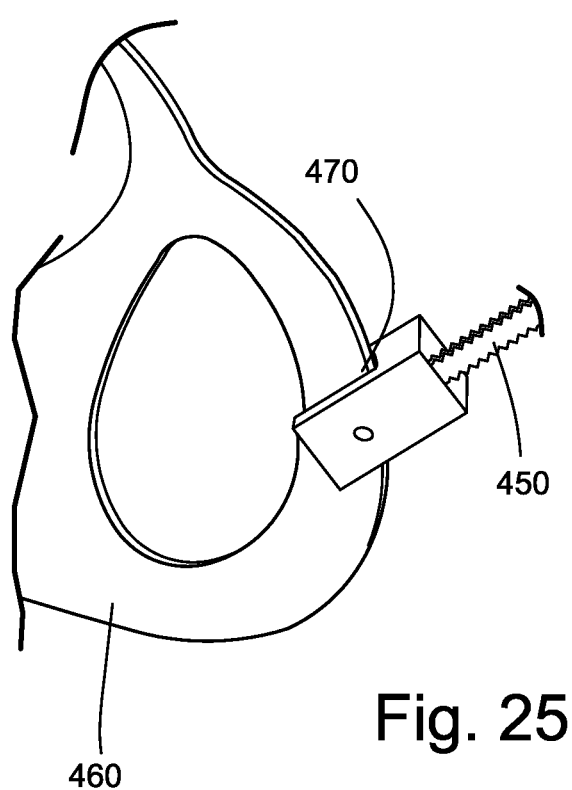
Figure 26:
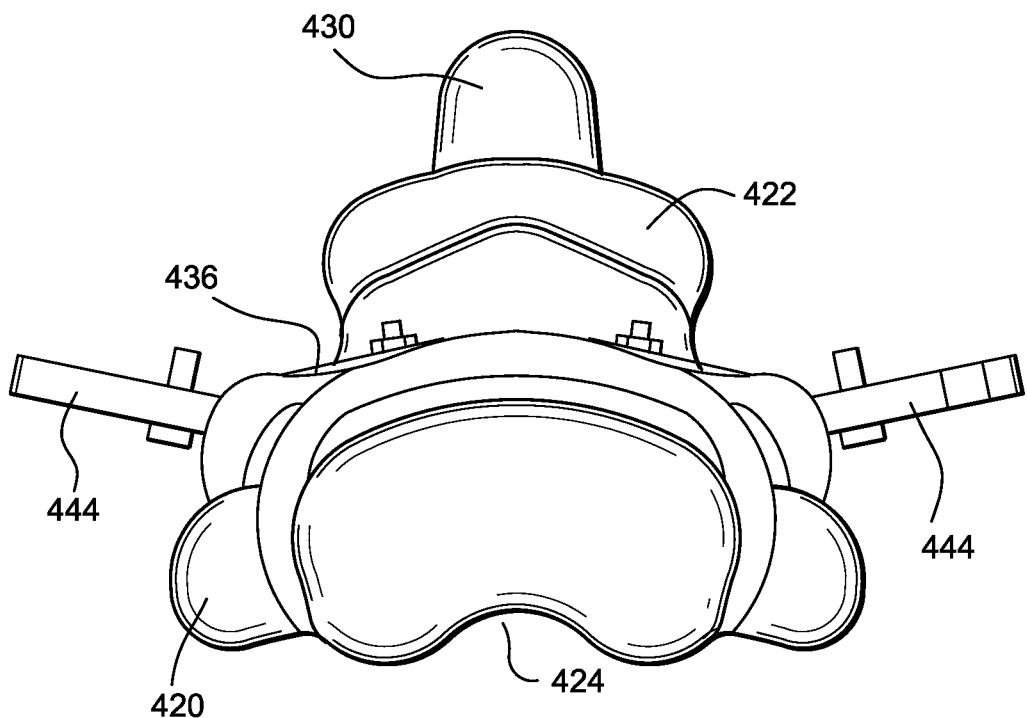

A pair of rigid threaded arms 450 extend from the ear pieces 460. In one embodiment, they are constructed from 5 mm threaded nylon rod. The arms 450 are arranged such that they are operationally proximate to the external auditory meatus and extend forwardly thereof in an approximately horizontal plane. There is a barrel nut or thumb-wheel 468 screwably mounted on and moveable along the length of each arm 450. Each nut or thumb-wheel 468 is adapted to releasably engage with the brackets 444 mounted on the mask frame 436, as shown in FIGS. 16, 17, 19 AND 20. The arms 450 are connected to the ear pieces 460 of the headgear 414 by a pivoting connector 470, as shown in FIGS. 19, 23 and 24. (First and second positions of the pivoting connector 470 are shown in FIGS. 24 and 25, respectively.) In this way, the relative angular position of the arms 450 is adjustable. By moving the nut 468 along the threaded arm, the tension within the frame 436 and headgear 414 can be precisely adjusted. This arrangement also provides a quick release mechanism. Since the frame 436 includes flexible base 438 and apex 442 portions, it will flex in accordance with the position of the nuts 468 along the arms 450 as they adjusted to find the most appropriate fit for the patient.

The inflatable occipital pneumatic pillow 416 is in force-transmitting relationship with the straps 456, 458, 460 and is operationally positioned under the strap assembly 452 and at the rear of the head, generally in the region of the occiput. The occipital pneumatic pillow 416 can be inflated and deflated. In one embodiment, as shown in FIG. 23, the occipital pneumatic pillow 416 is connected to an air delivery conduit 462 of the mask assembly 412 via a tube 464. In this way, the pressure in the occipital pneumatic pillow 416 is similar to the pressure in the mask assembly 412. When mask assembly 412 pressure increases, the occipital pneumatic pillow 416 is inflated, which results in a concurrent increase in headgear 414 tension and prevents the mask assembly 412 from lifting off the face and leaking. In this way movement of the mask assembly 412 during different mask pressures is dampened.

The occipital pneumatic pillow 416 is designed to have sufficient area ($A_{bladder}$) so that in conjunction with the pressure of air in the occipital pneumatic pillow 416 ($P_{bladder}$), it will counterbalance the force on the headgear straps 456, 458, 460 (i.e., the force on the straps 456, 458, 460 caused by the pressure in the mask assembly 412). Generally, the area of the occipital pneumatic pillow 416 should be sufficiently large so as to provide a force which exceeds the force caused by the mask, which is a product of the mask projected area ($A_{mask}$) and the mask pressure ($P_{mask}$). Hence:

$$A_{bladder} \times P_{bladder} = \Sigma \text{Forces applied to straps}$$

Furthermore, $$A_{bladder} \times P_{bladder} > A_{mask} \times P_{mask}$$

In one preferred form, the occipital pneumatic pillow 416 is approximately 11 cm×16 cm and has wall thicknesses in the range of about 1.5 mm to about 2.5 mm, with an overall deflated thickness of 3-5 mm.

In the embodiment described above, the pressure in the occipital pneumatic pillow 416 increases when the mask pressure increases. However, in other embodiments of the invention, the inflation and deflation of the occipital pneumatic pillow 416 could be controlled by parameters other than mask pressure. For example, a sensor could monitor leak in the mask assembly 412, e.g., by continuously monitoring flow in the flow generator connected to the mask assembly 412 and low-pass filtering to find the leak component of the flow. When leak is determined to be high, the occipital pneumatic pillow 416 would be caused to inflate. Conversely, when leak is determined to be low, the occipital pneumatic pillow 416 would be allowed to deflate. Controlling the occipital pneumatic pillow 416 pressure using a leak detection sensor would allow the headgear 414 to be maintained at the minimum amount of tension that would allow the mask assembly 412 to remain sealed against the face, and would help to reduce the user discomfort, skin damage, and other problems inherent in over tensioning the headgear 414.

Additionally, it may be desirable to use more than one occipital pneumatic pillow 416 in the headgear 414. If more than one occipital pneumatic pillow 416 is used, the occipital pneumatic pillows 416 could be placed in several locations around the headgear 414. Moreover, each of the multiple occipital pneumatic pillows 416 could be inflated and deflated independently of the others. That type of arrangement would make it easier to compensate for asymmetries in the patient's face, because tension could be applied in the headgear 414 locally and only where needed. Multiple occipital pneumatic pillows 416 may be caused to inflate and deflate as pressure in the mask assembly 412 increases and decreases, respectively, or they may be caused to inflate and deflate by a sensing and control system, based on measurements of leak flow.

Figure 82:
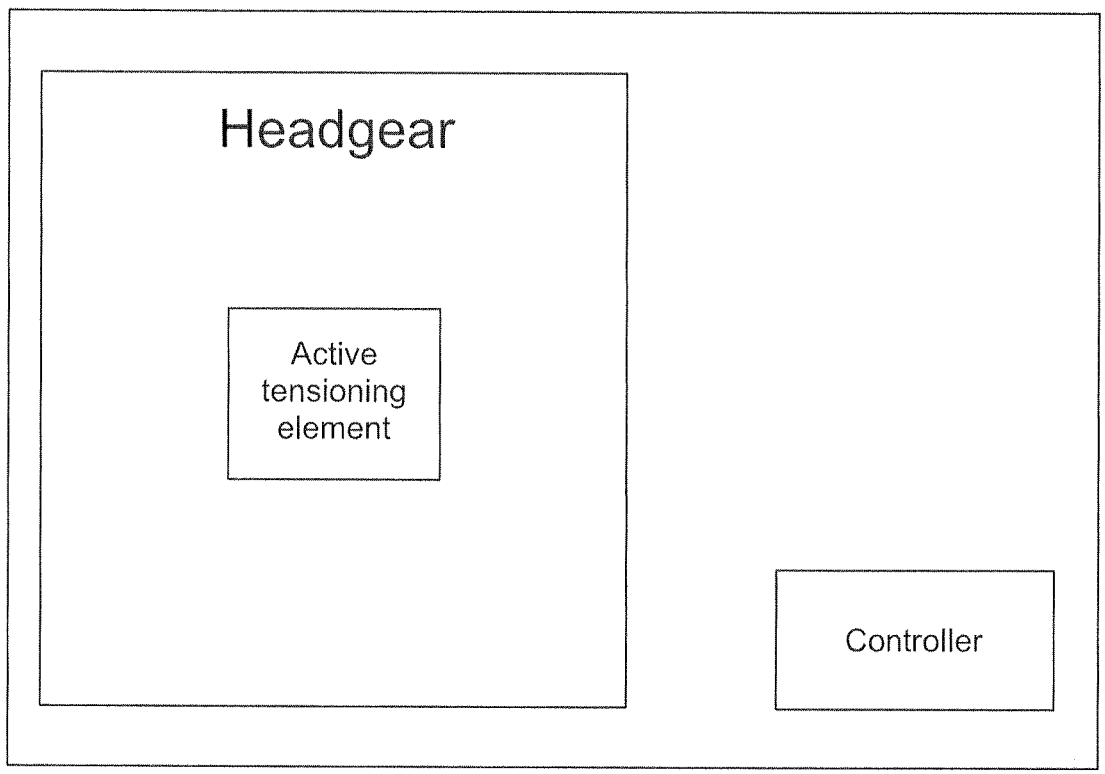
FIG. 82 is a schematic illustration of an aspect of the technology with an active tensioning element.
Figure 83:
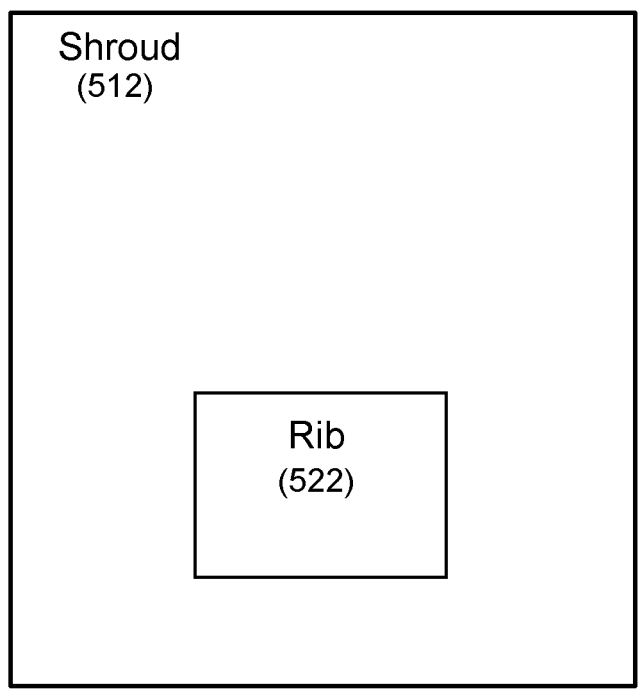
FIG. 83 is a schematic illustration of an aspect of a chassis with a rib.

In an alternative embodiment of the invention (as schematically shown in FIG. 82), shape memory alloy (SMA) wires, such as MUSCLE WIRES® (Mondo-Tronics, Inc., San Rafael, Calif., USA), which contract when electric current is applied, may be used as active tensioning elements. (Typically, the contractile response when electric current is applied is due to heating of the wire caused by the passage of the electric current through it.) If these types of elements are used to produce active tension adjustment, a separate controller would need to be provided to cause the wires to contract synchronously with increases in mask pressure.

Other suitable active tensioning elements include servo motors and "artificial muscles" created from biomimetic materials.

D. Algorithm

The occipital pneumatic pillow 416 according to the embodiment of FIG. 16, e.g., can be initially inflated to a pre-set tension. In one embodiment, a method for holding a mask sealingly against a patient's face may include: placing an occipital pneumatic pillow against the back of the head and/or neck; passing one or more straps over, through or as part of the occipital pneumatic pillow, the straps passing forward to attach to the mask; and inflating the occipital pneumatic pillow with a pressure $P_{bladder}$ which is an affine function of mask pressure $P_{mask}$:

$$P_{bladder} = P_0 + A_{mask} P_{mask}$$

where $P_0$ is a positive pressure sufficient to cause the mask to seal at the lowest intended usage pressure, and $A_{mask}$ is the lesser of the area of contact between the occipital pneumatic pillow and the straps posteriorly, and the area of contact between the occipital pneumatic pillow and the back of the head anteriorly.

In embodiments, the inflating of the occipital pneumatic pillow with a pressure which is an affine function of mask pressure comprises: measuring mask pressure with a pressure transducer, to produce a signal proportional to mask pressure; applying the signal to an amplifier with adjustable gain an offset; applying the output of the amplifier to a voltage controllable pressure source; inflating the occipital pneumatic pillow with gas from said pressure source; adjusting the offset so that the mask seals at the lowest required pressure; and adjusting the gain so that the mask seals at the highest required pressure.

In embodiments, if the signal $V_{pt}$ from the pressure transducer is $V_{pt} = K_{pt} P_{mask}$, the controllable pressure source produces a pressure $P_c = K_c V_c$, the projection in the posterior direction of the contact area of the mask with the face is $A_{mask}$, the projection in the anterior direction of the area of contact of the straps with the posterior surface of the occipital pneumatic pillow is $A_{bladder}$, and the force required to produce a seal at zero pressure is $F_0$, then the amplifier produces an output voltage:

$$V_{out} = F_0 / A_{bladder} + A_{mask} / A_{bladder} K_c / K_{pt} V_{in}.$$

In embodiments, inflating the occipital pneumatic pillow with a pressure which is an affine function of mask pressure may comprise: connecting the mask via a first hose to a first cylinder containing a first piston, the first piston in turn being connected via a linkage to a second piston in a second cylinder, the second cylinder being connected via a second hose to the occipital pneumatic pillow; and biasing said linkage so as to inflate the occipital pneumatic pillow sufficiently to cause the mask to seal at the lowest intended usage pressure.

In embodiments, bias may be provided by a spring and/or a weight.

An apparatus for holding a mask sealingly against a patient's face may include a first set of extensible straps, passing from the back of the head forwards to the mask, the straps being tightened sufficiently to hold said mask sealingly against the face at the lowest intended usage pressure; a second set of inextensible straps, again passing from the back of the head forwards to the mask, and lying over the first set; and an inflatable occipital pneumatic pillow placed at the back of the head, between the first and second set of straps, said occipital pneumatic pillow being in pneumatic communication with the air in the mask.

In operation, the first, extensible set of straps provides a fixed, constant force, independent of mask pressure, and the occipital pneumatic pillow, acting via the second set of straps, provides a force which is a linear function of mask pressure. The two forces add together, to provide a force which is an affine function of mask pressure. The optimum arrangement will be approximately when the anterior projection of the smaller of the area of contact by the occipital pneumatic pillow onto the back of the head and the area of contact of the occipital pneumatic pillow onto the second set of straps is the same as the posterior projection of the area of contact of the mask on the face.

In another embodiment, an apparatus for holding a mask sealingly against a patient's face may include a set of rigid straps, passing from the back of the head forwards to the mask; a semi-rigid, springy occipital pneumatic pillow placed between said straps and the back of the head, the occipital pneumatic pillow having a non-zero internal separation between the anterior and posterior walls at atmospheric internal pressure; and a hose connecting the occipital pneumatic pillow to the mask.

The occipital pneumatic pillow may be conveniently constructed of an elastomeric material such as silicone, latex, or polyurethane. Its springiness may be adjusted by filling it with a springy material such as a foam of silicone, latex, polyurethane, and/or PVC, or with one or more internal or external springs. A comfortable internal spring can be created from a second, sealed air and/or fluid-filled elastomeric inner occipital pneumatic pillow, smaller than the outer occipital pneumatic pillow.

Optimally, the antero-posterior separation between the anterior and posterior walls of the occipital pneumatic pillow at atmospheric internal pressure should be about 2-4 cm, for preference 3 cm, to allow a reasonable range of neck movement without overly increasing or decreasing the strap force, and to allow for a considerable compression of the structures on the back of the head (hair, skin, fat, muscle), and of the mask cushion and facial tissues, as the mask pressure increases.

The combined stiffness of the occipital pneumatic pillow walls and any foam filling or springs should for preference be such that it produces a force sufficient to cause the mask to seal at all intended pressures when the straps are tightened to about mid-travel, or about 1.5 centimeters below the untensioned length. Typically the force will be of the order of 200-600 g, depending on the characteristics and fit of the mask.

As strap tension increases at higher mask pressures, the mask cushion and the tissues at the back of the head will be compressed. This will cause the occipital pneumatic pillow to expand. Since the occipital pneumatic pillow is preferably intentionally stiff, and has been compressed by tightening the straps below their loose length in order to provide the force $F_0$ required to seal at arbitrary low pressures, the springiness of the occipital pneumatic pillow will provide less and less force as the occipital pneumatic pillow expands. This loss of the initial spring recoil force should be compensated by using a occipital pneumatic pillow with an area $A_{bladder}$ which is suitably greater than the area of the mask $A_{mask}$.

When the occipital pneumatic pillow is under pressure, and acting against the back of the head anteriorly and against the straps posteriorly, there will be a portion with flat cross section in contact with the straps, and a curved portion on either side, not in contact with the straps. Only the area in contact with the straps, and specifically the anterior projection of this area, will be generating useful strap tension. In practice, for a typical sized full adult face mask, for example, an bladder with dimensions around 17 cm side to side, 11.5 cm top to bottom, and 3 cm thick is suitable. The projected area of contact with the straps will be about 15 cm side to side by 10 cm top to bottom, so that the bladder will act approximately like a piston of area 150 cm². Of course, these are examples only that can be modified according to preference and/or application.

Frame

A. Adjustable Frame

1. First Embodiment

Figure 36A:
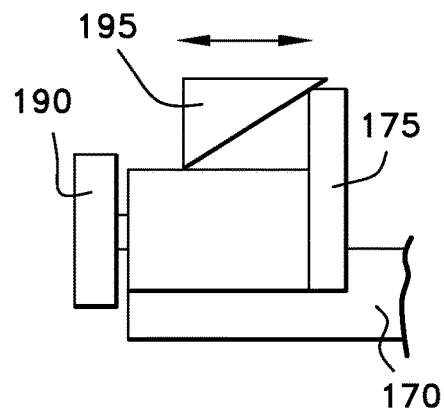
FIGS. 36-40B illustrate an embodiment of the present invention in which the sides of the patient's nose can be effectively sealed.
Figure 36:
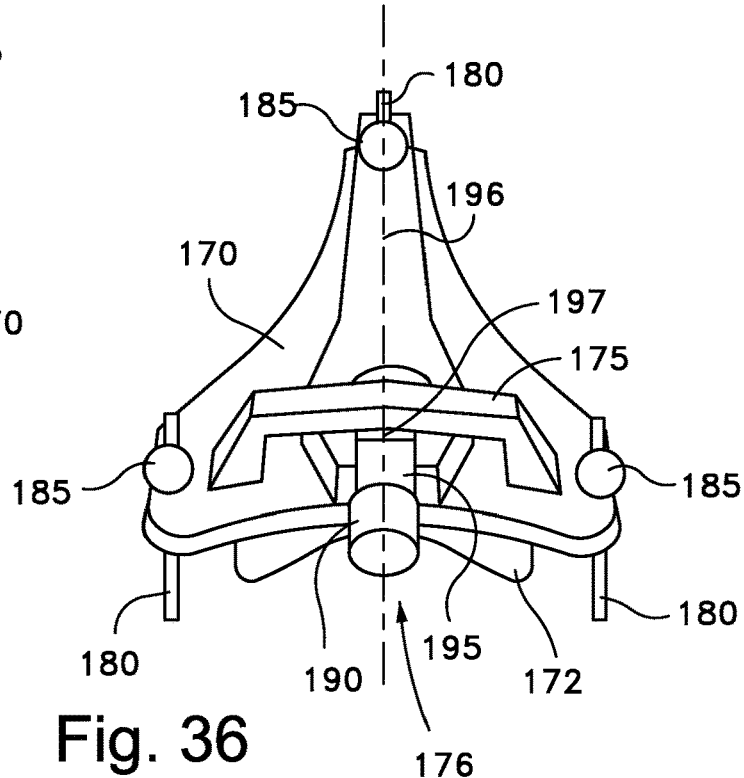

FIG. 36 represents an embodiment of the present invention including a frame 170 which is provided with a patient interface in the form of a cushion 172. The frame 170 is supported on the head of the patient using a plurality of straps 180, which may be made of substantially inextensible material as described above. Each strap 180 may include a threaded portion at an end thereof that is adapted to receive a nut 185 so that the patient can adjust the tension in the straps. A warping strap 175 made of substantially rigid material is provided to the frame 170.

An adjustment mechanism 176 is provided for additional adjustability of the frame 170. In particular, the adjustment mechanism 176 includes an adjustment screw 190 which can be rotated to effect translating movement of a wedge 195. The wedge 195 can be moved along an imaginary axis 196 that is aligned with the upper most head strap 180 provided at the apex of the frame 170. Rotation of the adjustment screw 190 causes movement of the wedge 195 against the inside surface of the warping strap 175. In an alternative shown in FIG. 36A, the wedge 195 may be provided to engage the outer surface of the warping strap 175. In either case, if the wedge 195 is moved upward toward the top of the frame 170, the top surface 197 of the wedge 195 is forced against the inside or outside surface of the warping strap 175, which causes the frame to bend about an axis which is substantially parallel to or coincident with the imaginary axis 196.

This bending causes the lateral portions of the frame 170 to push against the sides of the cushion 172, thereby imposing a pinching force on the sides of the patient's nose. The provision of adjustability in the lower part of the frame 170 allows the mask to more readily adapt to different types of nose features. Of course, the adjustability could be provided along the top or middle portions of the frame as well. The adjustability allows for the patient to set the desired contacting force for a given pressure, and the frame may flex, pivot or bend to accommodate changes in pressure so that the force applied to the face is substantially constant.

2. Second Embodiment

Figure 37:
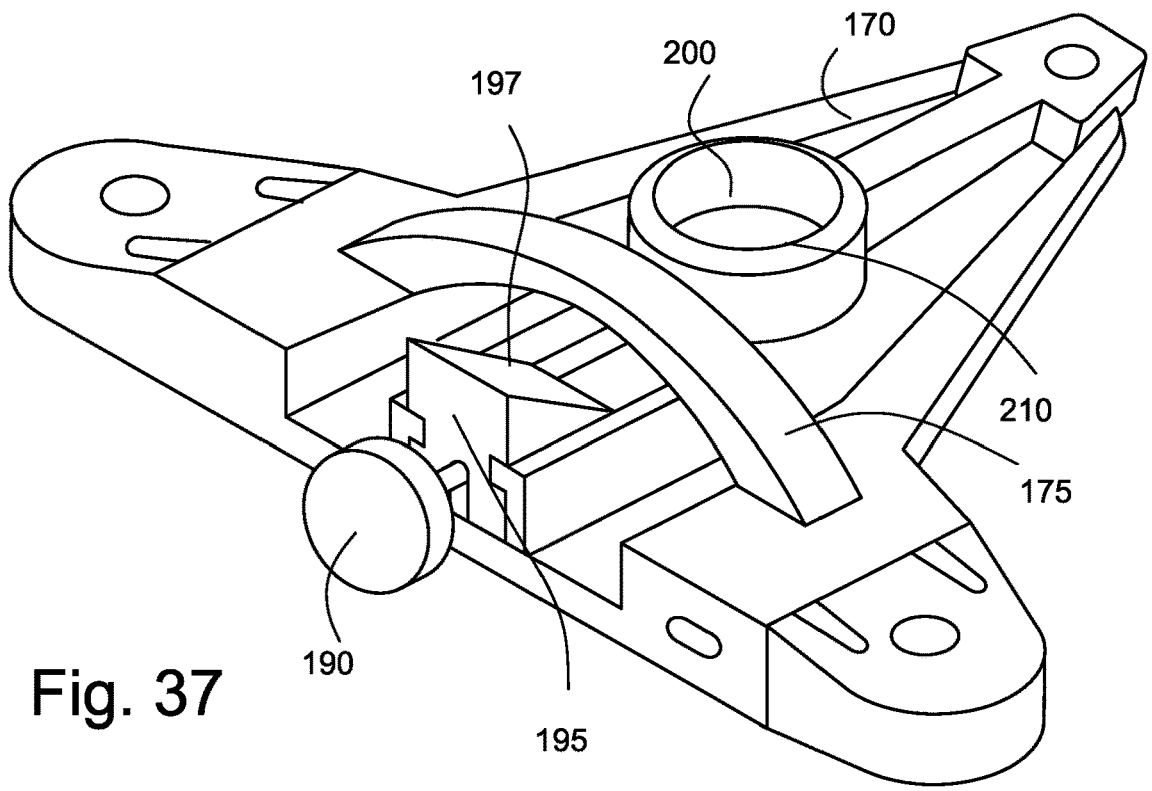
Figure 38:
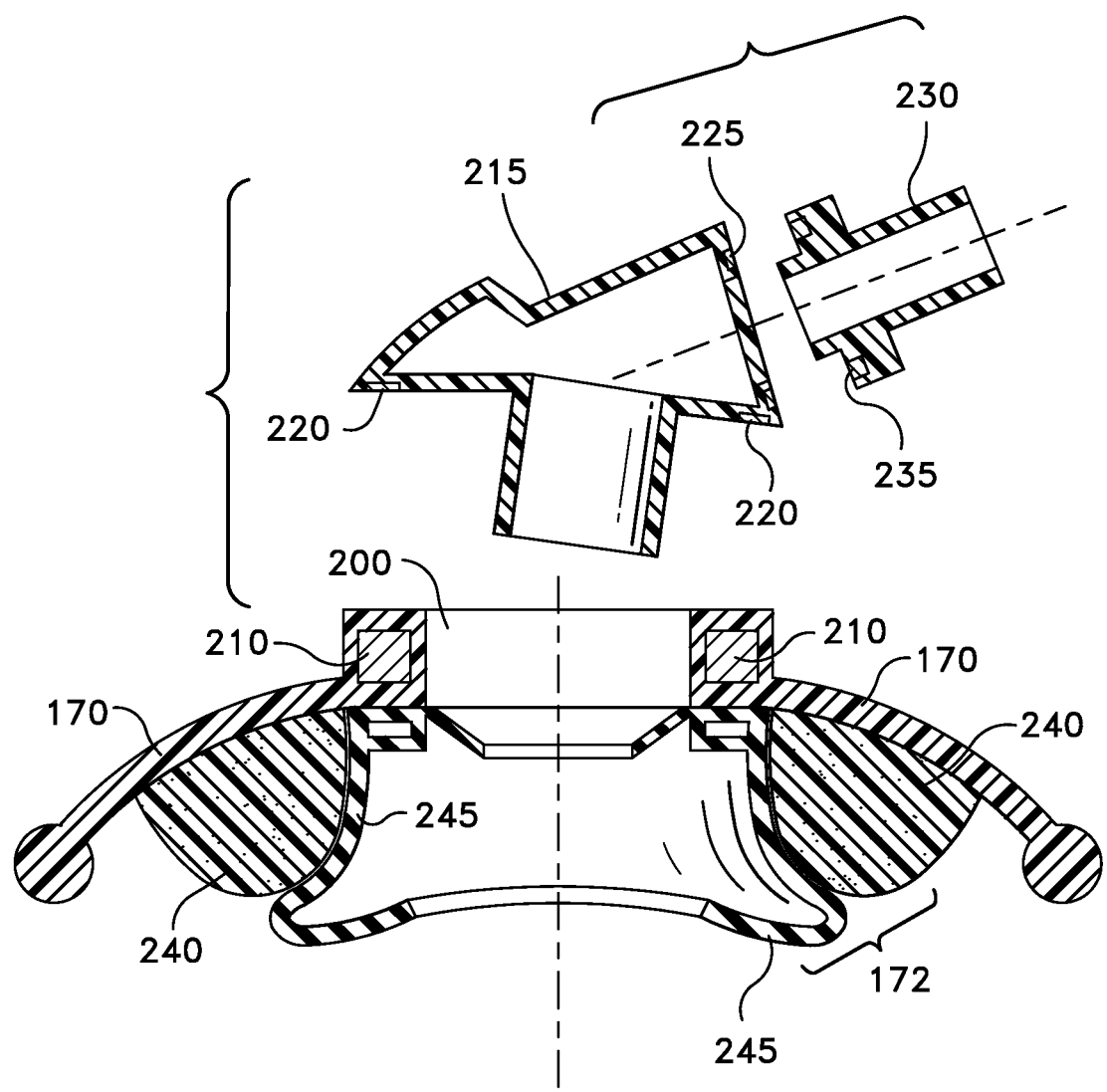

FIG. 37 illustrates an embodiment similar to the embodiment of FIG. 36, but includes additional features. For example, FIG. 37 discloses an aperture 200 which is surrounded by a ring shape member, e.g., a ferrous ring 210. As shown in FIG. 38, the aperture 200 is adapted to receive a connector 215 which is similar to an elbow. The connector 215 includes a first ferrous ring 220 which is adapted to magnetically couple with the ferrous ring 210 of the frame 170. The connector 215 includes a second ferrous ring 225 which is adapted to magnetically couple with a swivel member 230 via a magnetic ring 235 provided in the swivel 230.

FIG. 38 shows more details on the construction of the cushion. In particular, the cushion 172 includes a base member 240, e.g., foam, provided to the inside of the frame 170 and a membrane 245, e.g., silicone, that is supported by the base portion 240.

In FIG. 37, the distance between the top surface 197 of the wedge 195 and the inside surface of the warping strap 175 is exaggerated so as to more easily view the individual components.

Figure 39:
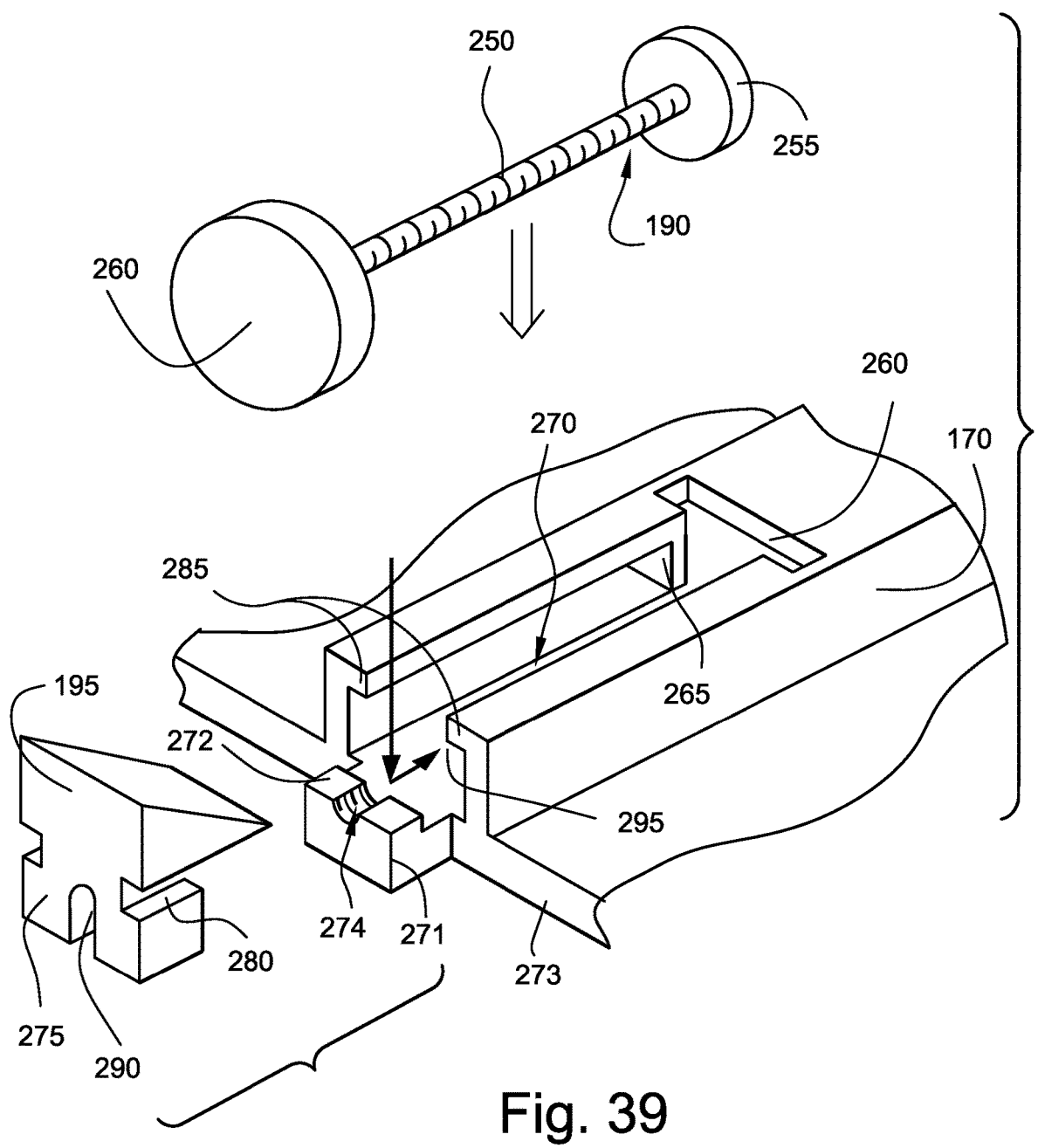

FIG. 39 shows a detailed view of the adjustment screw 190, the wedge 195 and the frame 170. In particular, the adjustment screw 190 includes a threaded portion 250 and a disc portion 255 provided at the opposite end of a knob 260 of the adjustment screw 190. The frame 170 includes a cross slot 260 adapted to receive the disc 255. The frame 170 has a longitudinal slot 265 adapted to receive the threaded portion 250 of the adjustment screw 190. The frame 170 includes an additional frontal slot 270 to receive a lower body portion 275 of the wedge 195. The frame 170 includes an extension 271 having an upright member 272 that is spaced away from the bottom edge 273 of the frame 170. The upright member 272 includes a bearing 274, which may be threaded. The wedge 195 includes a groove 280 which engages with inside wall members 285 which define the longitudinal slot 265. The wedge 195 includes a partially threaded portion 290. The partially threaded portion 290 is adapted to engage with the threaded portion 250.

Figure 40A:
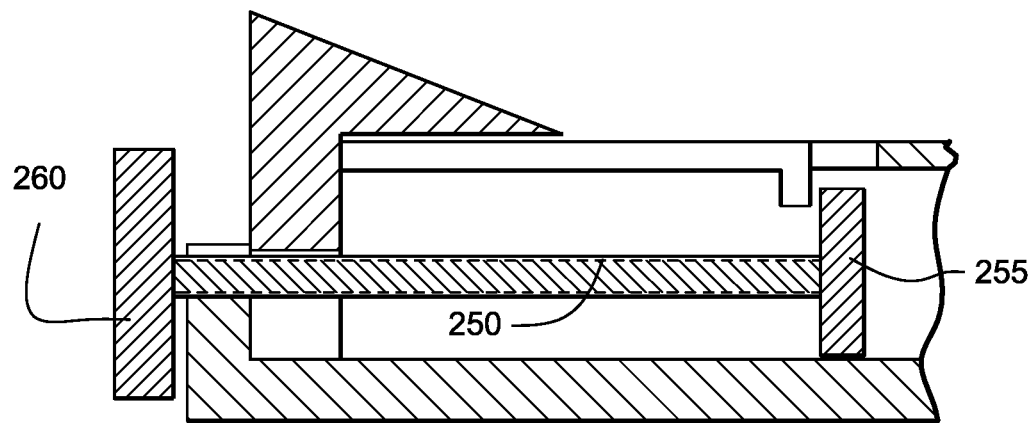
Figure 40B:
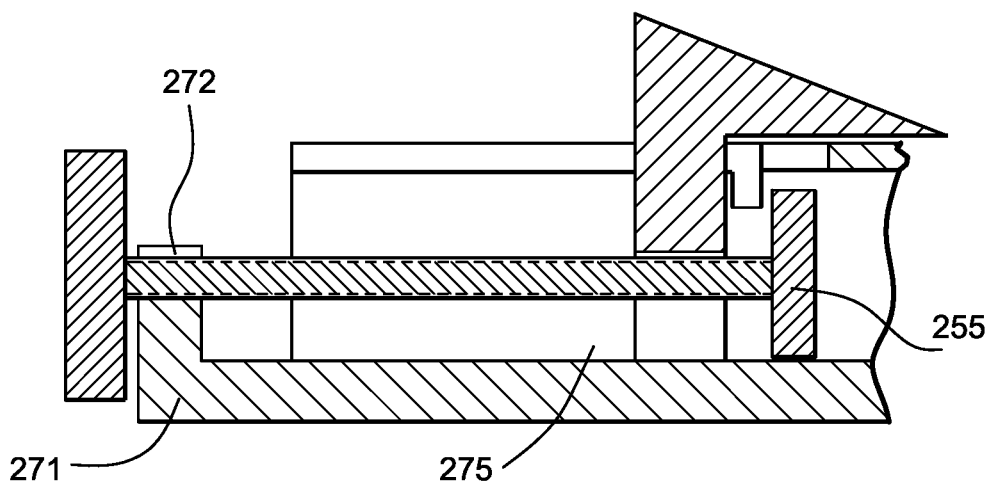

To assemble the adjustment mechanism, the threaded portion 250 and the disc 255 are inserted into the longitudinal slot 265 and the lateral slot 260, respectively. The partially threaded portion 290 of the wedge 195 is then dropped on top of the threaded portion 250, with the body portion 275 initially positioned between the upright member 272 and the end of the inside wall members 285 adjacent the bottom end 273 of the frame 170. The groove 280 is guided to slide along wall members 285. Accordingly, upon rotation of knob 260, the wedge 195 will move back and forth within the channel 295 of frame 170. The extreme positions of the wedge 195 are shown in FIGS. 40A and 40B, respectively.

FIGS. 41 through 53 illustrate additional embodiments which allow pinching along the lateral sides of the patient's face/nose. Similar parts have been designated with like reference numbers as compared to the embodiments of FIGS. 36 through 40B. Each of these embodiments allows for more control over adjustment and adapts more readily to variations in physiognomy between patient's with differently shaped noses.

3. Third Embodiment

Figure 41:
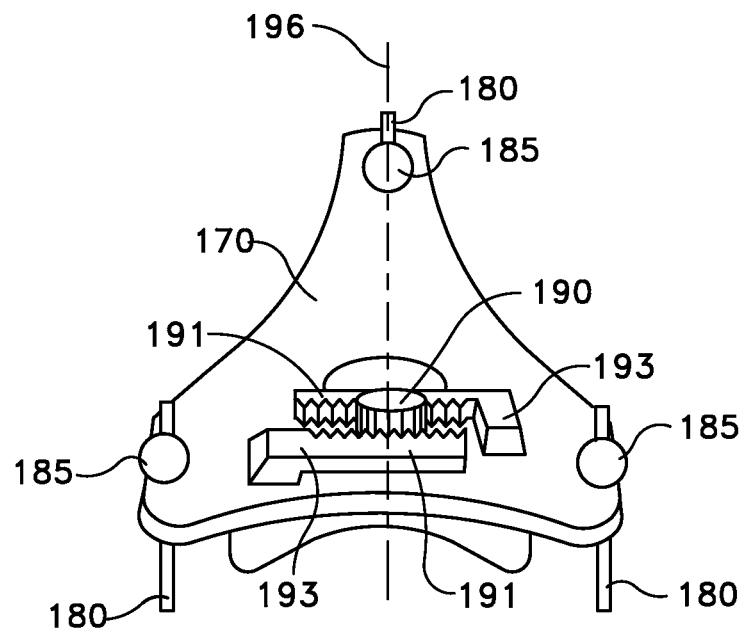

In the embodiment of FIG. 41, knob 190 is operatively coupled to one and preferably a pair of racks 191 which move in opposite directions upon rotation of knob 190. The distal ends 193 of the racks 191 engage with lateral portions of the frame, e.g., the frame includes cammed surface which progressively increase in thickness as the distal ends 193 are moved laterally outwards, to allow bending, flexing and/or pivoting of the frame about an imaginary vertical axis, to thereby enhance pinching against the sides of the patient's face/nose.

4. Fourth Embodiment

Figure 42A:
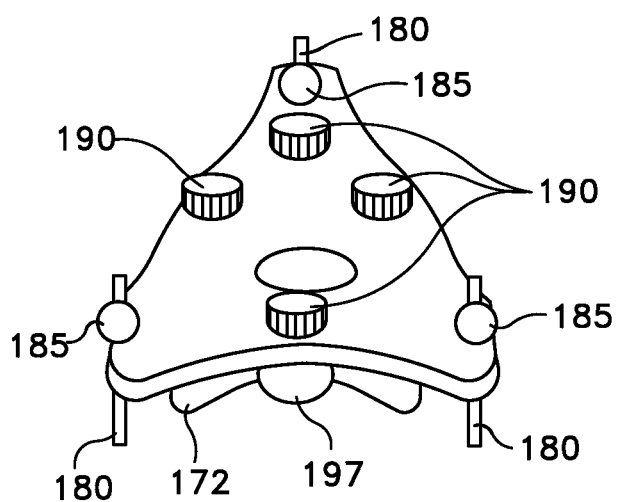

In the embodiment of FIGS. 42A and 42B, the membrane will assist in sealing small leaks, therefore accuracy of adjustment is not critical. In addition, the embodiment of FIGS. 42A and 42B substantially eliminates lift off from the chin. FIGS. 42A and 42B also include additional adjustment points, thereby enabling the fit of the mask to the patient to be even more finely tuned. For example, each knob 190 is operatively connected with a portion 197 which is provided to the cushion 172.

5. Fifth Embodiment

In FIGS. 43A and 43B, the frame 170 is semi-rigid while the cushion 172 is mounted to a flexible member 300. As the strap tension is increased, the spring action of member 300 on the cushion will help in the sealing against the sides of the patient's nose. For example, frame 170 may be a relatively stiff spring, compared to the stiffness of flexible member 300. Therefore, a patient with a crocodile type face may rely on stiffness of flexible member 300, and patients with a panda-like face may rely on the flexible member 300 lying flat against frame 170 which is flexible, but relatively stiffer than the flexible member 300. This embodiment is not shown to include an adjustment knob, but could be adapted as such.

6. Sixth Embodiment

Figure 44A:
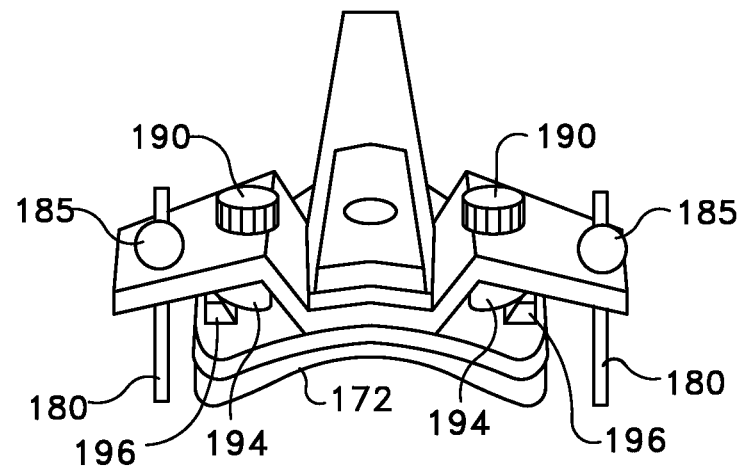
Figure 44B:
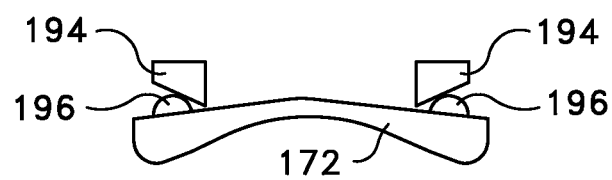
Figure 44C:
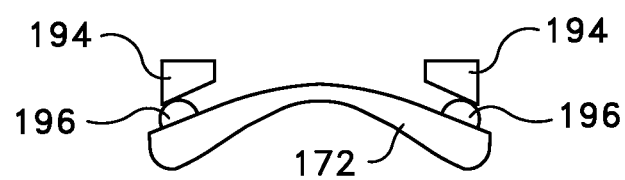

In the embodiment of FIGS. 44A-44C, rotation of adjustment screws 190 cause a cam shaped surface 194 of the screw to engage protrusions 196 on the cushion support, thereby pinching the cushion inwardly towards the patient's nose.

7. Seventh Embodiment

Figure 45:
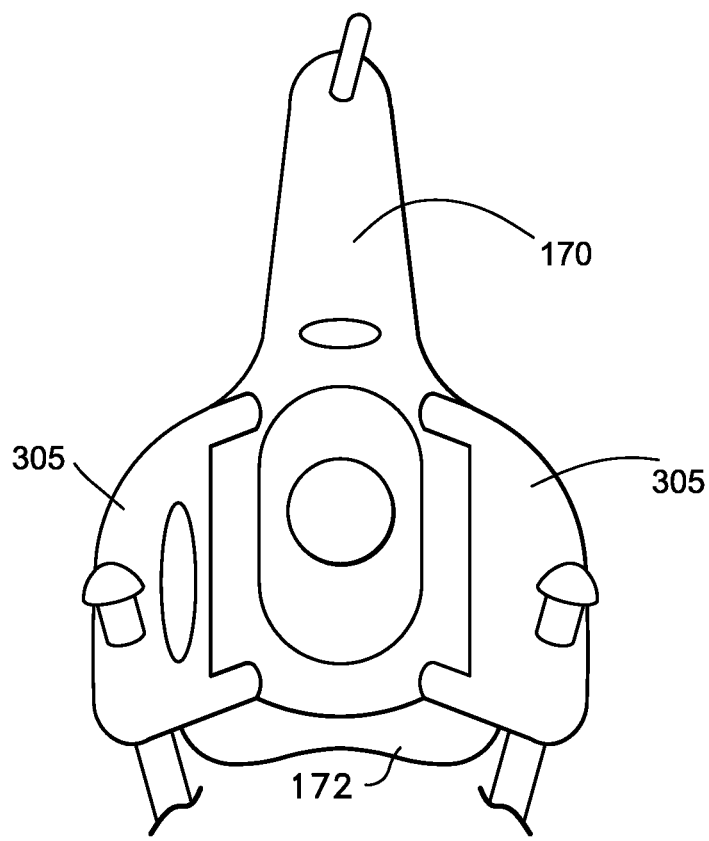
Figure 46A:
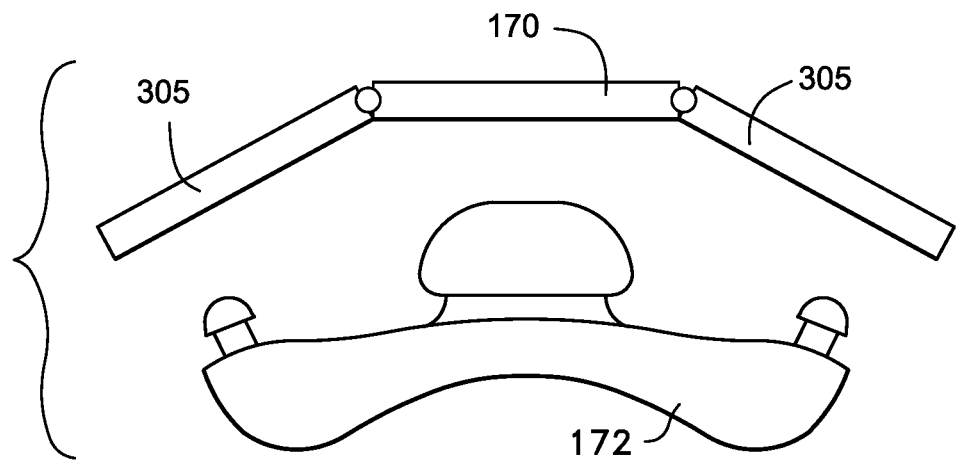
Figure 46B:
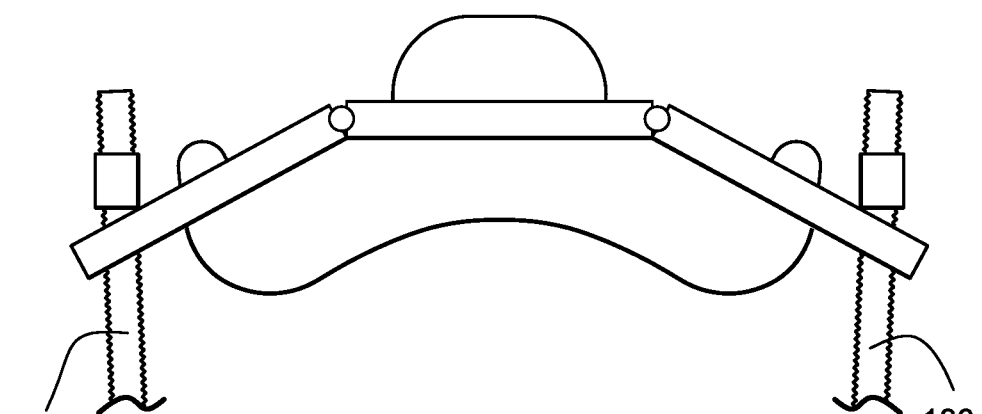

FIGS. 45, 46A and 46B illustrate yet another embodiment of the invention whereby the frame includes side wing portions 305 which can pivot with respect to the frame 170. In concept, this embodiment is similar to the embodiment shown in FIG. 1 in which the finger portions 115 are provided to pivot with respect to the chassis 95. FIG. 46A is an exploded view of the embodiment of FIG. 45, while FIG. 46B is an assembled view of the embodiment of FIG. 45. This embodiment, like other embodiments, allows the sides of the cushion to more readily conform to various patient's having differently shaped noses. This embodiment also automatically conforms to the face shape since the straps 180 are connected to each side wing portion 305 of the frame 170. Lift off of the mask/cushion from the cheeks is reduced, and a more even pressure of the cushion on the face can be achieved. This embodiment, like many of the other embodiments described above also allows for a replaceable or disposable cushion.

8. Eighth Embodiment

Figure 45B:
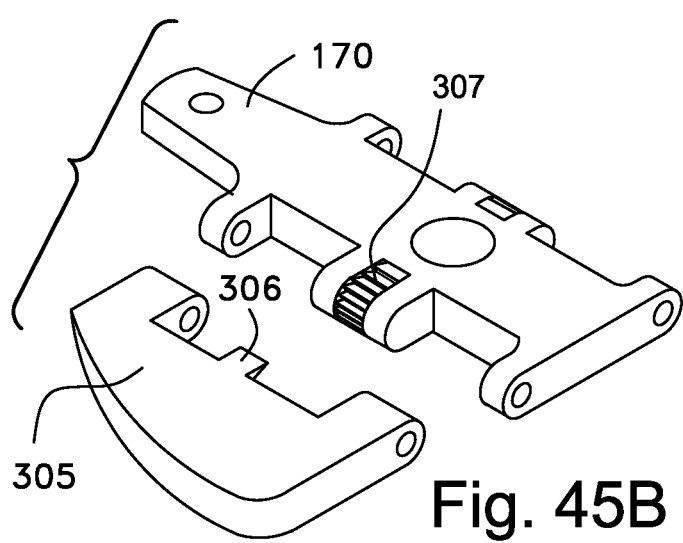
Figure 45A:
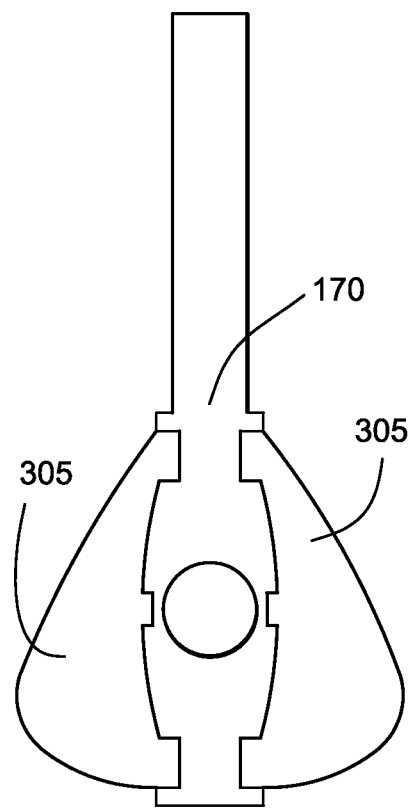

FIGS. 45A and 45B show yet another embodiment, similar to the embodiment of FIG. 45, in which the side wing positions 305 can be hingedly connected in a number of predetermined positions, by clicking or detenting action. FIG. 45B shows a partially exploded view including a tongue 306 provided between two hinge portions on the side wing portion 305. The frame 170 includes a plurality of grooves 307 adapted to receive the tongue 306, to thereby allow adjustability in a plurality of discrete positions.

Figure 47:
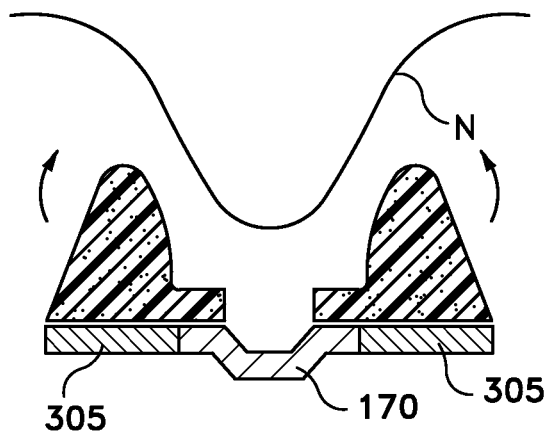
Figure 48:
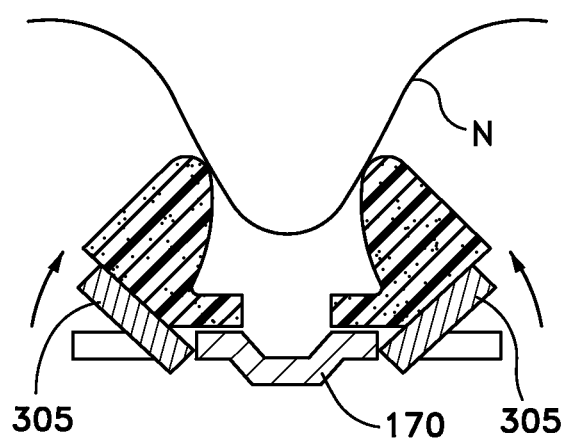

FIGS. 47 and 48 show the progressive sealing positioning of side wing portions 305 on the nose N of a patient, as the tension in the straps is increased.

9. Ninth Embodiment

Figure 49:
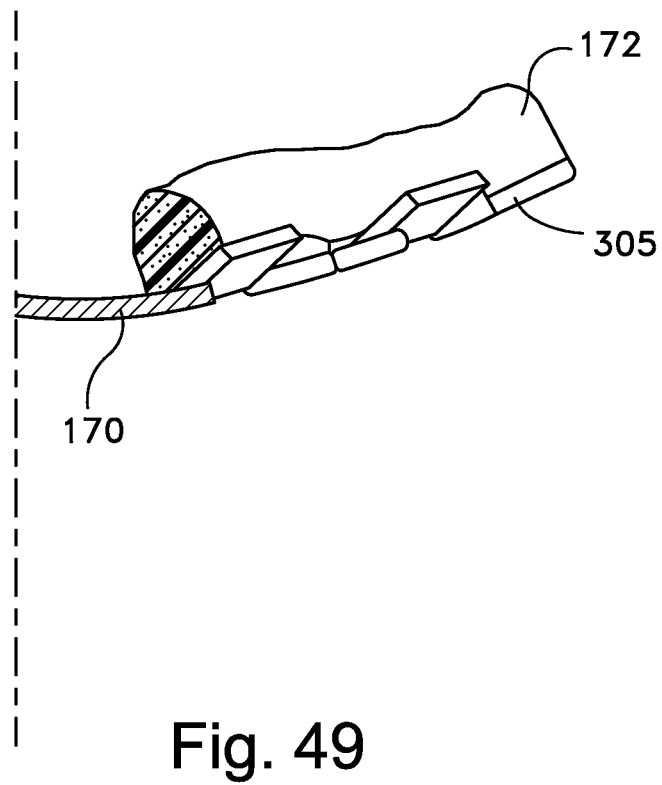
Figure 50:
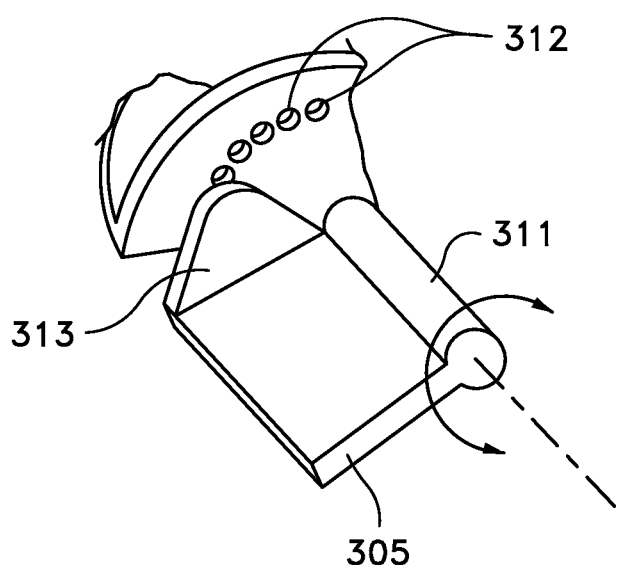

FIGS. 49 and 50 illustrate yet another embodiment of an adjustment mechanism which allows the side wing portions to move, e.g., pivot, with respect to the chassis or central frame of the mask assembly. The adjustment mechanism includes a plurality of holes 312 which can receive a pin provided on a flange 313 of the side wing portion 305. The hinge 311 could be a living hinge, a pin, an integral pin, etc.

10. Tenth Embodiment

Figure 51:
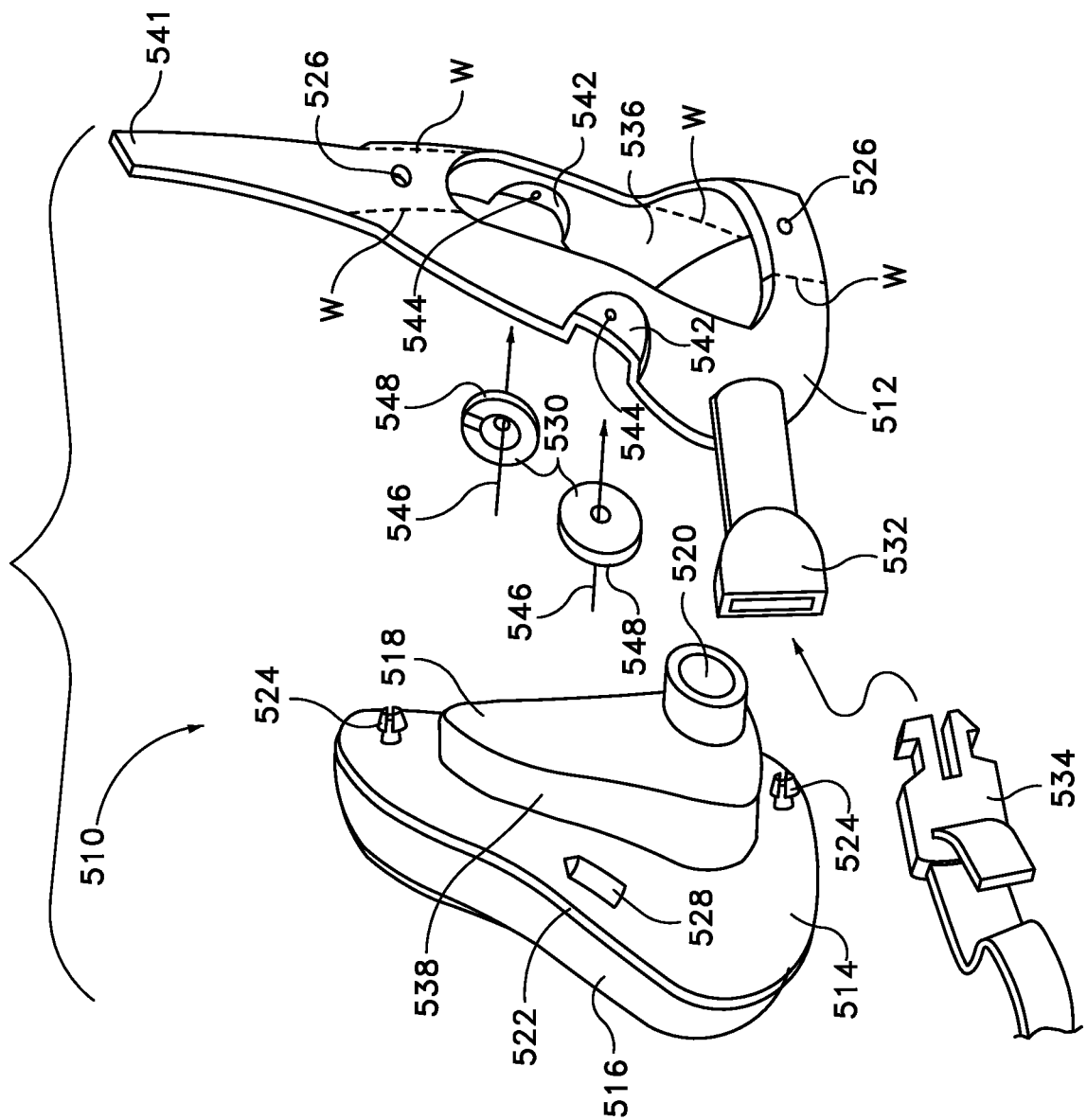

FIG. 51 is an exploded perspective view of a mask assembly 510 according to another embodiment of the invention. The mask assembly 510 has two major portions, a semi-rigid mask chassis 512 and a cushion/secondary frame 514. The two portions 512, 514 are separable, but may be releasably or fixedly connected, as described above. In general, the mask chassis 512 is constructed and arranged to connect to mask headgear (not shown in FIG. 51), and the cushion/secondary frame 514 is constructed and adapted to make a comfortable seal with a patient's face. The mask chassis 512 and the cushion/secondary frame 514 have structures that cooperate to cause the cushion/secondary frame 514 to move or deform relative to the mask chassis 512 so as to provide small adjustments in the fit of the mask assembly 510 to the user's face.

In the following description, certain directional terms, such as "top," "bottom," "left," and "right" will be used. Unless otherwise indicted, the directional terms are used with respect to the coordinate systems of the respective drawing figures.

The cushion/secondary frame 514 comprises a cushion portion 516 and a secondary frame portion 518. The two portions 516, 518 are fixedly connected. The cushion/secondary frame 514 may be sized to act as a mouth mask, nose mask, mouth-and-nose mask, or any other type of mask that is compatible with the user's treatment protocol.

The secondary frame portion 518 is triangularly or pyramidally shaped and provides sufficient interior volume to accommodate the facial features over which the cushion/secondary frame 514 is designed to make a seal (e.g., nose, nose and mouth, etc.). The secondary frame portion 518 is open on two sides. On the outward side of the secondary frame portion 518, a connector 520 is provided to connect to a gas supply conduit. On the inward side, the secondary frame portion 518 is open and flares into a flange 522, to which the cushion portion 516 is connected. The secondary frame portion 518 may be made of a flexible or semi-flexible material, e.g., polypropylene.

The cushion portion 516 is a generally soft and conforming structure that may be, for example, a silicone membrane, foamed material (such as polyurethane foam) encapsulated within a plastic membrane, or a sealed, deformable compartment filled with air or another gas. It may be molded to (i.e., fused to) the secondary frame portion 18, fixed using adhesives, or secured with appropriate connecting structures.

The secondary frame portion 518 also includes structures constructed and arranged to connect the cushion/secondary frame 514 to the mask chassis 512. At the top and bottom of the secondary frame portion on its patient-outward surface are connecting members 524 that are adapted to be inserted into corresponding receiving holes 526 in the mask chassis 512 to secure the cushion/secondary frame 514 to the mask chassis 512. Connecting members 524 are constructed and arranged to deflect inwardly on insertion into the receiving holes 526 to provide a snap fit between the cushion/secondary frame 514 and mask chassis 512. Although connecting members 524 are shown in FIG. 51, the connection between the cushion/secondary frame 514 and the mask chassis 512 may be any other type of suitable connector. The secondary frame portion 518 also includes projections 528 with surfaces that cooperate with adjustment wheels 530 in a manner that will be described below.

The mask chassis 512 is a generally triangular contoured plate of semi-rigid material, which may be co-molded with the cushion/secondary frame 514. The mask chassis 512 provides connecting receptacles 532 for corresponding ends of the mask headgear 534. In mask chassis 512, two connecting receptacles 532 are provided, one at each of the left and right edges of the mask chassis 512. However, any number of connecting receptacles 532 may be provided, disposed about the mask chassis 512 as required, depending on the number and position of the headgear straps or strap ends. In FIG. 51, the connecting receptacles 532 and mask headgear 534 are illustrated as having releasable snap-fit connections. However, the connecting receptacles 532 may be any type of conventional connecting structure. The top edge 541 of the mask chassis 512 generally includes connecting structure for connecting to a sagittal strap or strap portion of the mask headgear. Depending on the configuration of the sagittal strap or strap end, the connecting structure at the top edge 541 may be a connecting receptacle 532 or another connecting structure The mask chassis 512 includes a central aperture 536 that is constructed and sized to receive the raised, central portion 518 of the cushion/secondary frame 514, such that the connector 520 may be connected to an appropriate conduit for gas delivery through the central aperture 536 of the mask chassis 512. Adjacent to the central aperture 536 on the left and right sides of the mask chassis 512 are adjustment wheel retaining portions 542. The positions of the adjustment wheel retaining portions 542 generally correspond to those of the projections 528 on the cushion/secondary frame 514. Each adjustment wheel retaining portion 542 is raised relative to the surrounding surface of the mask chassis 512 and includes a hole, e.g., threaded hole 544.

Figure 52:
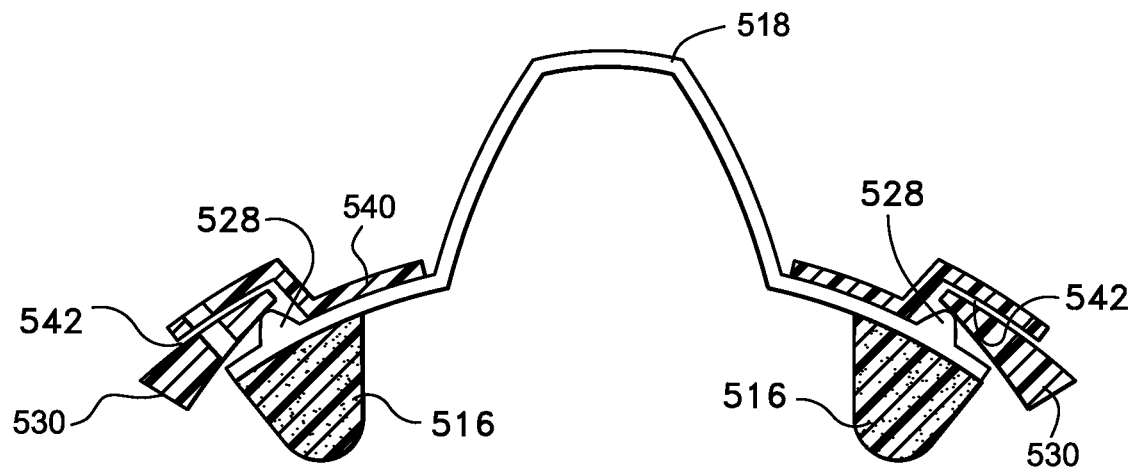
Figure 53:
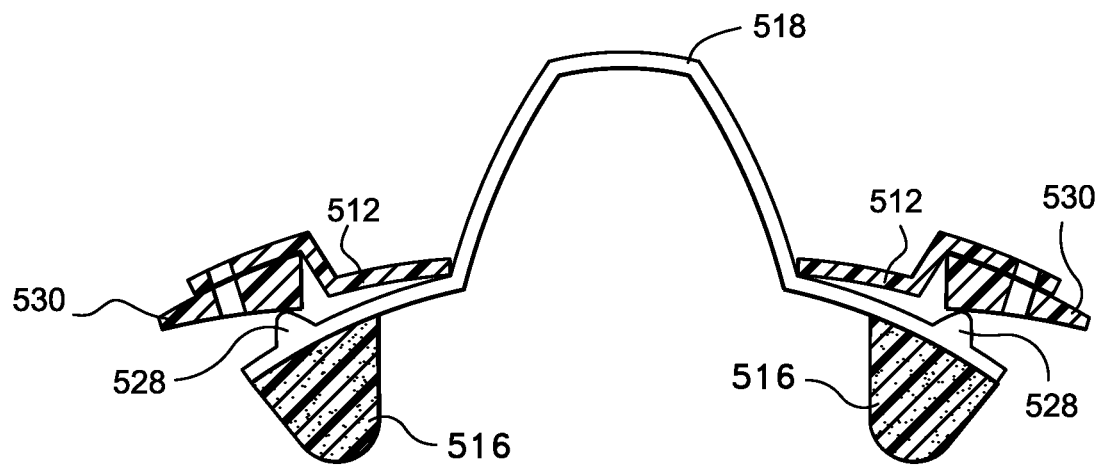

The operation and interrelation of the adjustment wheel 530, adjustment wheel retaining portion 542 and projection 528 are better illustrated in FIGS. 52 and 53, which are schematic cross-sectional views of a portion of the connected mask chassis 512 and cushion/secondary frame 514 in an engaged position, showing an adjustment wheel 530 installed in an adjustment wheel retaining portion 542 and engaging a projection 528 on the secondary frame 518. The adjustment wheel 530 comprises a threaded rod or rivet 546, one end of which is secured into a user-turnable head 548 to form a thumbscrew and the other end of which is coupled or provided to the bore 544. In FIG. 52, the more narrow or thinner portion of the wheel 530 is in contact with the protrusion 528. Consequently, the cushion/secondary frame 514 is in a substantially undeformed state that is not influenced by the mask chassis 512. The undeformed state of the cushion/secondary frame 514 may or may not make a good seal against a user's skin, because of the presence of gaps or simply insufficient sealing force.

To adjust the force of the cushion/secondary frame 514 against the skin 550, the user would turn the adjustment wheels 530, causing the thicker portion of the wheel 530 to move towards and contact the projection 528. Once the thicker portion has contacted the projection 528, the secondary frame portion 514 deflects to thereby cause the cushion 516 to move towards or more closely towards the patient's skin, thereby adjusting the sealing force and/or fit. FIG. 53 illustrates the wheel 530 in a position in which it causes the cushion/secondary frame 514 to deflect towards the skin, eliminating the gaps and/or improving the fit/seal between the skin 550 and cushion portion 516.

In addition to the adjustment mechanism described above, certain portions of the mask chassis 512 may be locally weakened in order to allow the mask chassis 512 to flex slightly to accommodate various facial shapes. For example, the portions of the mask chassis 512 along lines W may be locally weakened to allow the mask chassis 512 to flex. The mask chassis 512 could be made stiffer than the secondary frame, either through materials, e.g., polycarbonate, geometry, e.g., stiffening ribs, constraints, e.g., tension from headgear, or combinations thereof.

FIG. 51 illustrates an embodiment of the invention in which the mask chassis 512 and cushion/secondary frame 514 are separate pieces, and in which the movement of the cushion/secondary frame 514 relative to the mask chassis 512 is caused primarily by deflection. However, in other embodiments of the invention, positioning structures may be included in the mask chassis and/or cushion/secondary frame in order to move the cushion/secondary frame relative to the mask chassis. Additionally, the mask chassis and cushion/secondary frame may not be provided as separate or separable components, as described above in other embodiments.

B. Fins

1. First Embodiment

FIGS. 53A-53G illustrate two closely related embodiments of the present invention. Each embodiment is structured and arranged so as to help improve the lateral sealing force against the sides of the nose. These embodiments have particular use in the nasal bridge region, but could also be applied in other regions, such as the region adjacent the lower portion of the nose or the mouth.

FIGS. 53A-53C illustrate one embodiment in which a frame 600 has a generally triangular shape and in this example is structured to support a full face mask cushion, although it could be adapted for use as a frame for a nasal cushion. The frame 600 may include other shapes, such as generally round, trapezoidal, or any shape that accommodates the intended area of the patient which serves as the interface.

The frame 600 includes a pair of lateral members 605 each including a connector interface 610 with at least one and preferably a plurality of apertures 615. Each aperture 615 is structured to receive an end of a headgear strap, preferably of the substantially inextensible type described above. The headgear strap can be connected to any one of the apertures 615. Alternatively, the apertures can be provided to a side wall 617 of the connector interface 610.

As shown in FIGS. 53B and 53C, a surface 616 oriented towards the patient's face includes a pair of fins 620 that are positioned just laterally outwards of the sides of the patient's nose in use. As seen in FIG. 53b, the fins 620 are positioned in the nasal bridge region of the patient's nose, but the fins 620 could also extend along a greater or an entire extent of the sides of the patient's nose. The fins 620 are structured to be received in a corresponding slot or groove formed in the facial cushion (not shown) or on the outside of the cushion. Each fin 620 may include one or more holes 625 which can help create a lock between the fin and the cushion, and may also reduce weight.

In use, the fins 620 provide a degree of lateral support to help maintain a good seal against the sides of the patient's nose. For example, as tension in the straps is increased, a normal cushion will have a tendency to billow laterally outwards, thus increasing the chance of compromising the seal or comfort of the cushion. The provision of the fins 620 helps prevent the cushion from billowing outwardly, to thereby help maintain the seal against the sides of the patient's nose.

The frame 600 may be structured to be flexible to as to be able to pivot, bend or flex generally about an axis A. As such, when the headgear straps are tightened, the frame 600 may move about the axis A, thereby causing the fins 620 to move inwardly to pinch the sides of the patient's nose. In addition or in the alternative, as the mask sides are bent, pivoted or flexed as shown by the arrows in FIG. 53C, a top portion 601 of the frame 600 bends, pivots or flexes towards the patient's nasal bridge region, as indicated by the arrow in FIG. 53B. In the initial position, the top portion 601 is bent away from the face of the patient. Accordingly, adjustment of the side straps may cause enhanced sealing in the nasal bridge region, thereby avoiding the need for a top strap.

When the mask is flexed around the primary, vertical, axis A, the frame 600 tends to straighten about the secondary, horizontal axis B. This results in the top 601 of the frame 600 moving closer to the face, and the cushion being pressed into the nasal bridge.

This works on the principal that when the frame is bent around one axis, the section of the frame that is already bent around another axis will undergo a much larger strain. Hence to minimize the strain energy in the material, it will straighten out the inbuilt bend, to move to a lower strain energy position. As the inbuilt bend is away from the face, straightening this will move that part of the mask closer to the face.

It can be seen that by varying the position and direction of the out of plane bending, any desired part of the frame can be made to move in and out as desired as the frame is bent in one known plane.

Alternatively or in addition, the frame 600 may include one or more lines of weakness 630, e.g., a hinge such as a living hinge, built in to top and/or bottom portions of the frame 600. The lines of weakness 600 will allow the frame 600 to more easily move about the axis A.

2. Second Embodiment

Figure 53D:
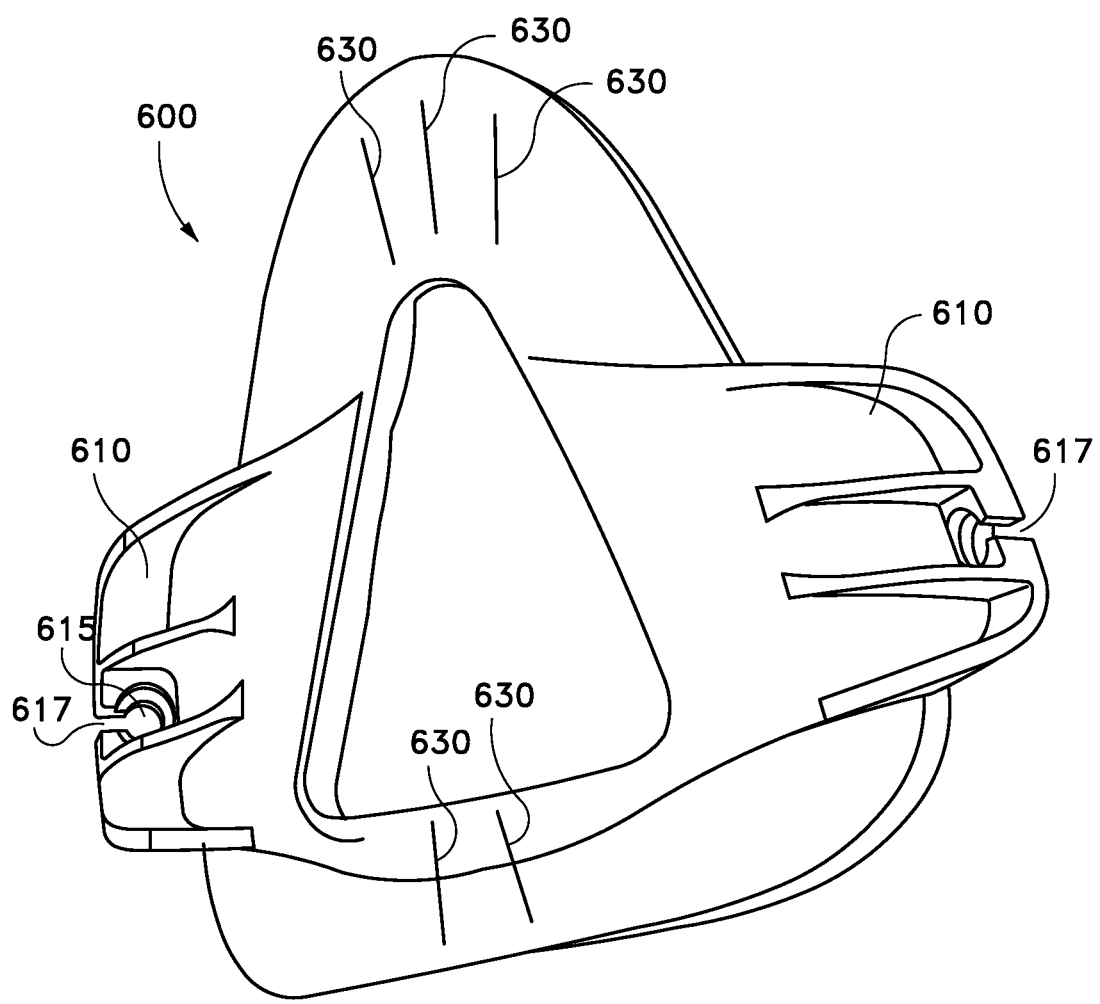
Figure 53E:
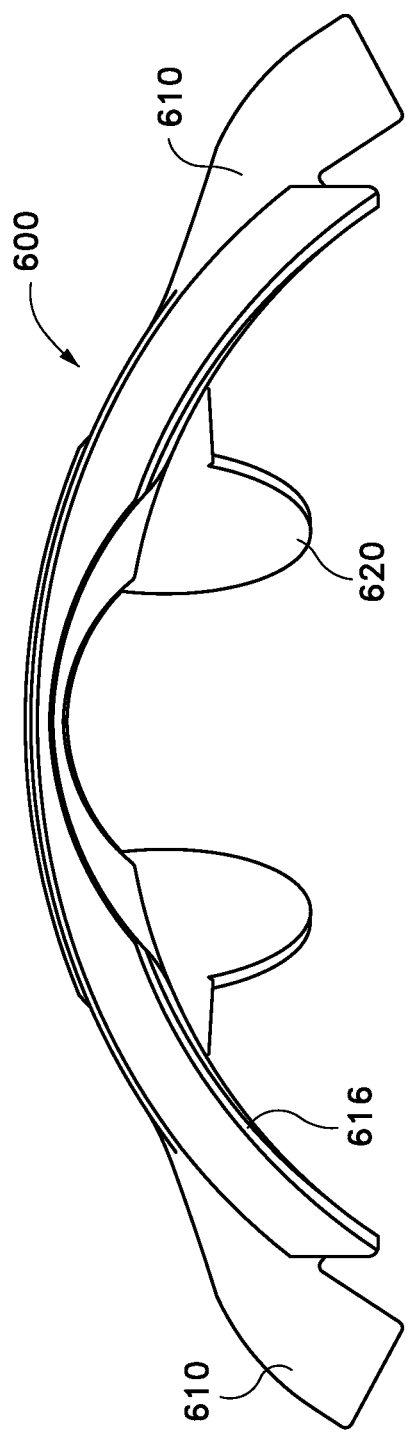

The embodiment of FIGS. 53D and 53E is very similar to the embodiment of FIGS. 53A-C. The main difference is that the connector interface 610 in FIGS. 53D and 53D includes only one aperture 615 for receiving an end of a headgear strap. The aperture 615 includes a slot 617 which is sized to allow the relatively thinner portion of the strap to slide therein, but will not allow the adjustable nut provided to the strap to pass. Further, as seen in FIG. 53E, the fin 620 does not include an aperture as in the embodiment of FIGS. 53A-C.

Figure 53F:
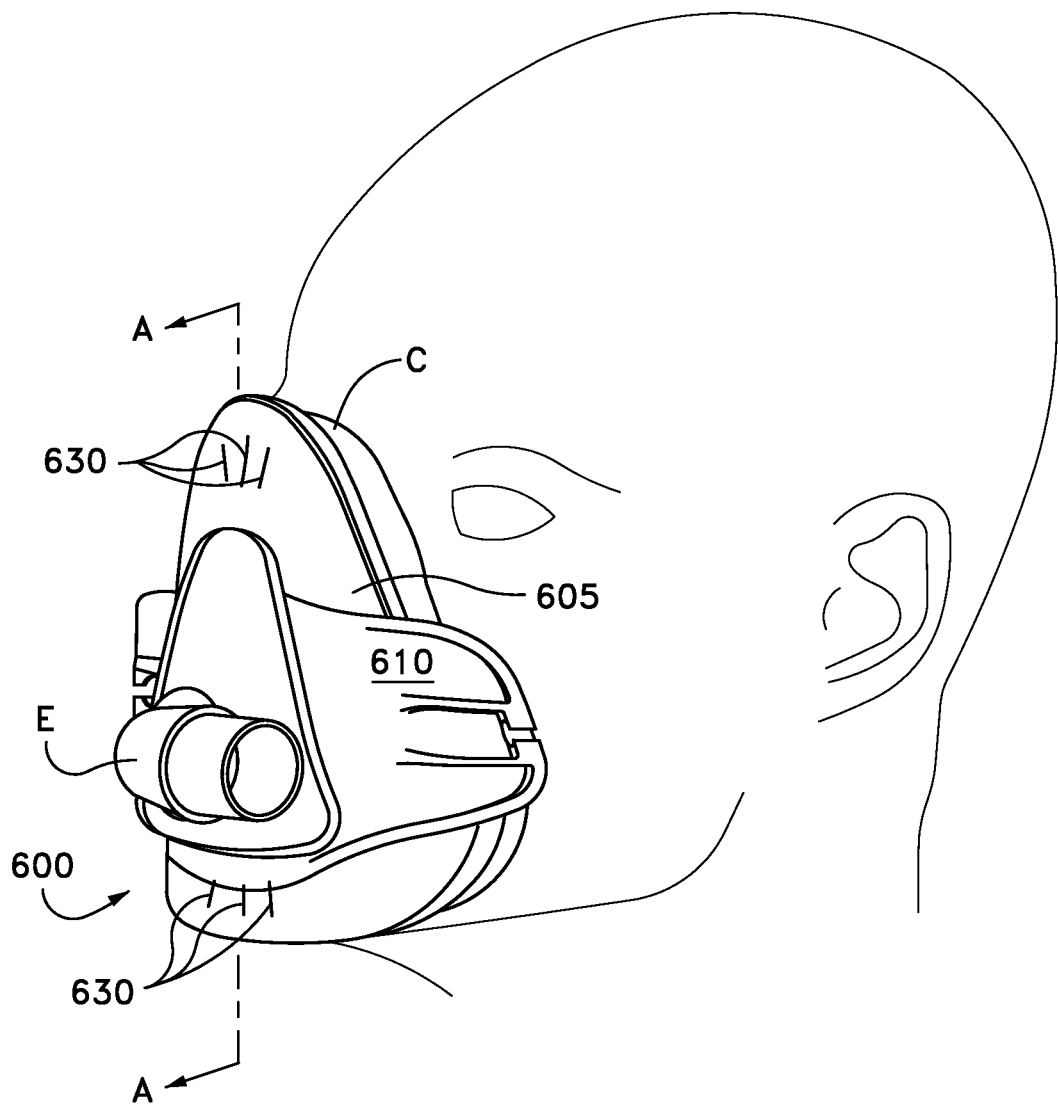

FIG. 53F shows the frame 600 of FIGS. 53D-E in an operative position on a model of a patient's head. The cushion C and elbow E have been attached to the frame 600. FIG. 53G is a cross-sectional view of the frame.

C. Frame with Pad

Figure 53H:
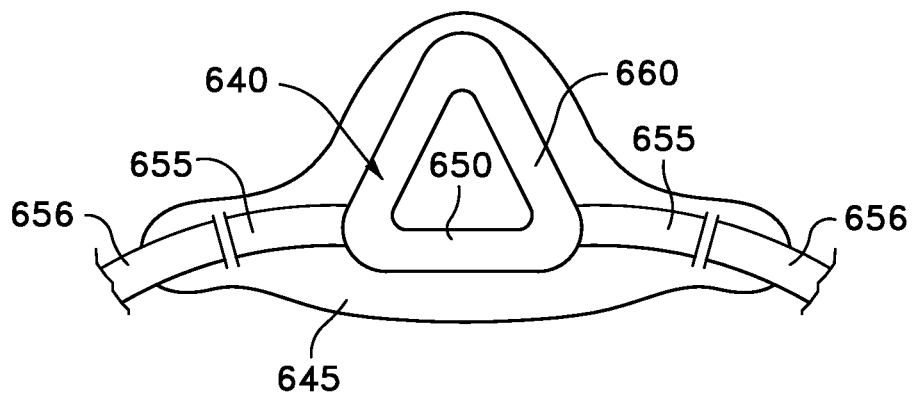
FIG. 53H illustrates an additional embodiments of the present invention in which the frame includes a pad.

FIG. 53H shows a further embodiment of the invention in which a frame 640 is provided with a pad 645. The pad 645 extends along a bottom portion 650 of the frame 640 and may be provided below clip 655 and at least a portion of headgear straps 656 that are provided to each lateral side 660 of the frame 640. The pad 645 may therefore provide additional comfort against possible abrasion of the clip 655 and/or strap 656 against the patient's cheeks. The pad 645 may be made of a gel and/or foam material.

D. Frame with Pegs

Figure 53I:
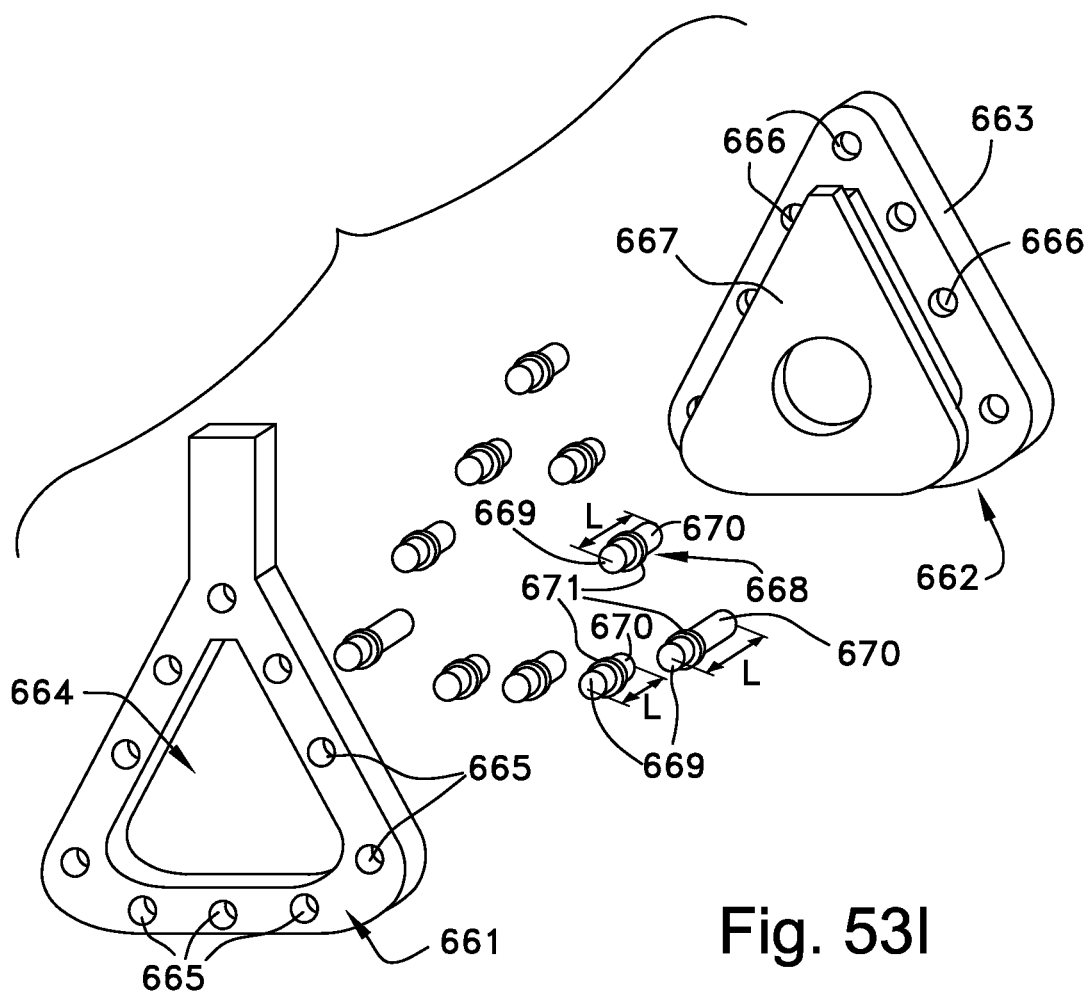
FIG. 53I illustrates an exploded perspective view of yet another embodiment of the present invention.
Figure 53J:
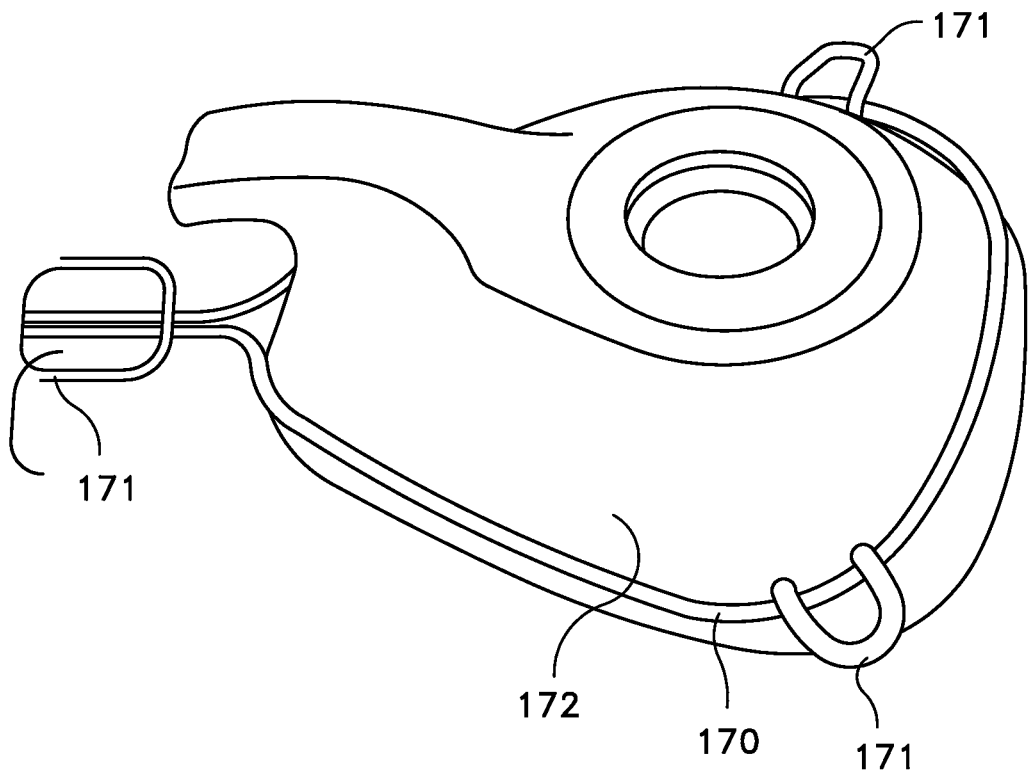
FIGS. 53J-53P illustrate yet another embodiment of the present invention in which the frame supports an inflatable cushion.
Figure 53K:
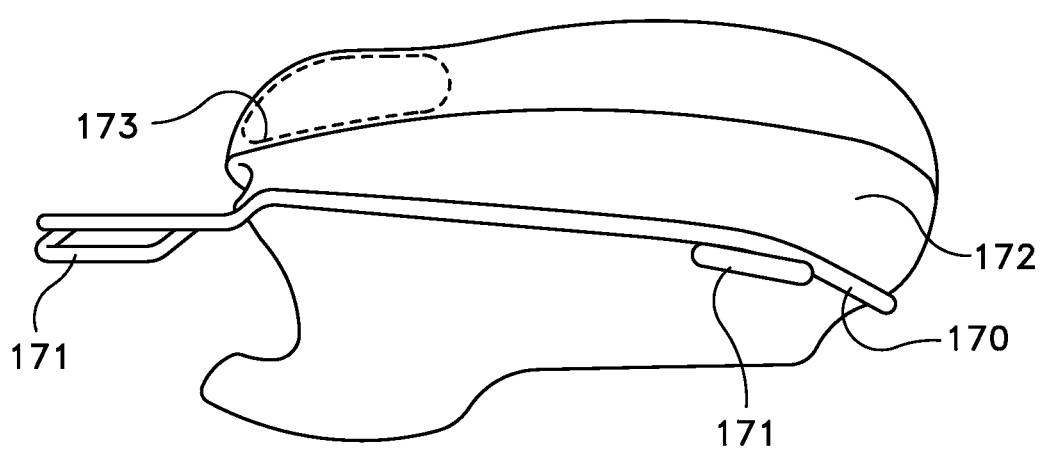
Figure 53L:
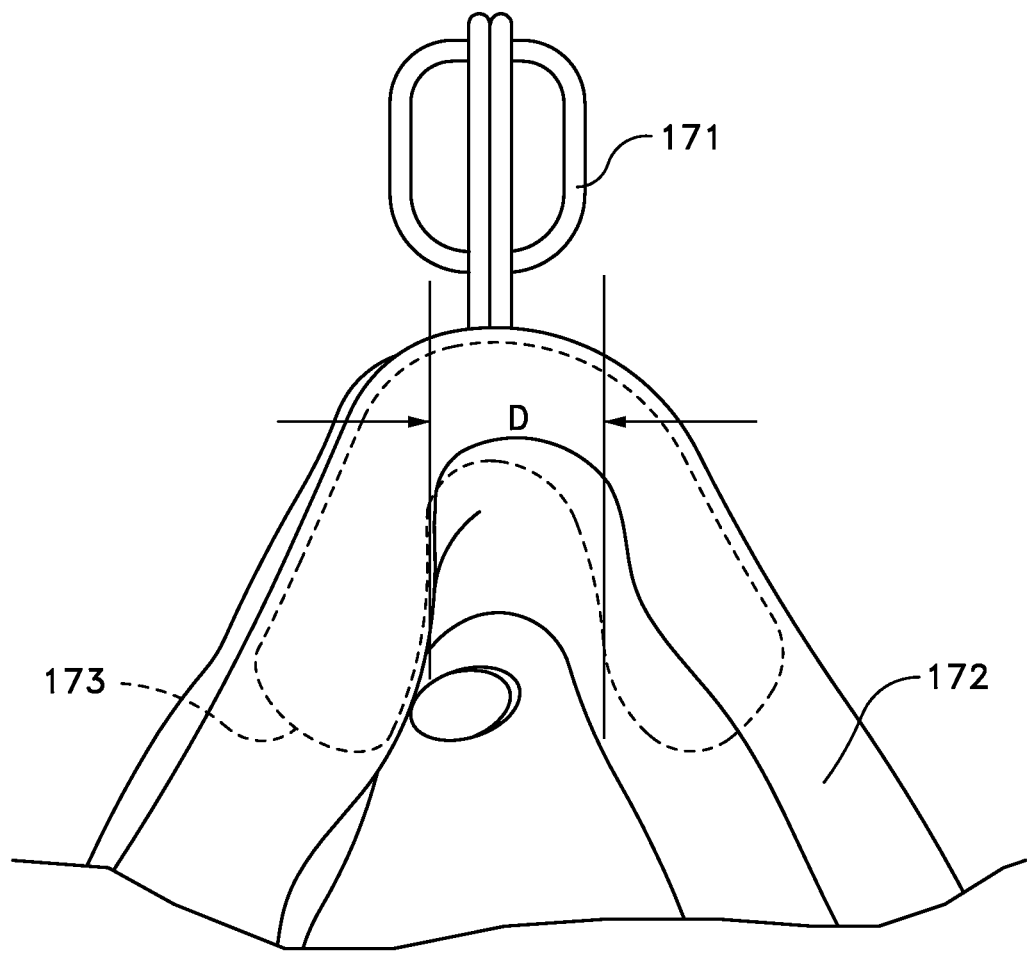
Figure 53M:
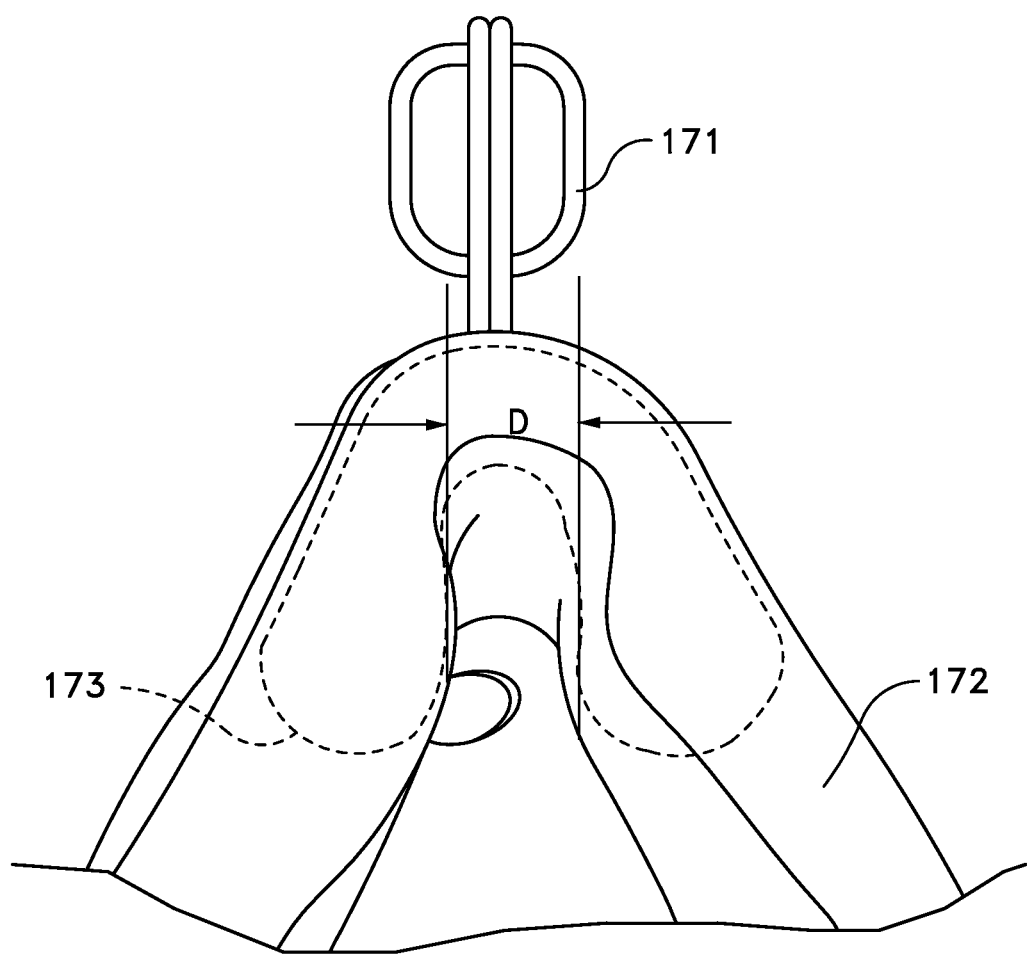
Figure 53N:
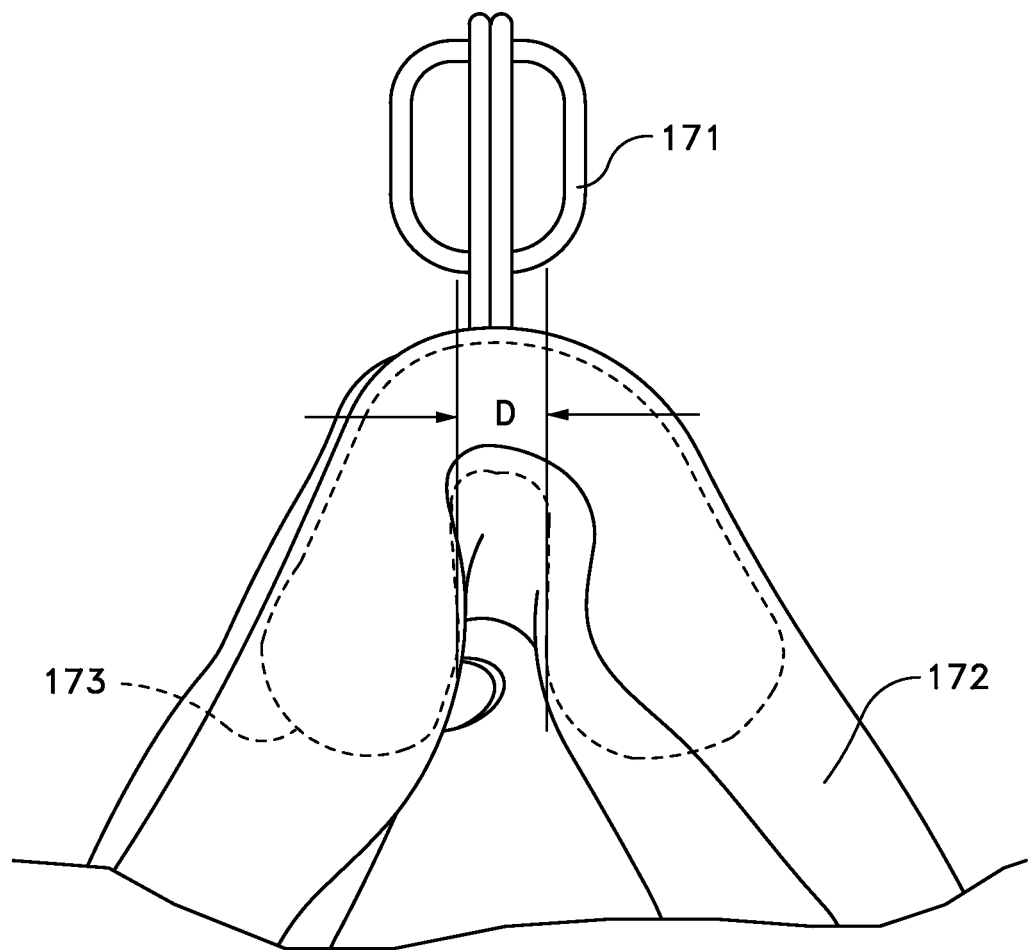
Figure 53O:
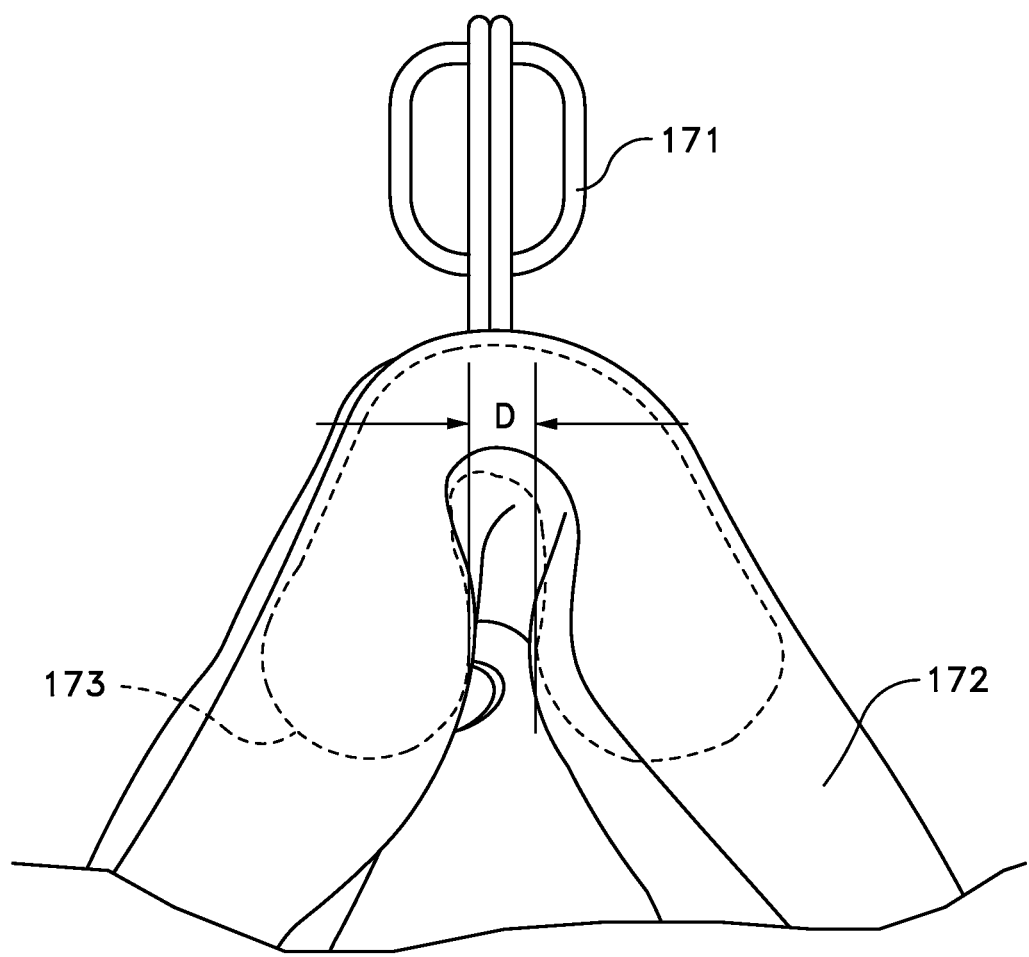
Figure 53P:
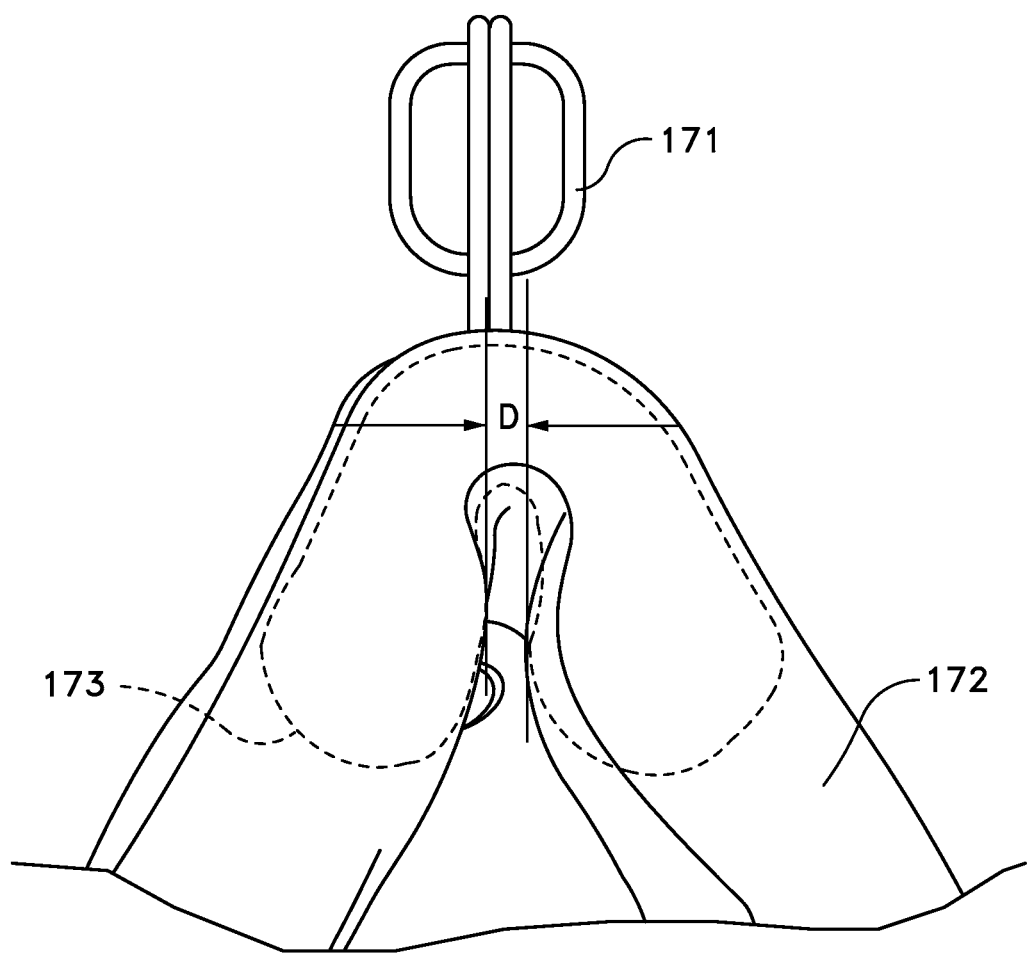

FIG. 53I illustrates a first frame member 661 and a second frame member 662 carrying a facial interface, e.g., a cushion 663. The first frame member 661 includes a main opening 664 and a plurality of first holes 665. The second frame member 662 includes a plurality of second holes 666 that align with the holes 665 of the first frame member 662. The second frame member 662 includes a protrusion 667 structured to be inserted through the main opening 665 of the first frame member 661.

A plurality of pegs 668 are provided between the first and second frame members 661, 662. Each peg 668 includes a first end 669 and a second end 670. The first end 669 is inserted into the first holes 665 while the second end 670 is provided to the second holes 666. Each peg 668 may be provided with a spacer or stopper 671. Each peg 668 has a length "L" that is selected to adjust its depth in relation to the interior of the cushion 663. For example, the pegs 668 are shown to have various lengths such that the second end 670 penetrates the second hole 666 to a depth within the cushion 663 that is tailored to the patient's facial physiognomy. As illustrated, the pegs 668 may hold the frames 661, 662 and/or the cushion 663 in place via press fit retention or the pegs 668 may include other structure to retain the cushion or frame members, e.g., barbs or undercuts.

E. Inflatable Cushion

FIGS. 53J-53P illustrate an embodiment of the invention where a frame 170 supports a cushion 172 made, for example of silicone and/or foam. The frame 170 may include one or more headgear connection points 171 provided about the perimeter of the frame 170. The cushion 172 may include an inflatable bladder 173 provided in the nasal bridge region of the patient's nose. The bladder 173 is shown to be a single piece which is embedded within the cushion 172, but it could include separate pieces which are provided to discrete portions of the cushion 172, in the desired positions. For example, the bladder may include two bladders which are provided to each side of the cushion, not including the apex of the cushion. The or each bladder 173 may be in communication with a source of material, e.g., air or gel, etc., to adjust the volume of the bladder 173. The or each bladder is provided to reduce or increase the distance between the associated cushion/frame section and the patient's face. For example, FIGS. 53L-53P show the distance D in the nasal bridge region being progressively decreased as the frame 170 is pinched in at the sides. FIGS. 53L-53P show that the change in the shape of the sides of the cushion 172 is asymmetrical, although it may be preferable to change the shape of the cushion and/or bladder 173 in a symmetrical manner, depending on whether the patient's nasal physiognomy is symmetrical or asymmetrical.

The cushion 172 can also be structured so as to minimize billowing of the sides of the cushion upon application of increased pressure. For example, the outer side walls of the cushion (remote from the patient's nose) can be made of a relatively thick gauge, so as to be relatively impervious to increased pressure, thereby reducing the chance that the outer wall will billow with increased pressure. Conversely, the inner walls of the cushion (adjacent the patient's nose) can be made of a relatively thin gauge wall member, which will allow them to easily deflect towards the patient's nose, thereby enhancing the seal.

Cushion

As used in this specification, the terms "rear" and "rearward" refer to the side of the cushion assembly adapted to contact the wearer's face and the terms "front" and "forward" refer to the side of the cushion assembly adapted to contact the mask shell or body. As also used in this specification, the term "mask" refers to nasal masks and full face masks.

Figure 54A:
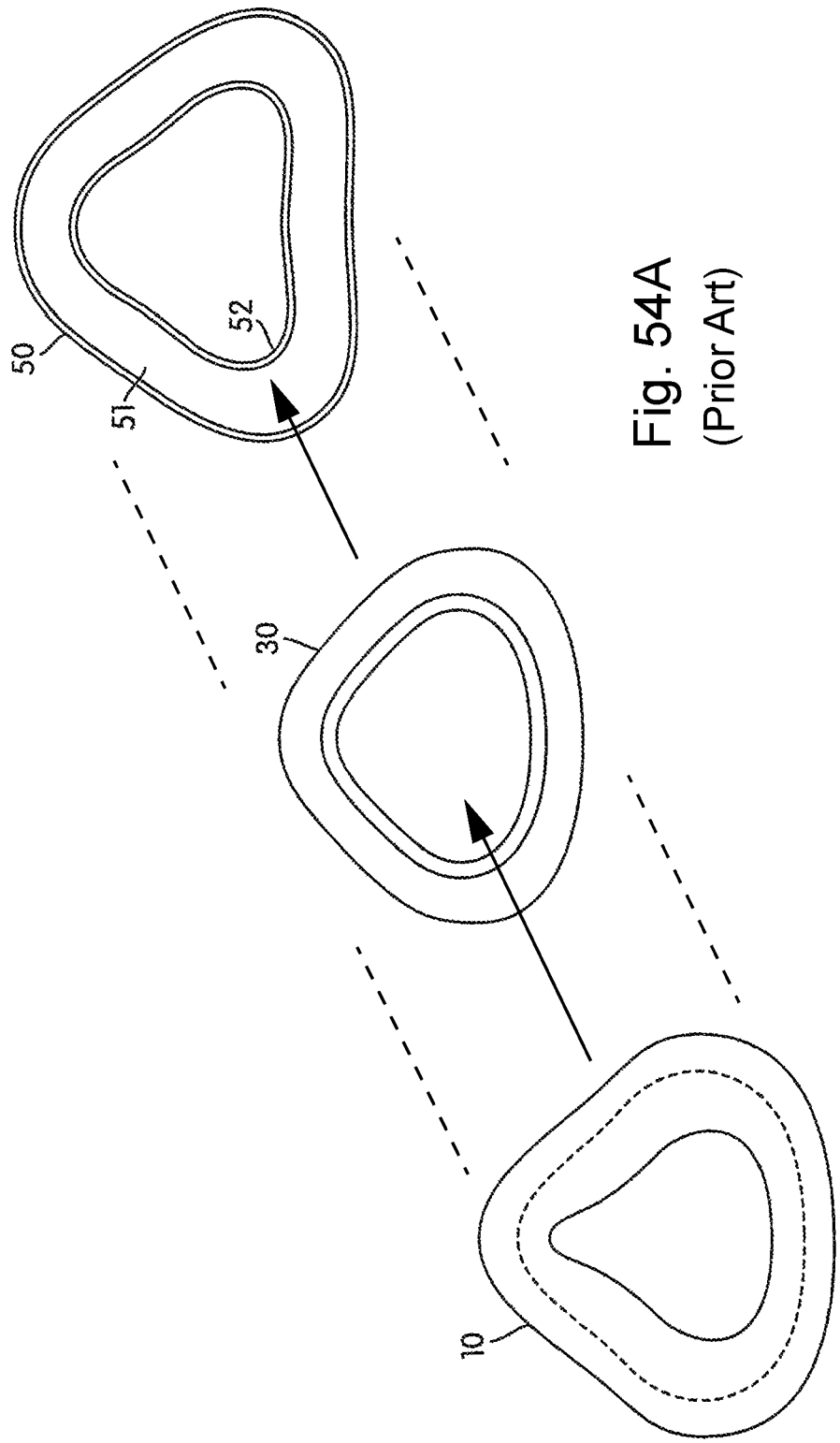
FIGS. 54A-54C are rear elevation, side elevation and bottom plan views, respectively, of a prior art ACLAIM cushion in exploded view.
Figure 54B:
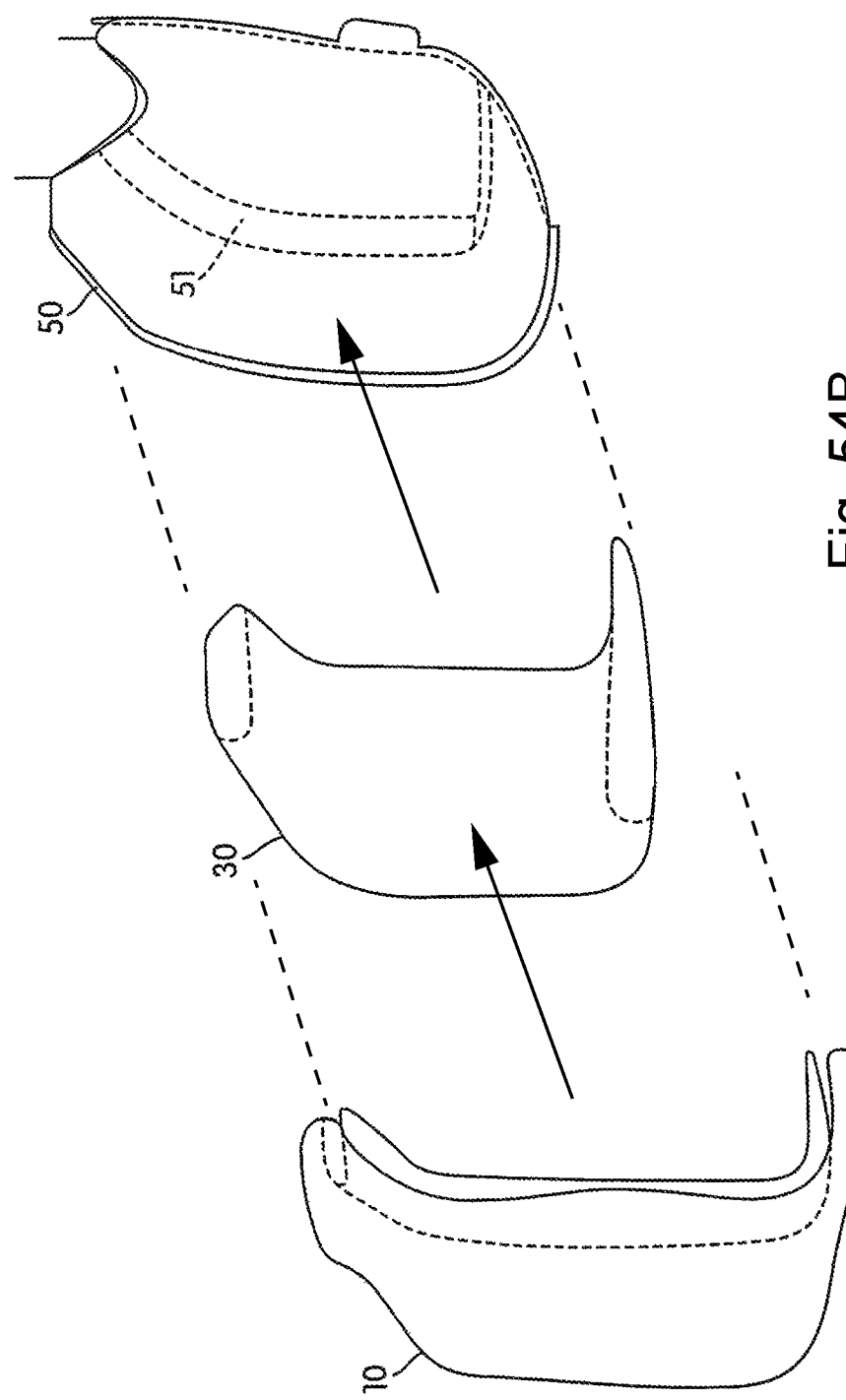
Figure 54C:
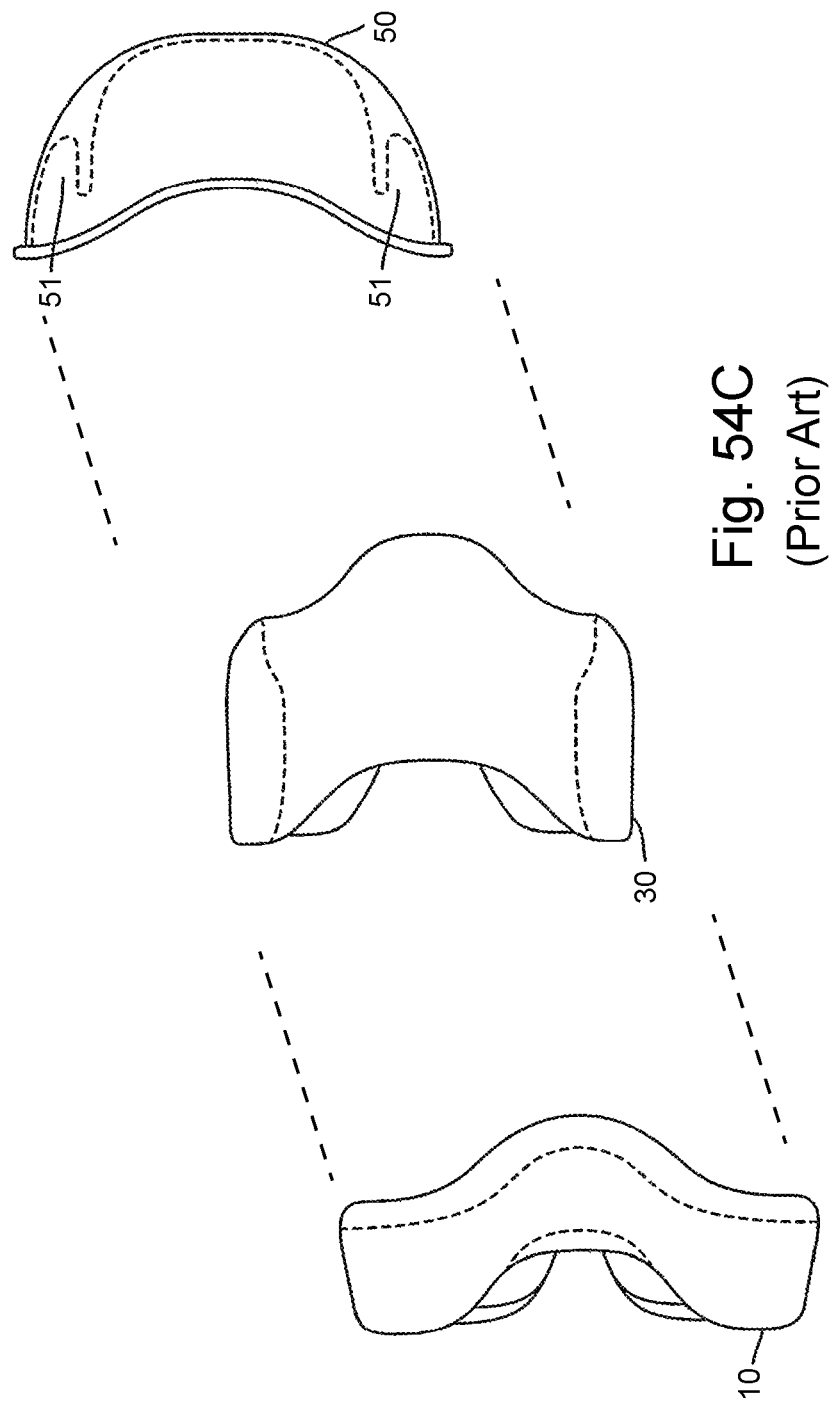
Figure 54D:
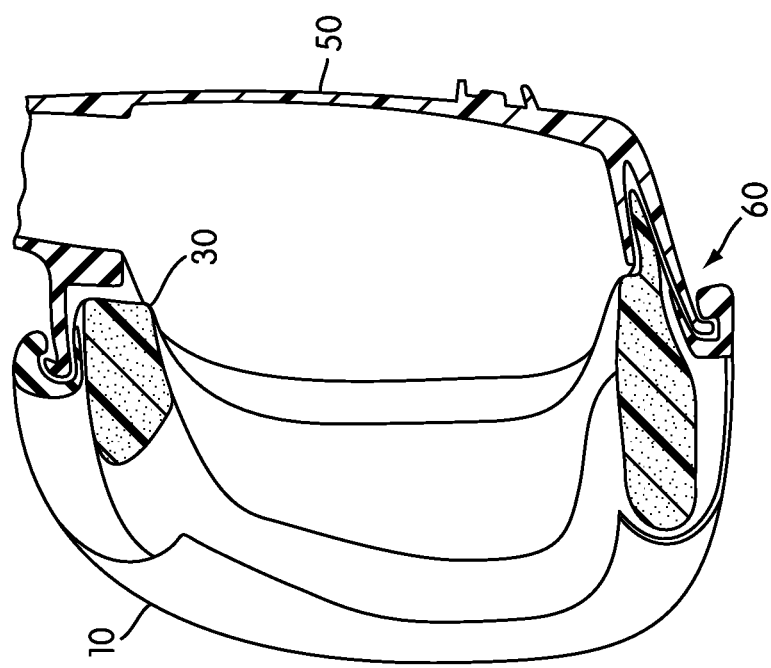
FIG. 54D is a cross section of the prior art ACLAIM cushion of FIGS. 54A-54C.

FIGS. 54A-54C are exploded rear elevation, side elevation and bottom plan views, respectively, of another known mask, the ACLAIM nasal mask, manufactured by Fisher & Paykel (F&P). The ACLAIM nasal mask includes a rigid frame or shell 50 and a cushion assembly including a thin silicone seal-forming membrane 10 and a foam rim 30. The shell 50 includes a channel 51 defined by an inner wall 52. In use the foam rim 30 is partially positioned in the channel 51 and extends rearwardly (i.e. toward the wearer's face). The membrane 10 is secured to the edge of the shell 50 via a tongue and groove mechanism 60 (FIG. 54D). The foam rim 30 serves as a supporting structure.

As used throughout this specification, the term "ACLAIM cushion" refers to the cushion assembly illustrated in FIGS. 54A-54D.

A problem with some prior art cushions such as the ACLAIM cushion is that they can collapse under high pressures leading to the face being subject to the edge of the frame. This is uncomfortable for the patient and may result in marks or sores on their face.

Figure 55A:
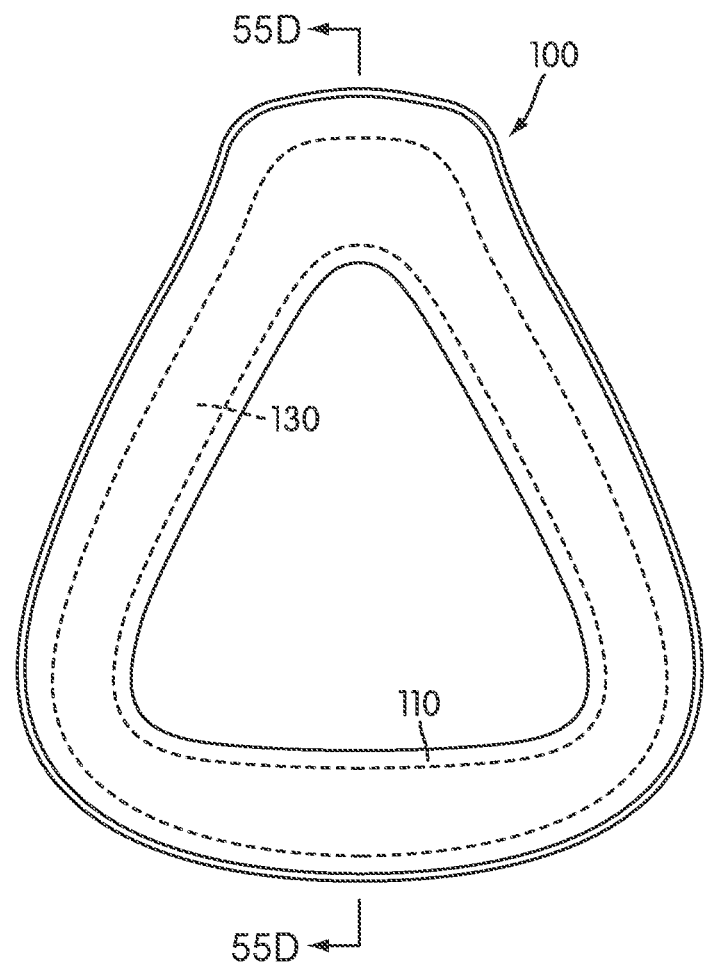
FIGS. 55A-55C are rear elevation, bottom plan, and side elevation views, respectively, of a cushion assembly according to a first embodiment of the present invention.
Figure 55B:
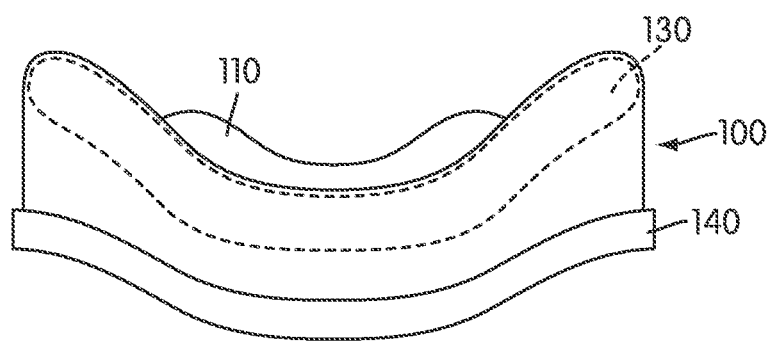
Figure 55D:
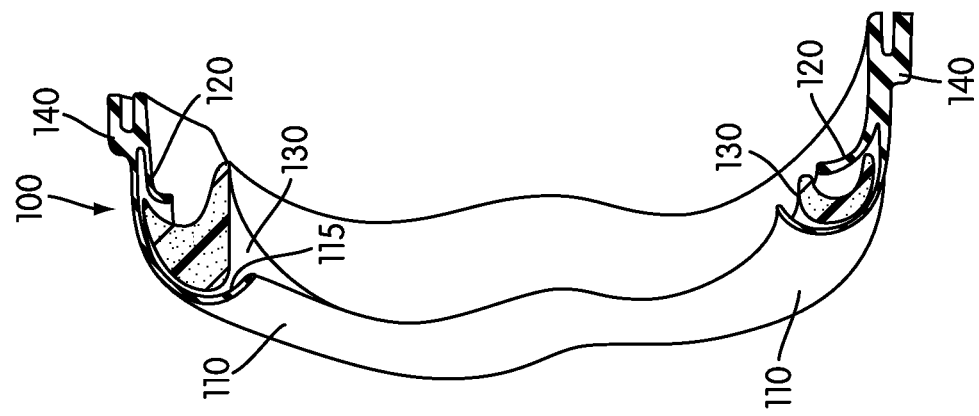
FIG. 55D is a cross section of the cushion assembly according to the first embodiment.
Figure 55C:
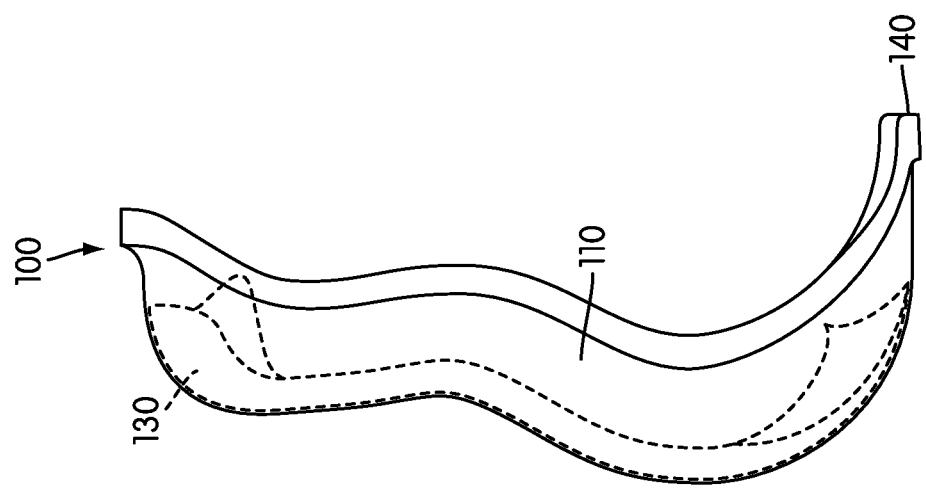
Figure 56B:
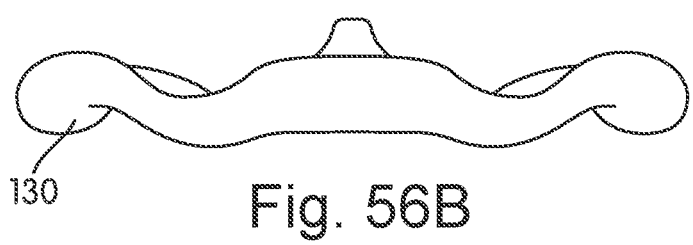
FIGS. 56A-56F are rear elevation, top plan, bottom plan, side elevation, rear perspective, and front perspective views of a flexible element of the cushion assembly according to the first embodiment.
Figure 56A:
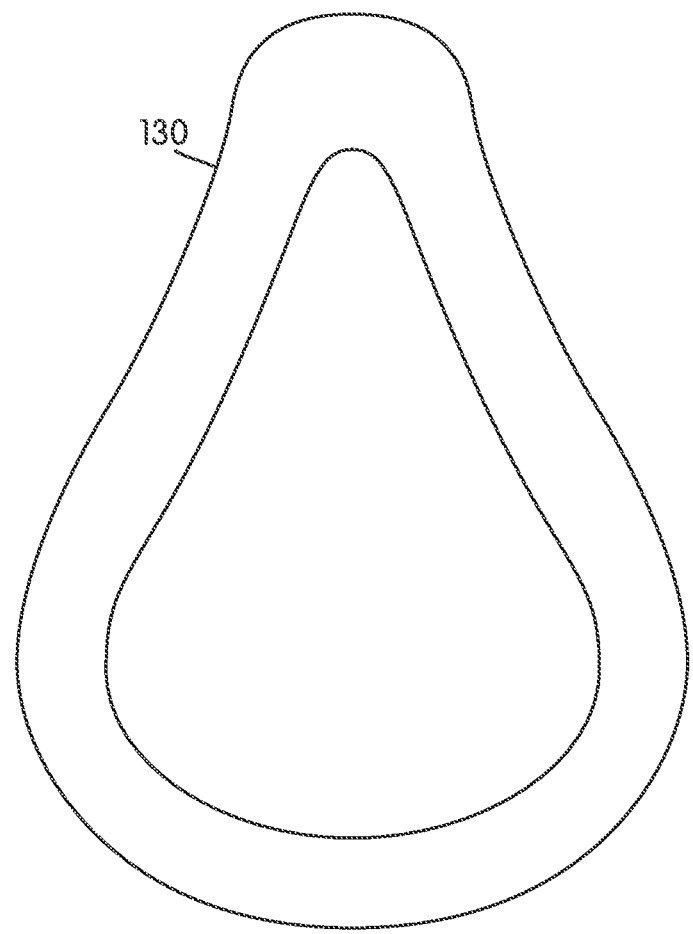
Figure 56D:
Figure 56C:
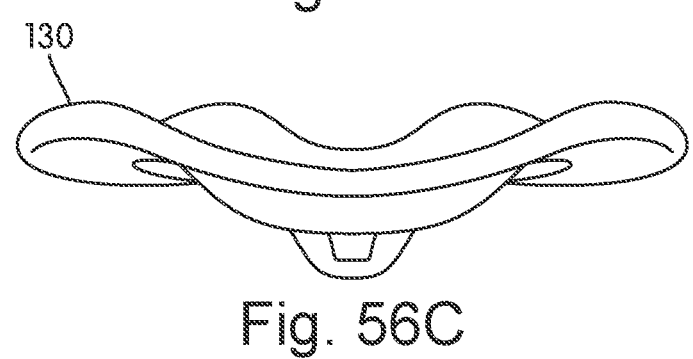
Figure 56E:
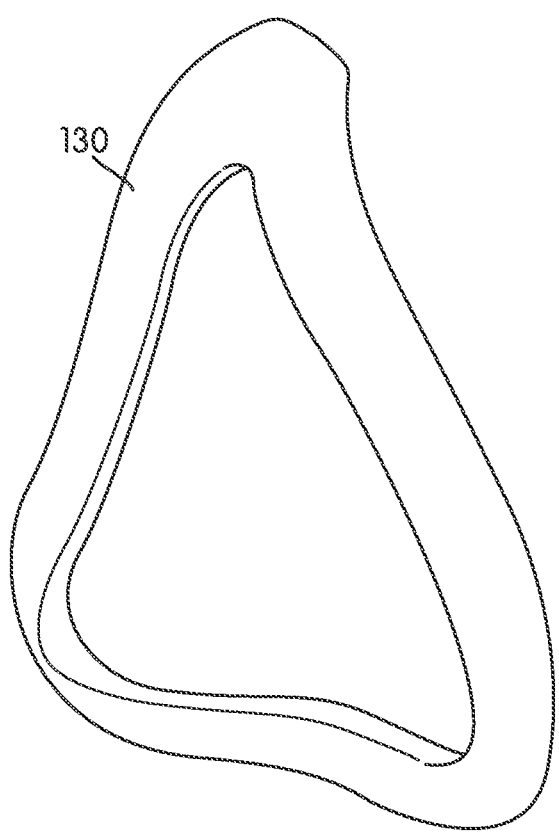
Figure 56F:
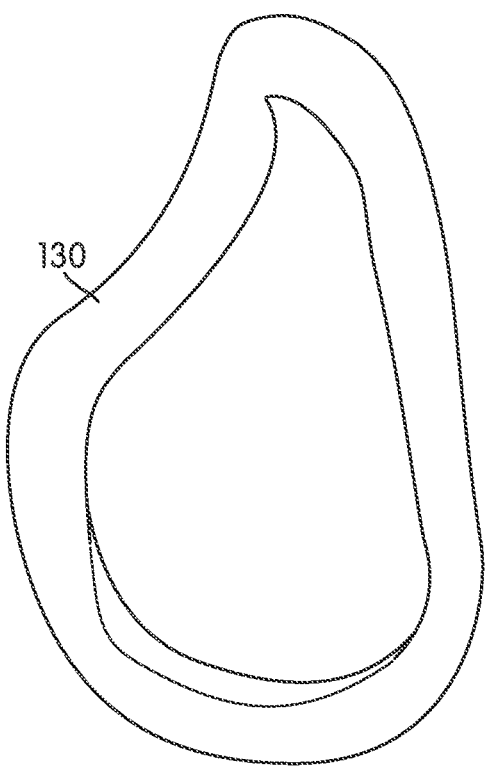

Referring to FIGS. 55A-55D, a cushion assembly 100 in accordance with a first embodiment of the present invention includes a silicone membrane 110 and an undercushion (U/C) 120, similar to that of a MIRAGE® cushion. The membrane 110 and the undercushion 120 are supported by an underlying cushion flange 140. The membrane 110 and the undercushion 120 may be formed as a one piece element with the underlying cushion flange 140. The membrane 110, the undercushion 120 and the underlying cushion flange 140 may be formed of silicone and may be formed as separate elements, or as a one-piece unit. Although not shown in the figure, the cushion flange, the membrane and the undercushion are generally triangularly shaped to match the contours of a wearer's face defined by the nasal bridge region, the cheek regions, the upper lip region (in the case of a nasal mask), or the chin region (in the case of a full face mask). As shown in FIG. 55D, the membrane 110 is generally the same shape as the undercushion 120 and surrounds the undercushion 120.

The cushion assembly 100 includes a flexible element 130 between the membrane 110 and the undercushion 120. In a preferred embodiment, the flexible element 130 is a foam insert. Referring to FIG. 55D, the flexible element 130 is placed between the membrane 110 and the undercushion 120. The flexible element 130 is supported by the undercushion 120 and provides initial soft compression of the cushion assembly 100. A flexible element in accordance with the first embodiment of the present invention is shown in FIGS. 56A-56F.

The flexible element 130 may be an insert constructed from a soft, compressible elastomer such as polyurethane foam. The flexible element 130 may also be constructed from a soft silicone, for example with a hardness of Shore A 20 or less. The flexible element 130 may further be a thermoplastic elastomer.

The flexible element 130 acts like a spring exhibiting an initial low spring constant. In addition to the flexible element 130 the undercushion 120 exhibits the characteristic of a relatively harder, or firmer, spring constant. The respective roles of each layer in the first embodiment are: (i) for the membrane 110 to cause a seal to occur between its outer surface and the user's face; (ii) for the flexible element 130 to serve as a compliance layer thereby preventing premature collapse of the membrane 110 onto the undercushion 120; and (iii) for the cushion flange 140 of the cushion assembly 100 to serve as a support layer preventing excessive movement of the membrane 110 relative to the face thereby preventing the face from contacting a frame, body or shell of the mask or otherwise moving relative to the membrane 110 such as to compromise the seal.

The flexible element 130 is shaped to track the cavity between the membrane 110 and the undercushion 120 of the cushion assembly 100. The spacing of the flexible element 130 is relative to the membrane inner surface 115 such that there is still capacity for the membrane 110 to billow outwards to seal against the patient's face.

Figure 57A:
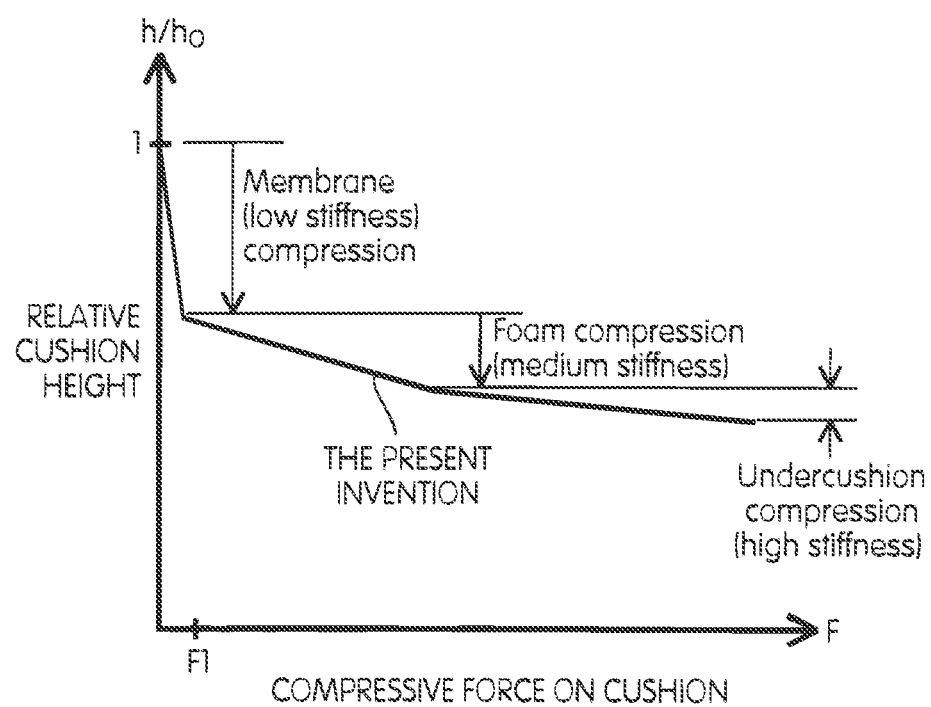
FIGS. 57A-57C are graphical illustrations of mechanical properties of the cushion assembly according to the first embodiment, a MIRAGE® cushion, and an ACLAIM cushion, respectively.
Figure 57B:
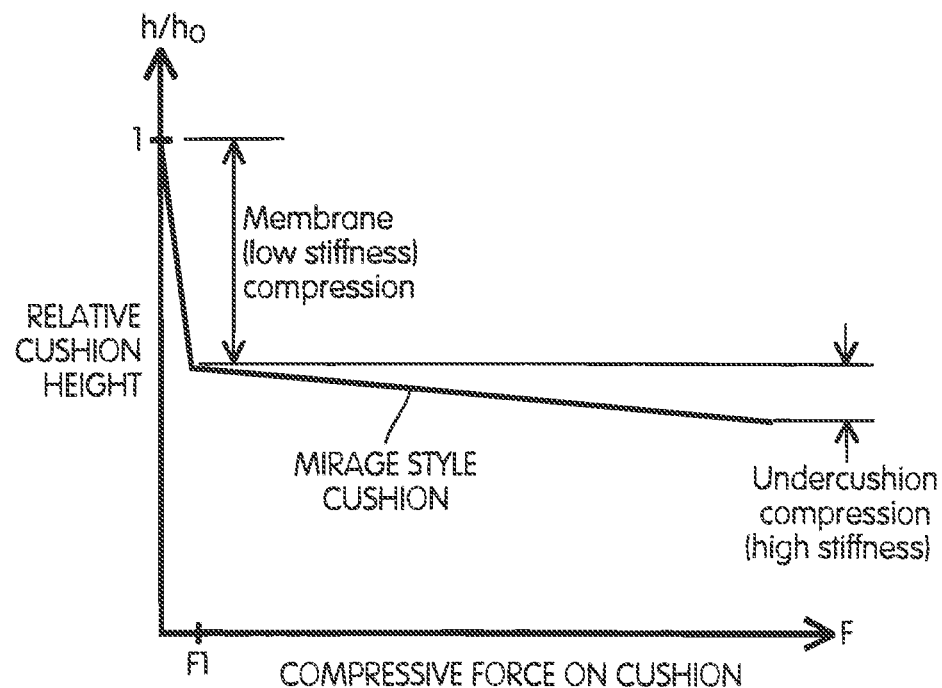
Figure 57C:
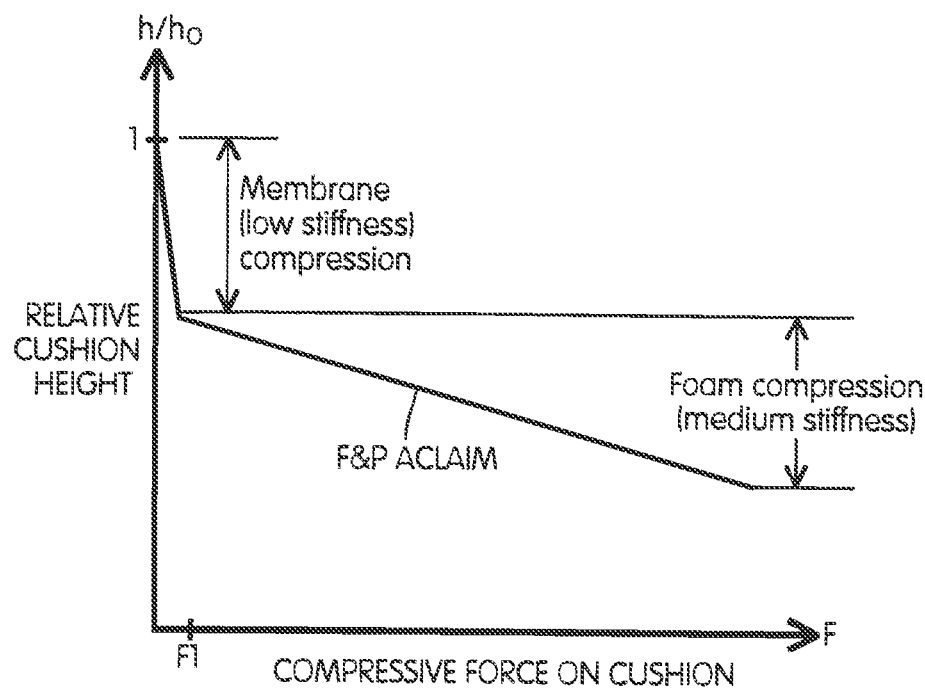
Figure 58:
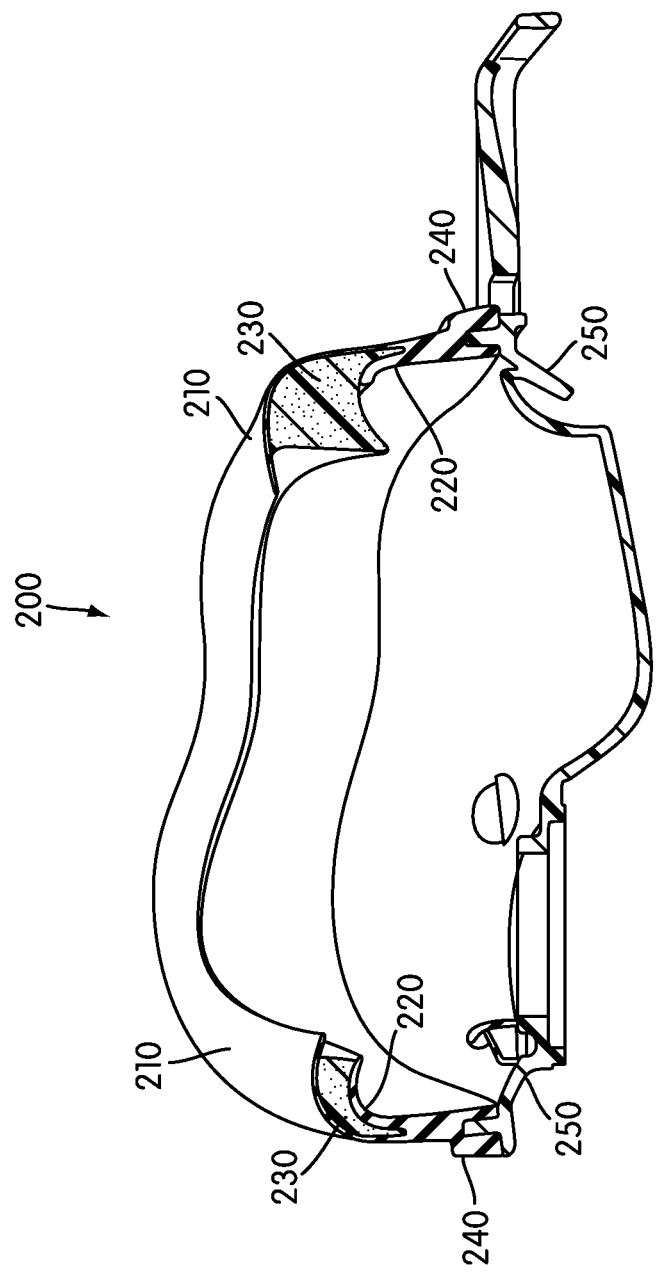
FIG. 58 is a cross section of a cushion assembly according to a second embodiment of the present invention.
Figure 59A:
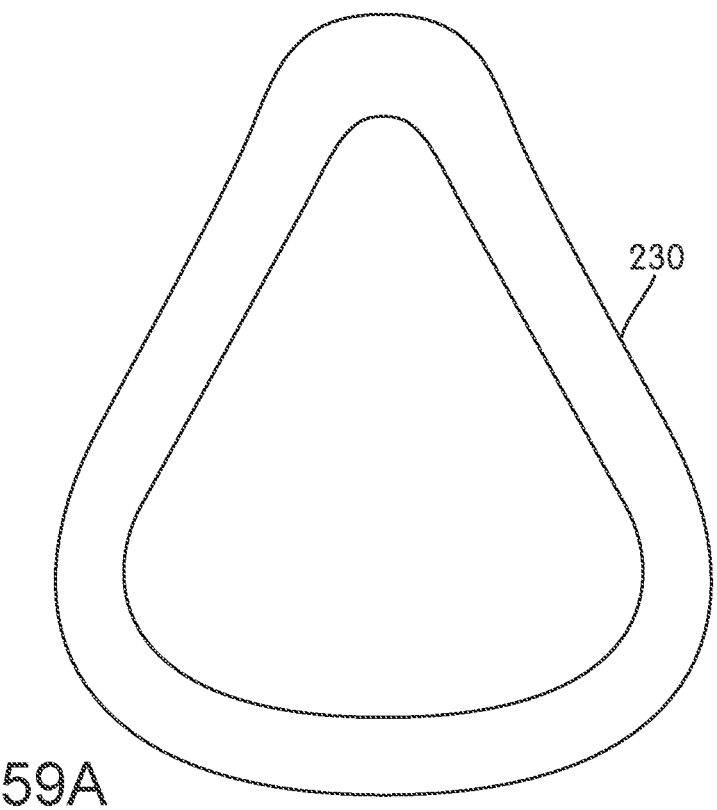
FIGS. 59A-59E are front elevation, rear elevation, side elevation, front perspective, and rear perspective views of a flexible element of the cushion assembly according to the second embodiment.
Figure 59B:
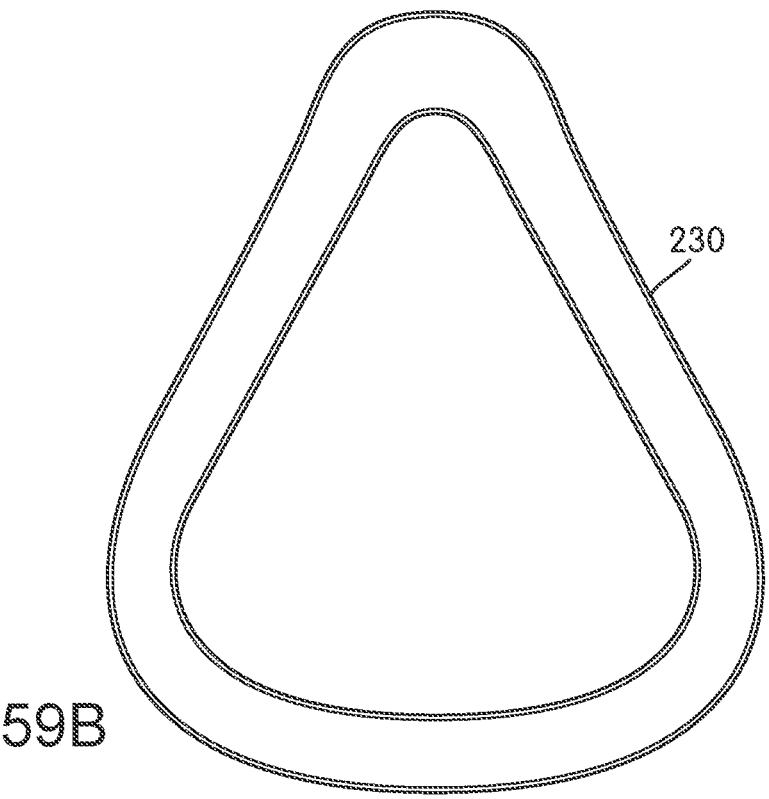
Figure 59C:
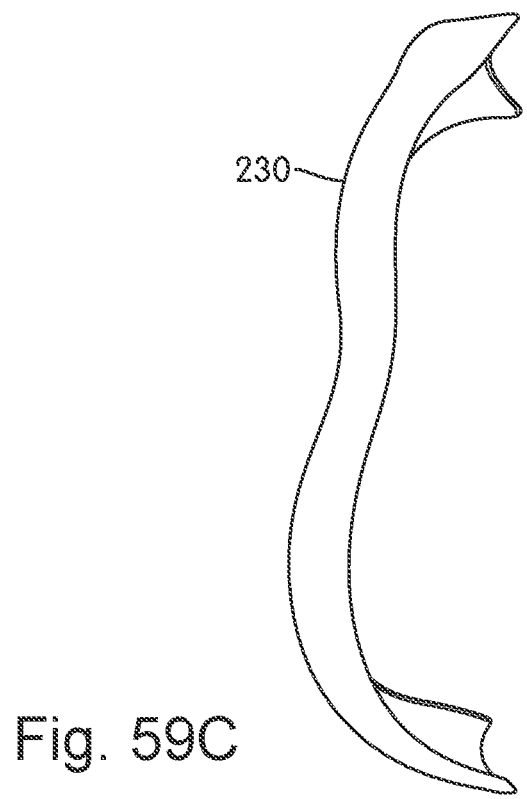
Figure 59D:
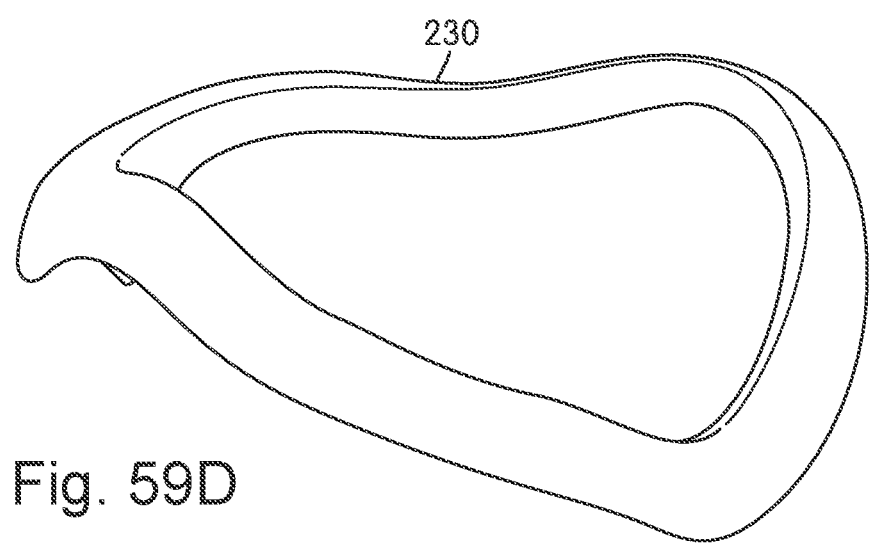
Figure 59E:
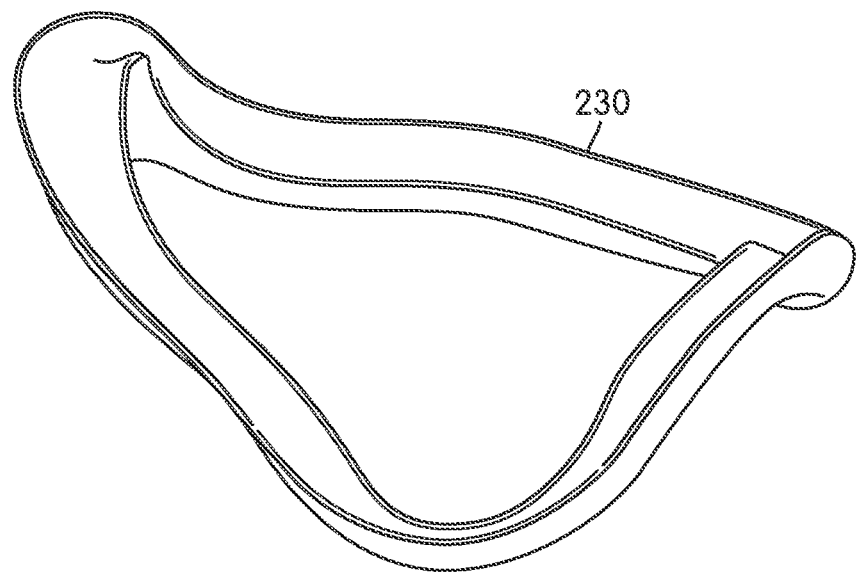

FIGS. 57A-57C illustrate mechanical properties of the cushion assembly 100 (FIG. 57A) in comparison to the mechanical properties of the MIRAGE® cushion (FIG. 57B) and the ACLAIM cushion (FIG. 57C). The y-axis represents relative cushion height h/ho. When the cushion assembly 100 is at its original height ho, the relative cushion height is 1. If the cushion assembly 100 is compressed to half its original height, the relative cushion height would be 0.5. The x-axis represents the compressive force F on the cushion assembly 100. The force F may be the resultant force on the cushion assembly 100 being used between the mask shell and a patient's face.

Referring to FIGS. 58 and 59A-59F, a cushion assembly 200 according to a second embodiment of the present invention includes a membrane 210, a flexible undercushion (or elastomeric support portion) 220 with an elastomeric side wall that terminates in a resiliently flexible and inwardly extending lip, a flexible element 230, and an underlying cushion flange 240 that forms part of the elastomeric side wall. An outer perimeter of the flexible element 230 is anchored to the side wall of the undercusion 220. In addition, an inner perimeter of the flexible element 230 remains unsupported. The membrane 210 and the undercushion 220 may be formed as a one-piece unit with the underlying cushion flange 240. The underlying cushion flange 240 is attachable to a mask frame or shell 250 at a rear edge of the underlying cushion flange 240 at a connection interface. In a preferred embodiment, the flexible element 230 is a foam insert. The flexible element 230 may also be formed of silicone.

Figure 60A:
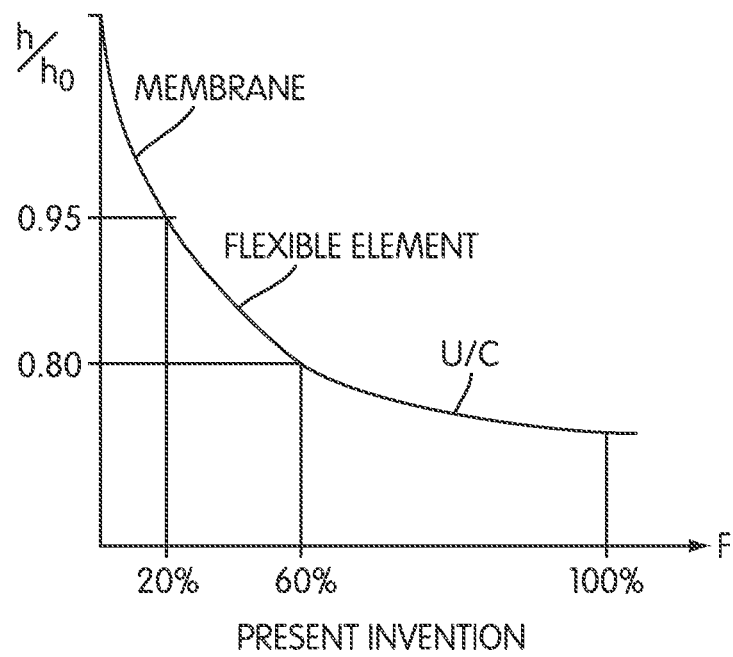
FIGS. 60A-60D are graphical illustrations of mechanical properties of the cushion assembly according to the second embodiment, a MIRAGE® cushion, an ACLAIM cushion, and a comparison of the mechanical properties of the three cushions, respectively.
Figure 60B:
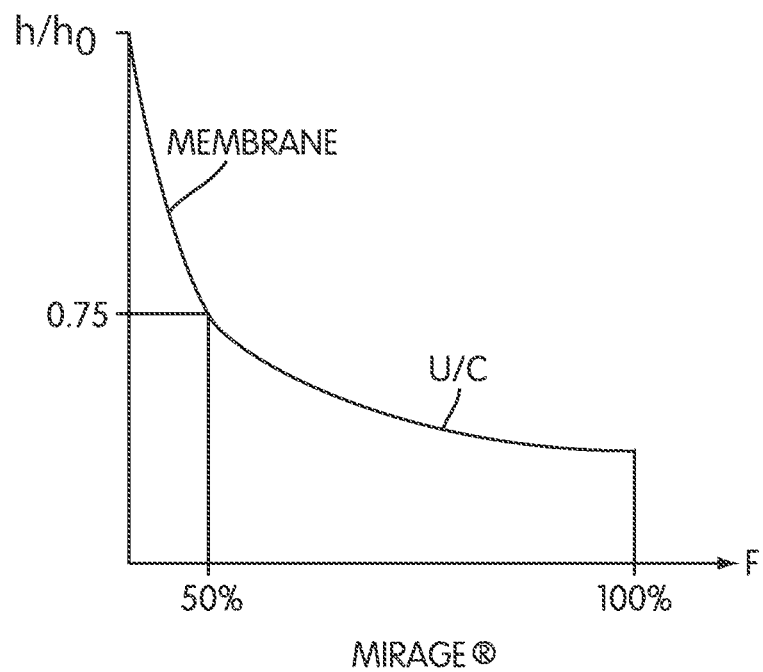
Figure 60C:
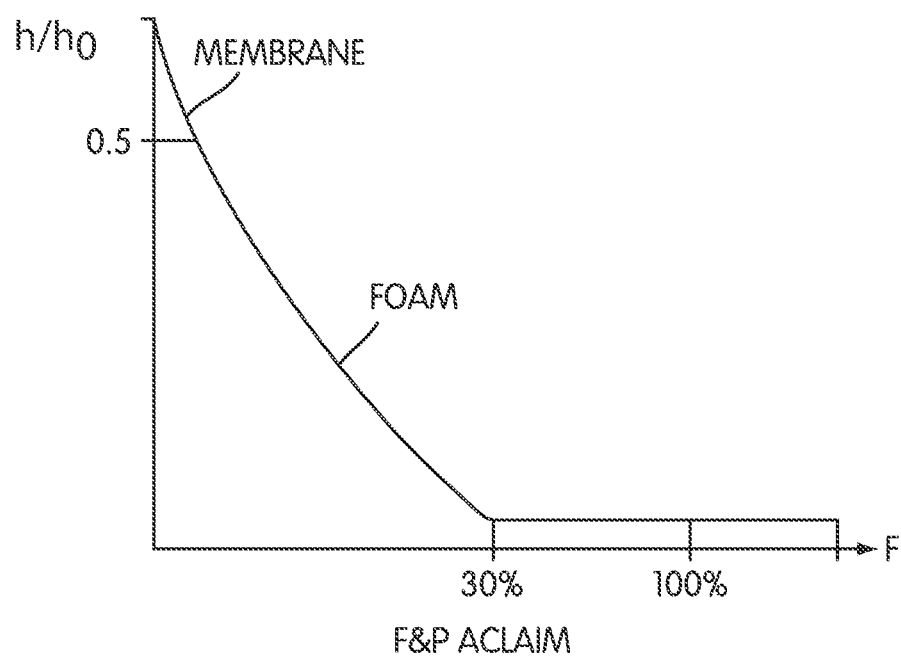
Figure 60D:
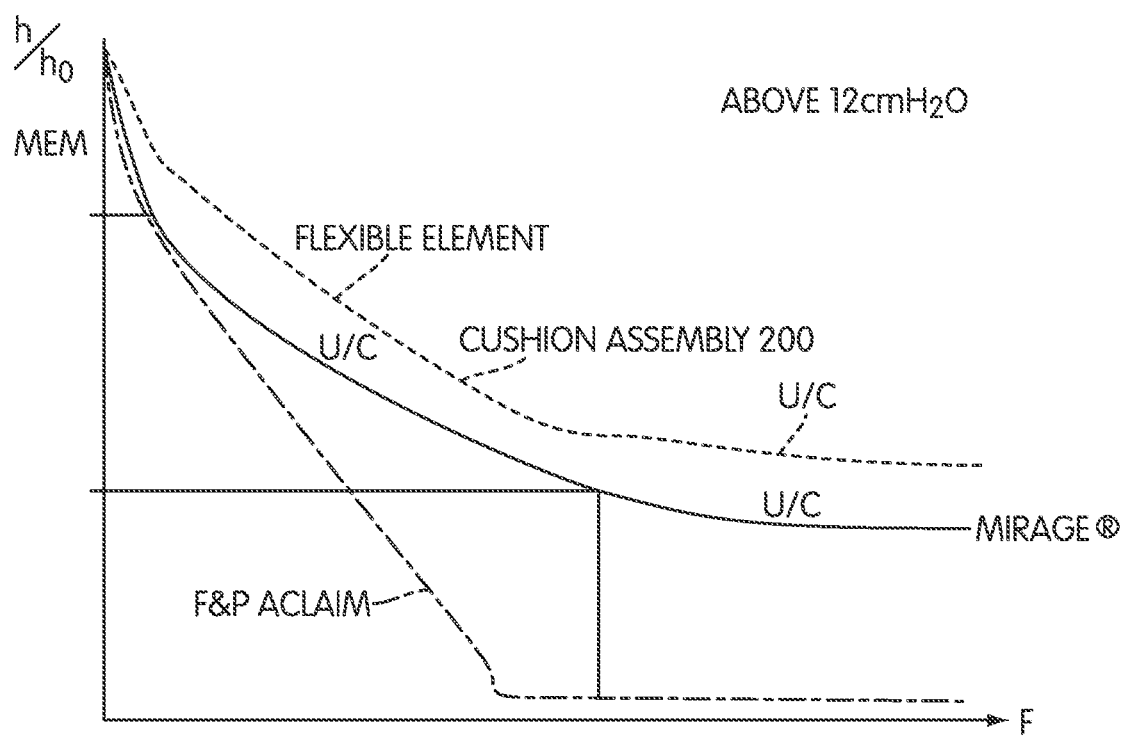

FIGS. 60A-60C illustrate mechanical properties of the cushion assembly 200 in accordance with the second embodiment of the invention, the MIRAGE® cushion and the ACLAIM cushion, respectively. FIG. 60D illustrates a comparison of the three cushions on a single set of axes. The y-axis represents the relative cushion height h/ho and the x-axis represents the compressive force F on the cushion. The compressive forces are represented as a percent of a maximum compressive force applied to the cushion assembly.

Referring to FIG. 60A, in the initial zone, which largely corresponds to the membrane 210, the cushion height is reduced to about 95% by a compressive force of about 20% of the maximum force. In the second zone, which corresponds to the flexible element 230 of the cushion assembly 200, compression goes from 95% to 80% by a compressive force of about 60% of the maximum force. In the third zone, which corresponds to the undercushion 220, increasing the force up to 100% of maximum only slightly further compresses the cushion assembly 200.

FIG. 60B illustrates mechanical properties of a MIRAGE® cushion. Compression of about 75% is achieved by a force of about 50% of maximum in the zone corresponding to the membrane. Further increases in the compressive force results in only slight decreases in the cushion relative height, corresponding to compression of the undercushion.

FIG. 60C illustrates mechanical properties of an ACLAIM cushion assembly. An initial compression to about 90% is achieved relatively easily with low force. Thereafter, further increases in the compressive force lead to large compression of the foam insert by about 30% of the maximum force. Application of a compressive force above 30% of maximum results in very slight, or almost no compression of the ACLAIM cushion assembly as the foam insert is completely compressed against the mask shell.

FIG. 60D illustrates a comparison of the three previous curves on one set of axes.

FIG. 61 is a graphical representation of the functioning of the cushion assemblies 100, 200 according to the first and second embodiments by analogizing the flexible element 130, 230 and the undercushion 120, 220, respectively, to springs. The spring constant of the flexible element 130, 230 is smaller than the spring constant of the undercushion 120, 220. As shown in FIG. 61, the flexible element 130, 230 acts as a soft spring to initially take up a compressive force on the cushion assembly. The flexible element 130, 230 enhances the soft feel of the cushion assembly 100, 200 and enhances conformance of the cushion assembly 100, 200 to the wearer's face, thus improving the seal and reducing, or eliminating, leaks.

As the compressive force on the cushion assembly 100, 200 increases, the stiffer undercushion 120, 220 subsequently begins to compress. The undercushion 120, 220 reduces, or eliminates, the possibility of the wearer's face from contacting the mask shell.

Figure 62:
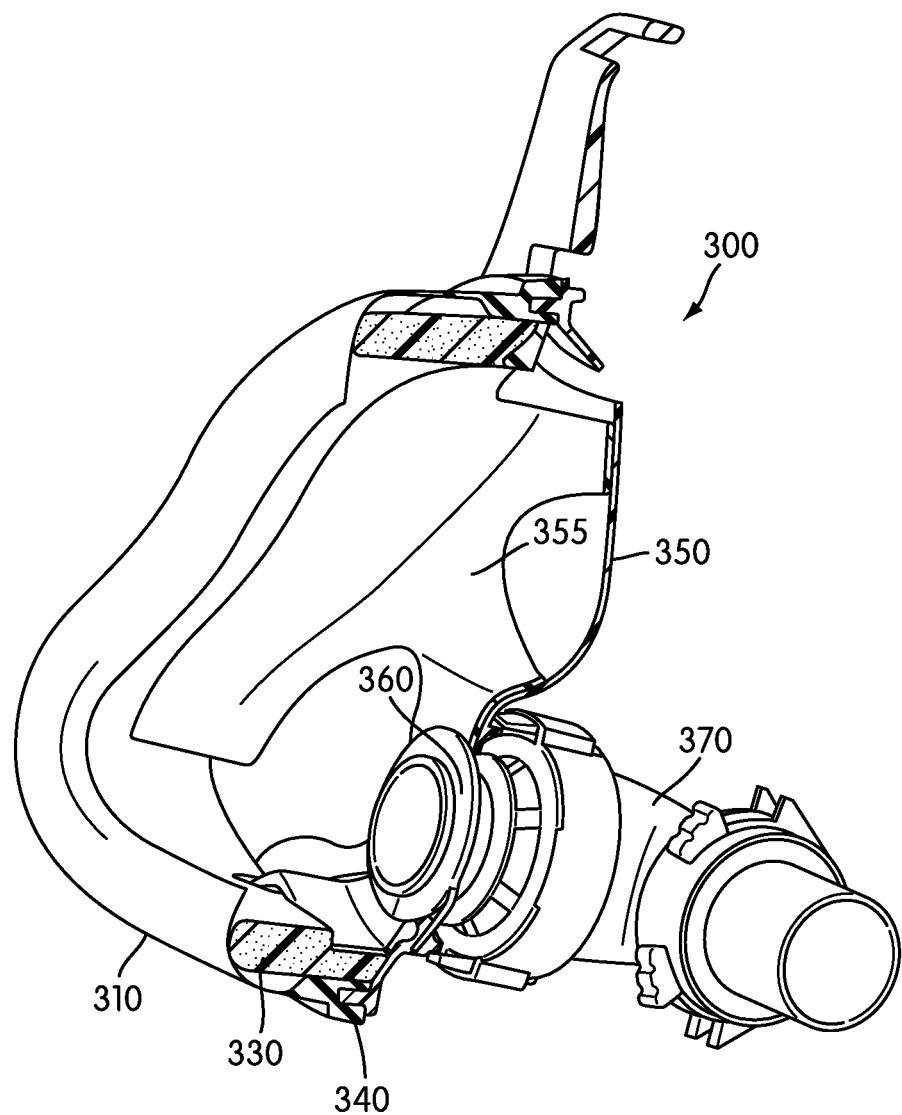
FIG. 62 is a perspective view of a cushion assembly according to a third embodiment of the present invention.

Referring to FIG. 62, a cushion assembly 300 according to a third embodiment of the present invention includes a membrane 310 that extends from an underlying cushion flange 340. The underlying cushion flange 340 is attached at a rear end thereof to a mask shell 350. A flexible element 330 is disposed between the membrane 310 and the underlying cushion flange 340. The flexible element 330 of this embodiment is generally taller, or deeper, than the flexible elements of the first and second embodiments. The flexible element 330 in this embodiment is made of one material. The cushion flange 340 does not include an undercushion. In this embodiment, the membrane 310 achieves the primary seal and is supported by the flexible element 330, which distributes the compressive forces at various locations resulting in a more comfortable mask system.

Figure 63A:
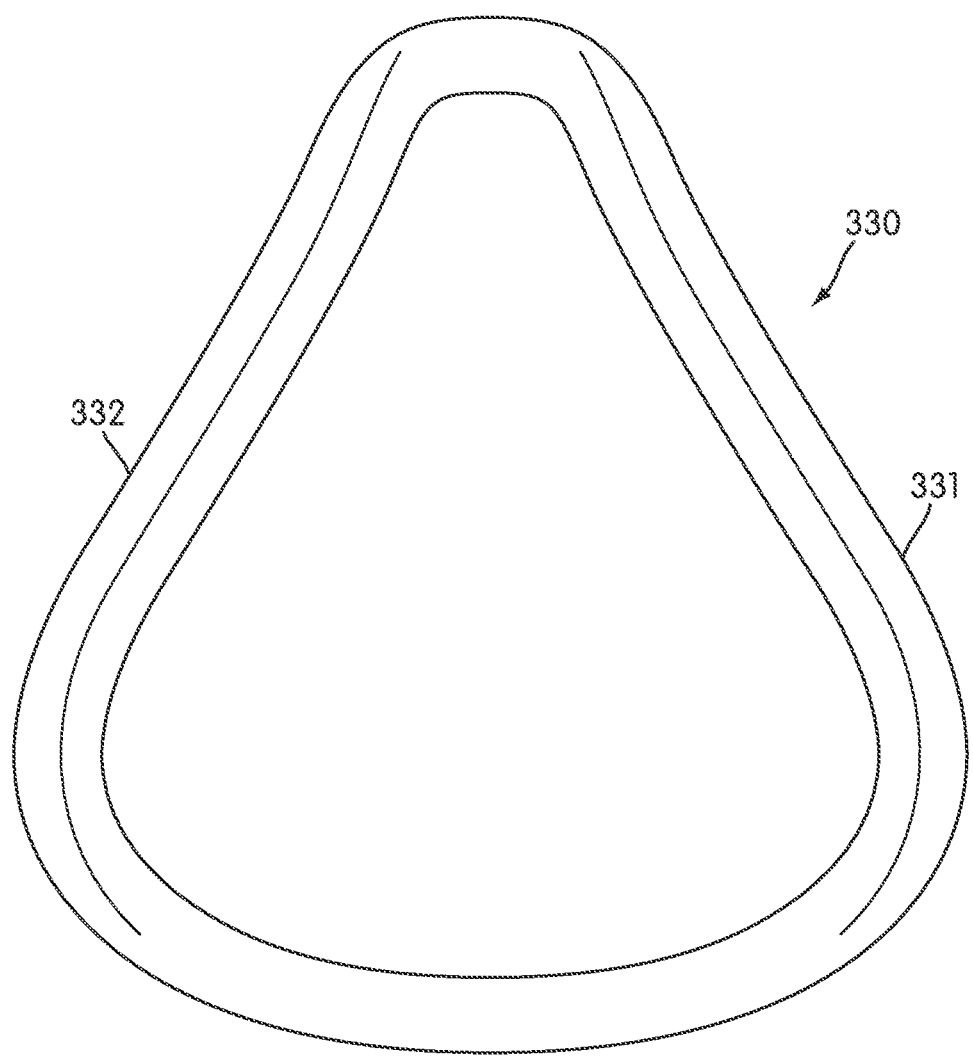
FIGS. 63A-63E are front elevation, rear elevation, side elevation, front perspective, and rear perspective views, respectively, of a flexible element of the cushion assembly according to the third embodiment.
Figure 63B:
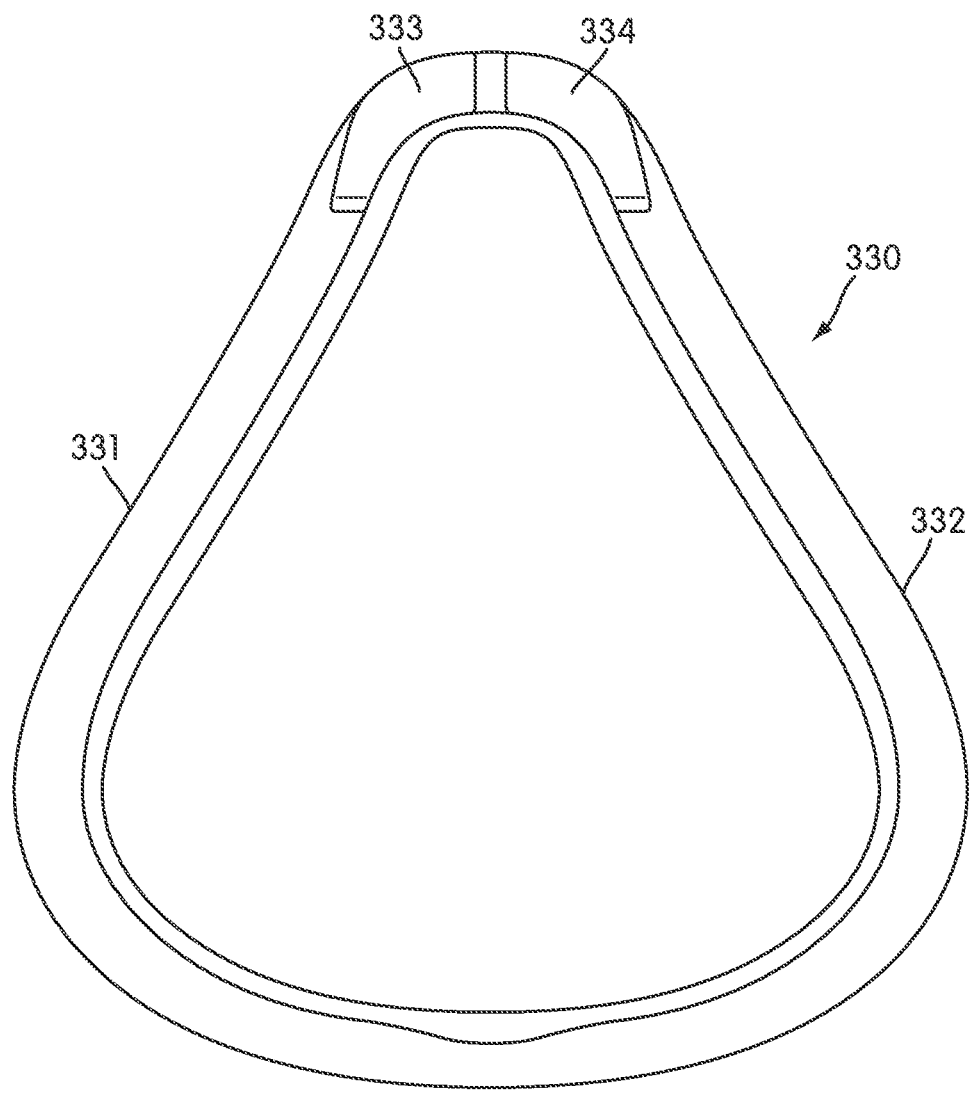
Figure 63C:
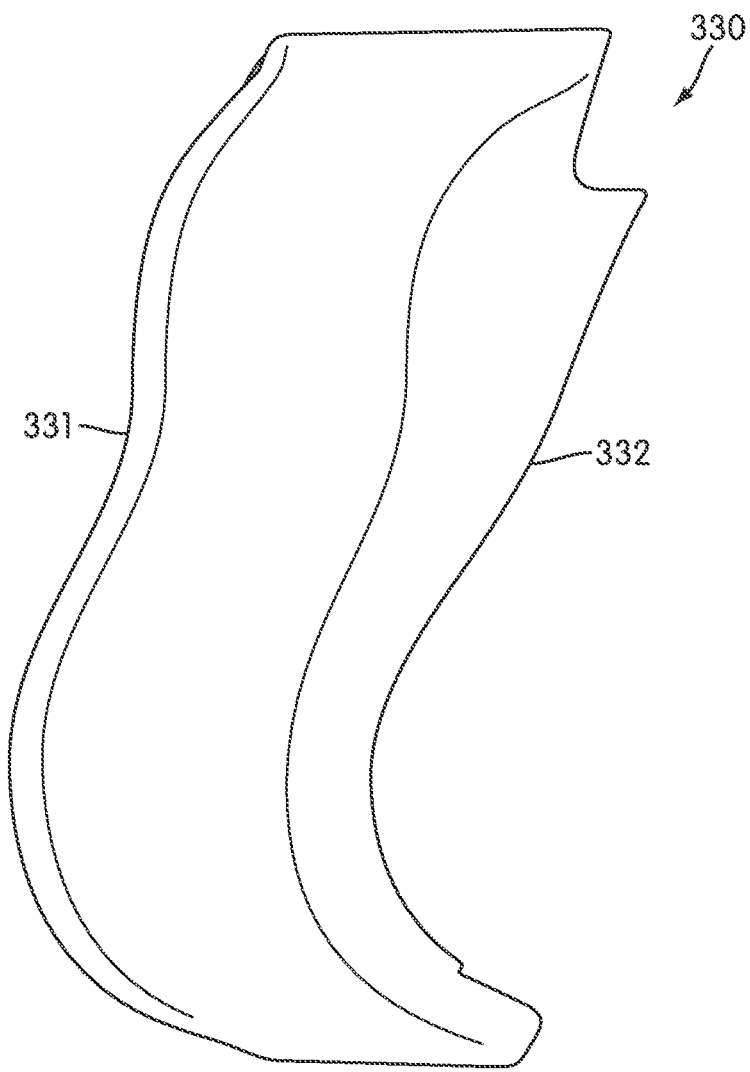
Figure 63D:
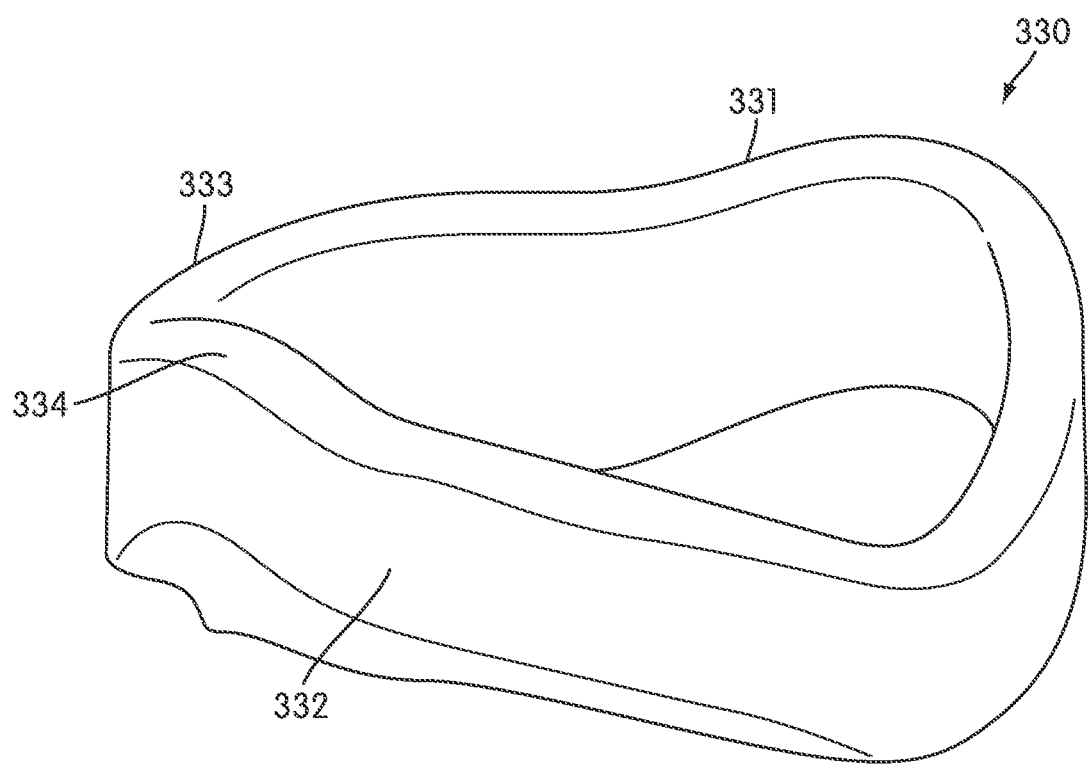
Figure 63E:
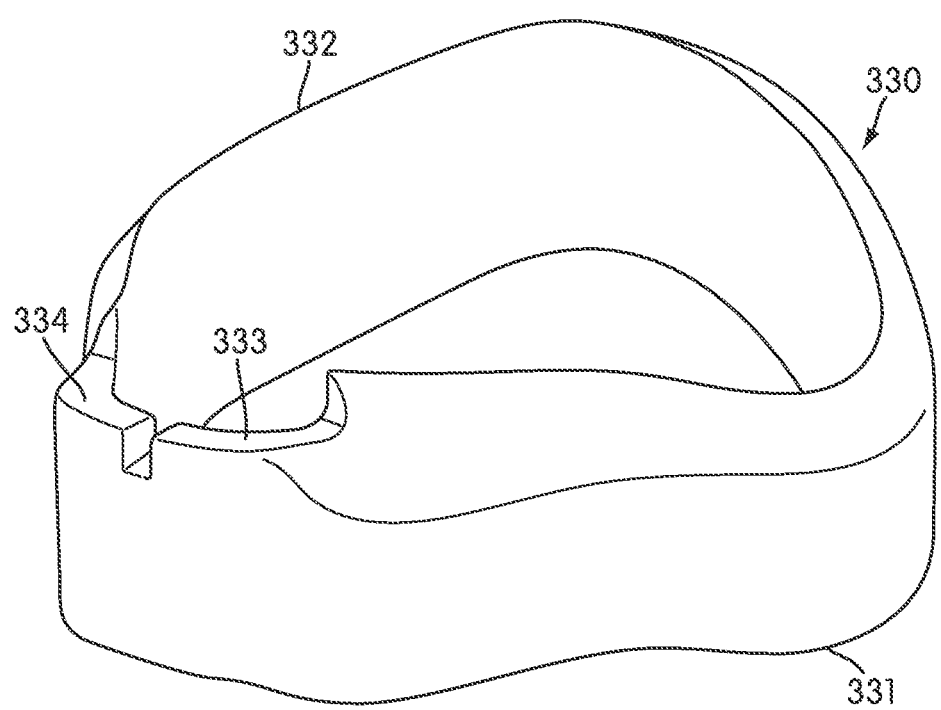
Figure 64A:
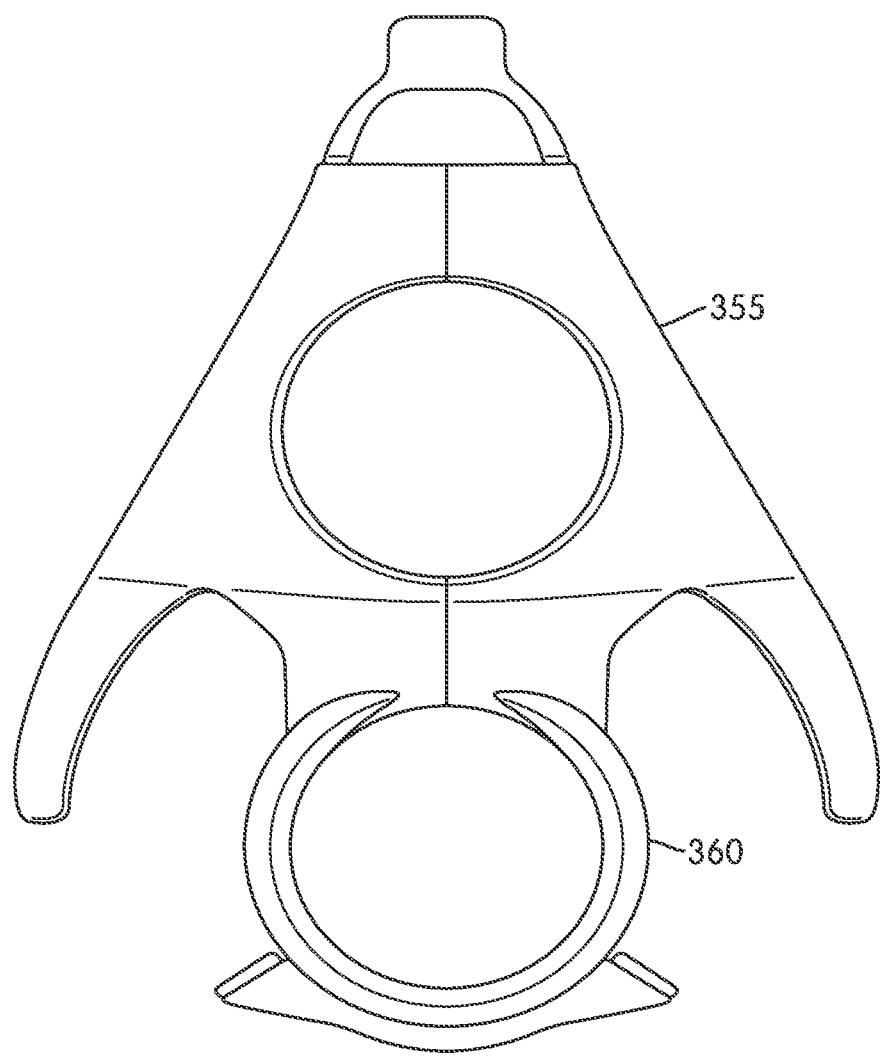
FIGS. 64A-64E are front elevation, rear elevation, side elevation, front perspective, and rear perspective views, respectively, of a retainer of the cushion assembly according to the third embodiment.
Figure 64B:
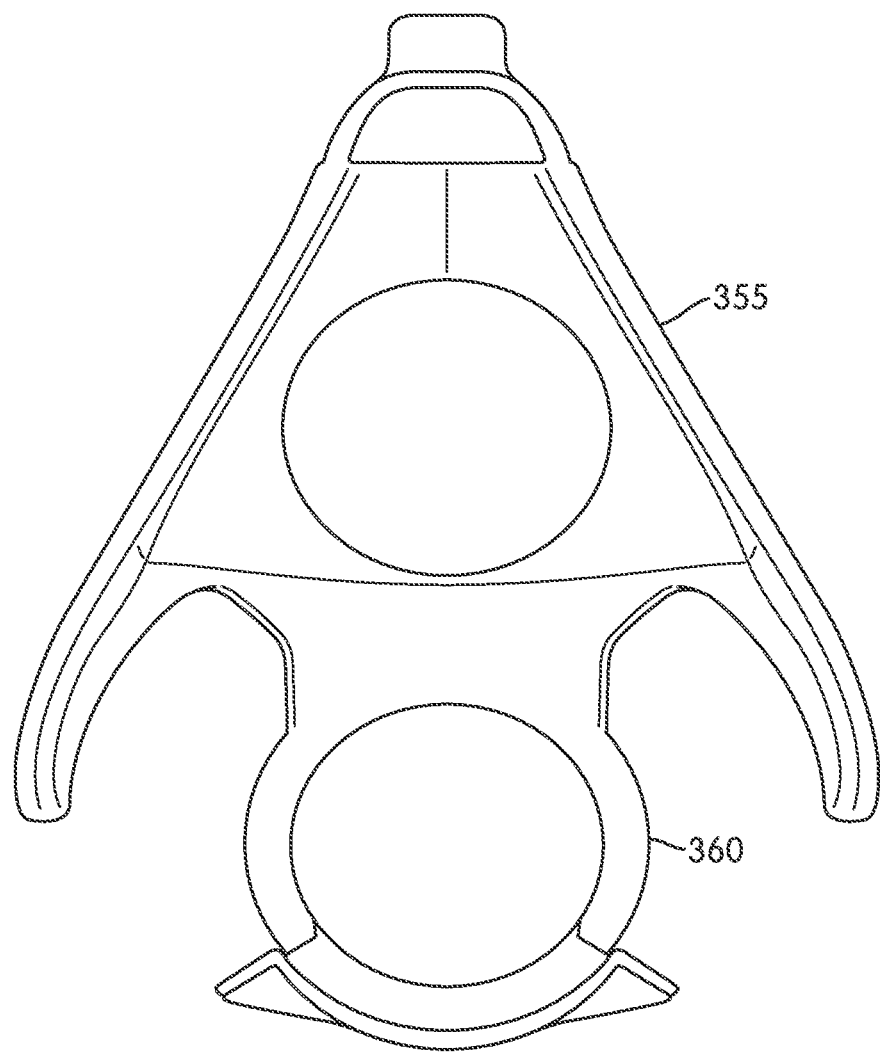
Figure 64C:
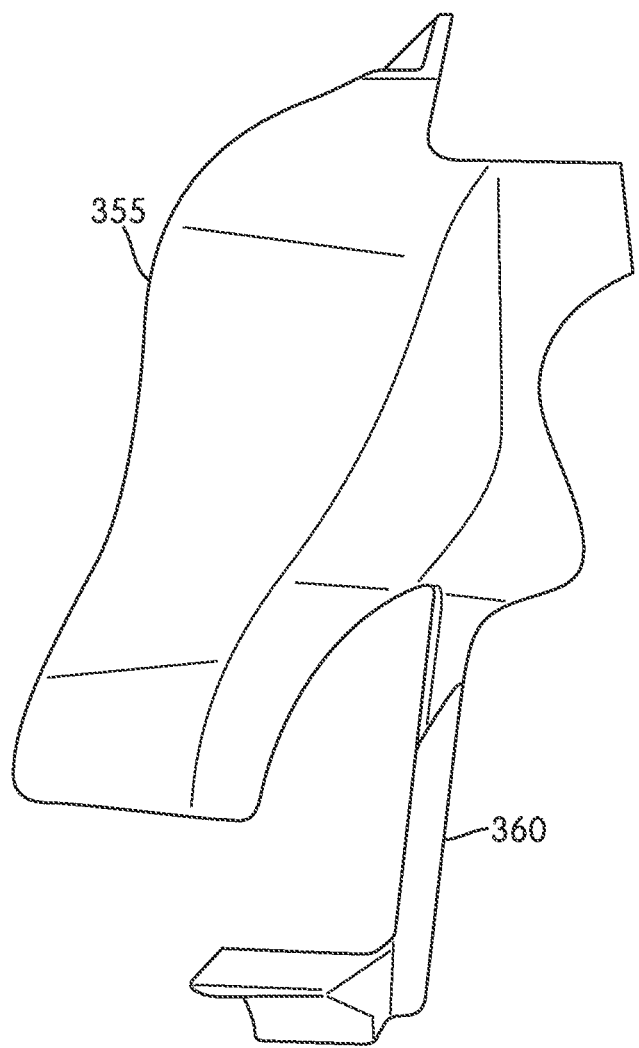
Figure 64D:
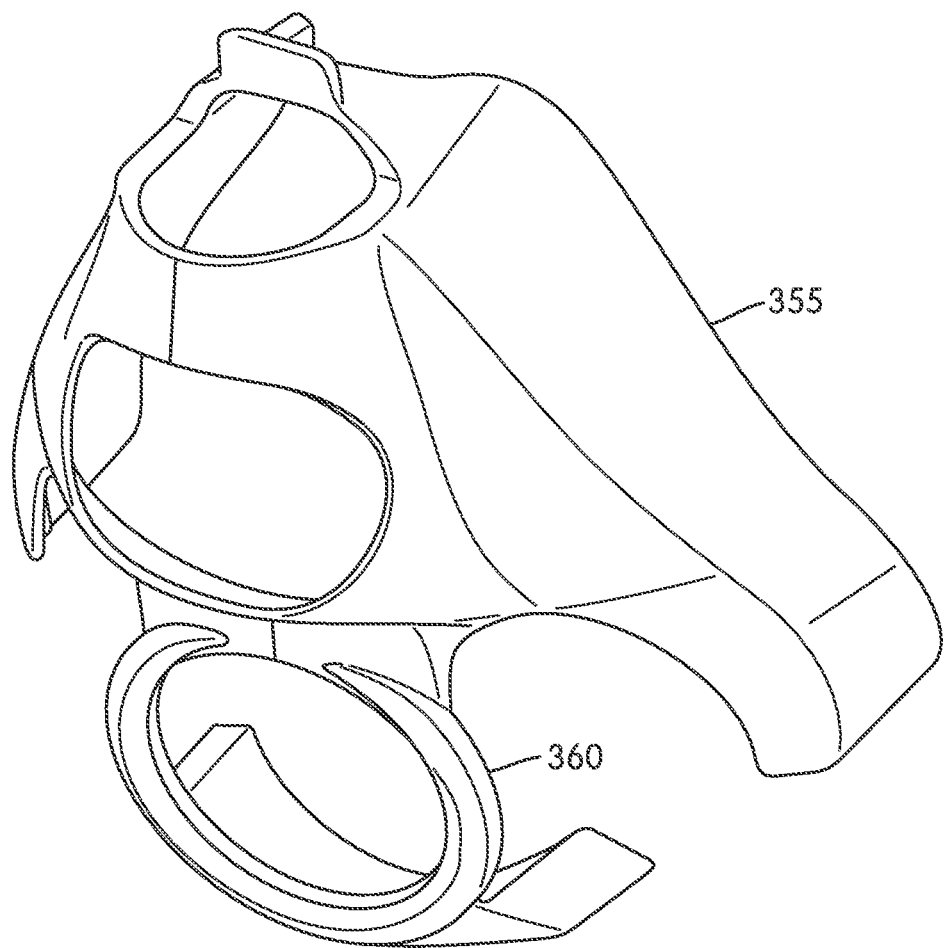
Figure 64E:
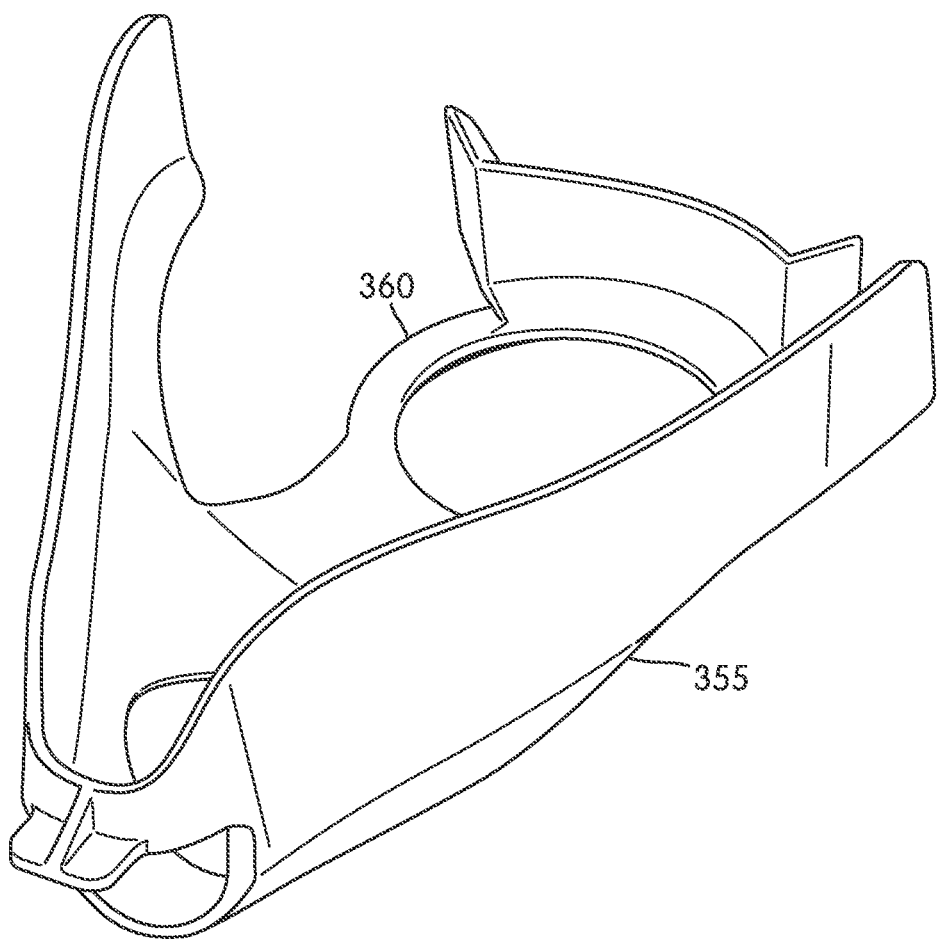

Further views of the flexible element 330 are shown in FIGS. 63A-63E. In this embodiment, the flexible element 330 includes multiple segments 331, 332, 334, 335 of different properties (force deflection characteristics). As shown in FIG. 63B, which illustrates the rear side of the flexible element 330, the segments 333 and 334 may be placed in the nasal bridge region of the mask. The segments 333 and 334 may be of different sizes and shapes and different spring constants (i.e. stiffnesses) to accommodate differences in sizes and shapes of individual wearers. It should be appreciated that the segments 331, 332, 333, 334 may be of varying sizes, shapes and spring constants to accommodate differences in the sizes and shapes of individual wearers. It should also be appreciated that any number of segments may be used.

The flexible element 330 is supported by a rigid retainer 355. The retainer 355 holds the flexible element 330 during assembly of the cushion assembly 300 and the mask. The flexible element 330 and the retainer 355 may be joined together and used as a sub-assembly. The retainer 355 may also include an extension having an elbow retainer clip 360. The elbow retainer clip 360 retains a rotating elbow 370 required for the supply of air from a flow generator. Further views of the retainer are shown in FIG. 64A-64E.

Figure 65:
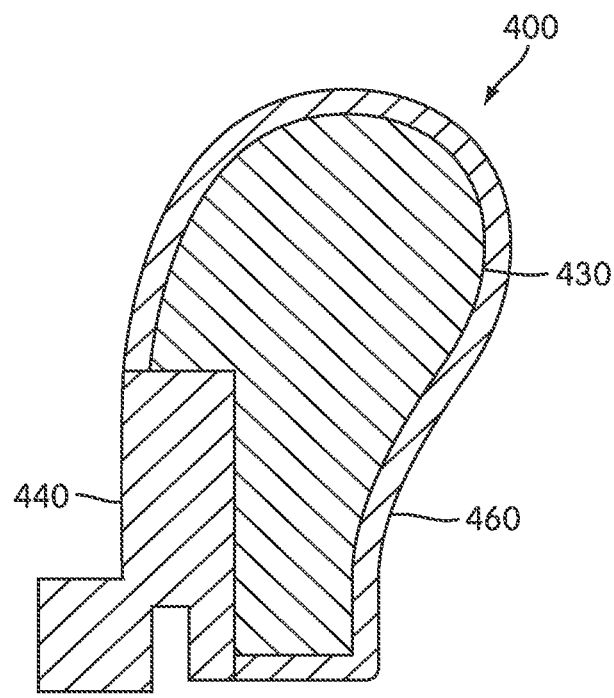
FIG. 65 is a cross section of a cushion assembly according to a fourth embodiment of the present invention.

Referring to FIG. 65, a cushion assembly 400 according to a fourth embodiment of the present invention includes a two or three layer structure. The first layer is composed of a cushion flange 440. A front side of the cushion flange 440 is adapted to engage with a shell of a mask. The second layer is composed of flexible element 430 connected to the cushion flange 440. The flexible element 430 defines a cushion shape and forms a face-engaging structure. The flexible element 430 may be provided with a third layer composed of a skin 460.

The first layer (cushion flange 440) may be a rigid layer of polyurethane elastomer (no foam). The second layer (flexible element 430) may be formed of urethane foam or soft silicone. The third layer (skin 460) may be formed of silicone skin. Preferably, the skin 460 would have a thickness of 0.2 to 0.6 mm either uniform or varying according to load or the expected degree of deformation required.

Figure 66:
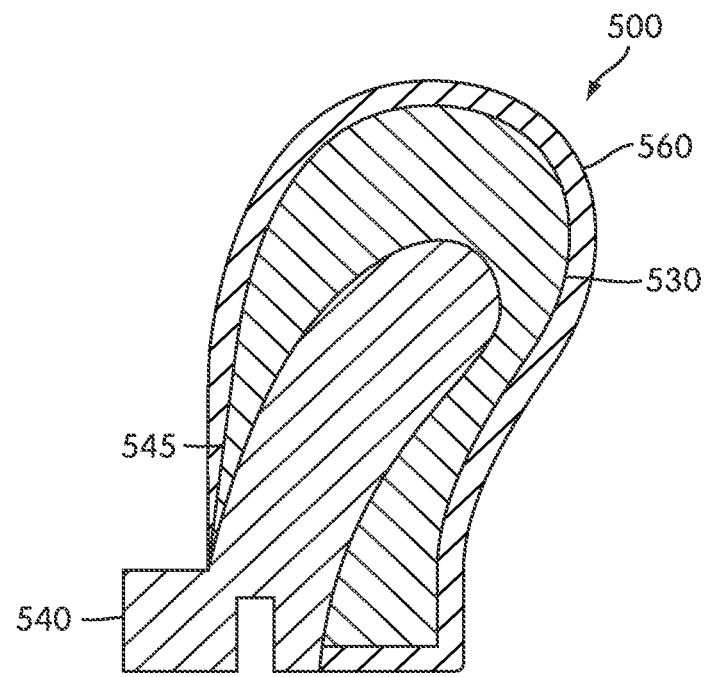
FIG. 66 is a cross section of a cushion assembly according to a fifth embodiment of the present invention.

Referring to FIG. 66, a cushion assembly 500 according to a fifth embodiment of the invention includes a two or three layer structure. The first layer is composed of a cushion flange 540. A front side of the cushion flange 540 is adapted to engage with a shell of a mask. The cushion flange 540 includes a supporting portion 545 that extends from the front side towards the rear side. The supporting portion is flexible and acts in a manner similar to the undercushion described above. The second layer is composed of a flexible element 530 that is attached to the cushion flange 540 and surrounds the supporting portion 545. The flexible element 530 defines a cushion shape and forms a face-engaging structure. The flexible element 530 may be provided with a third layer composed of a skin 560.

The first layer (cushion flange 540) may be a rigid polyurethane elastomer (no foam). The second layer (flexible element 530) may be formed of urethane foam or soft silicone. The third layer (skin 560) may be formed of silicone skin with a uniform or varying thickness as described above.

In use, the flexible element 530 begins to compress upon contact with the wearer's face and application of a compressive force. As the compressive force increases, the flexible element 530 is further compressed until completely compressed against the supporting portion 545. Further application of compressive force results in compression of the supporting portion 545. The flexible element 530 and the supporting portion thus act as two springs in a manner similar to that illustrated in FIG. 61.

Figure 67:
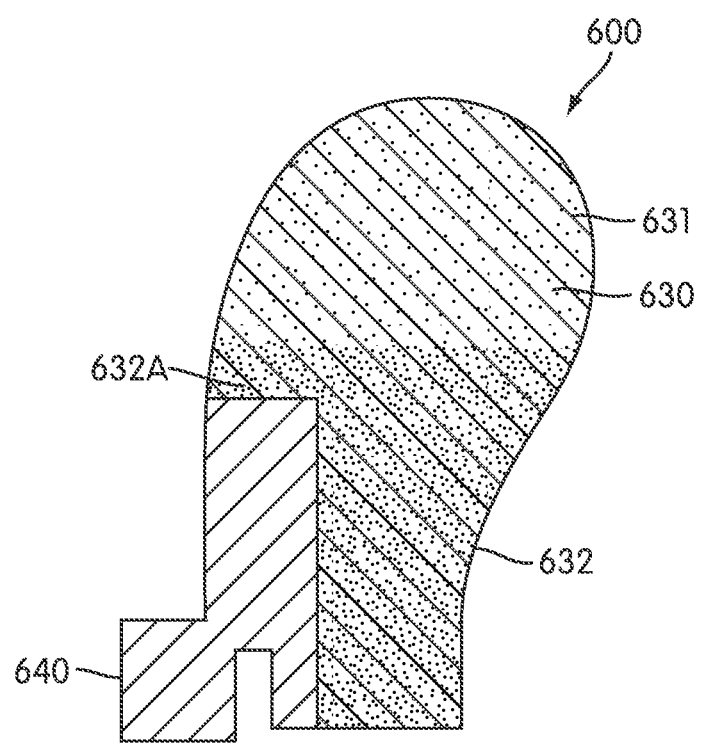
FIG. 67 is a cross section of a cushion assembly according to a sixth embodiment of the present invention.

Referring to FIG. 67, a cushion assembly 600 according to a sixth embodiment of the present invention includes a first layer and a second layer. The first layer is composed of a cushion flange 640. A front side of the cushion flange 640 is adapted to engage with a shell of a mask. The second layer is composed of flexible element 630 connected to the cushion flange 640. The flexible element 430 defines a cushion shape and forms a face-engaging structure.

The first layer (cushion flange 640) may be a rigid polyurethane elastomer (no foam). The second layer (flexible element 630) is formed of foam and includes a first portion 631 of relatively low stiffness and a second portion 632 of relatively high stiffness. The different stiffnesses may be provided by forming the flexible element of foam having different densities, as indicated by the relative spacing of dots in the first and second portions 631 and 632. The flexible element 630 may be a single piece having varying density, or multiple pieces with different densities. Although the flexible element 630 is shown in FIG. 67 as having two different stiffnesses (densities), it should be appreciated that the flexible element 630 may be formed with more than two stiffnesses (densities). As shown in FIG. 67, the second portion 632 includes a region 632*a* that extends beyond the cushion flange 640 to prevent the wearer's face from pressing up against the cushion flange 640.

In use, the first portion 631 of the flexible element 630 begins to compress upon contact with the wearer's face and application of a compressive force. As the compressive force increases, the first portion 631 may be completely compressed whereupon the second portion 632 will begin to compress. As the second portion 632 is stiffer than the first portion 631, the decrease in the relative height of the cushion assembly 600 caused by application of the compressive force will be less in the second region 632 than in the first region 631.

Although not shown in FIG. 67, it should be appreciated that the cushion assembly 600 may be provided with a third layer, such as a skin.

Figure 68:
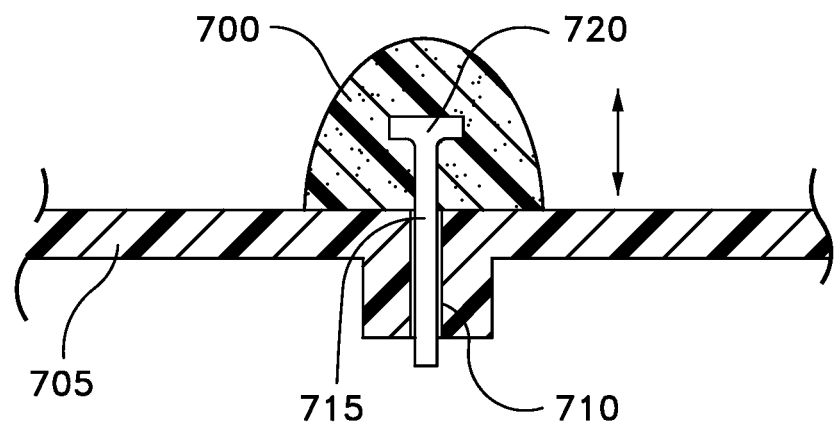
FIGS. 68 and 69 illustrate an embodiment of the present invention in which the stiffness of the cushion can be selectively varied.
Figure 69:
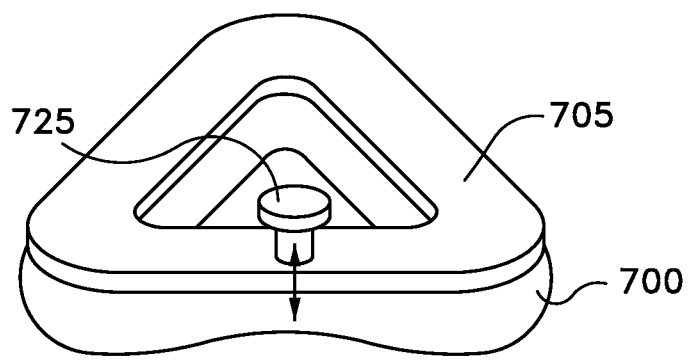

FIGS. 68 and 69 illustrate another embodiment of the present invention. A foam cushion 700 is provided to a frame 705. The frame includes an aperture 710 through which a support rod 715 is inserted. The aperture 710 and support rod 715 may be threaded with one another such that the position of a head portion 720 of the rod 715 may be moved as indicated by the double ended arrow. As shown in FIG. 69, the frame 705 may be provided with a knob 725 to allow movement of the rod 715. Although the frame 705 is only shown to include one adjustment rod 715, multiple such arrangements could of course be provided. Adjustment of the position of the rod 715 allows the cushion topography to be modified for a given pressure range.

FIGS. 70-79 illustrate cross-sectional views of additional embodiments of foam cushions according to the present invention.

Figure 70:
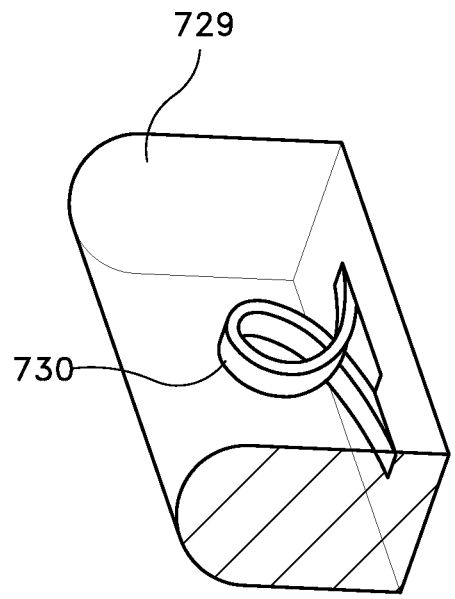
FIGS. 70-79 illustrate further embodiments of cushions according to the present invention.
Figure 71:
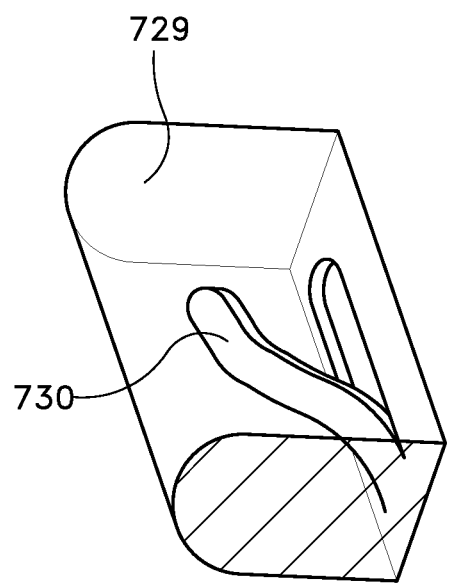

In FIGS. 70 and 71, the interior of the foam cushion 729 includes a spring element 730. The amount of cushion material over the spring element 730 can vary depending on the location of the cushion in relation to the patient's face. For example, in problem or sensitive seal areas, the cushion can be modified such that the spring element 730 is embedded more deeply into the cushion, whereby a seal with the problem or sensitive area is formed by the cushion alone, substantially without much, if any, contribution of spring element. One advantage is that the spring element 730 is fully embedded and invisible, so that there is a perceived simplicity, which can effect therapy compliance of the patient.

Figure 72:
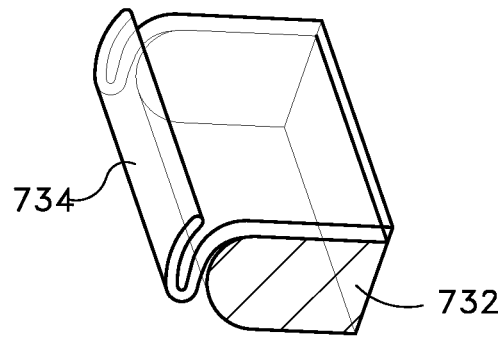
Figure 73:
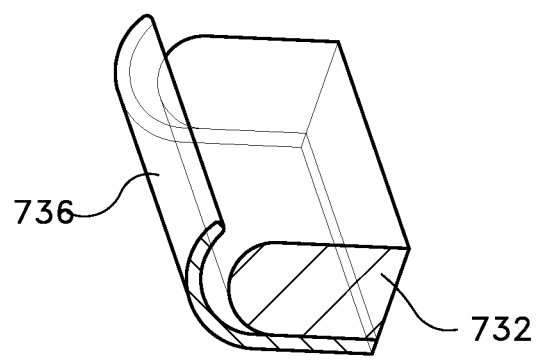

FIG. 72 includes a cushion 732 made of foam and a bellows 734, preferably made of silicone, provided to an inside surface of the cushion 732. The bellows 734 can readily conform to the patient's face. FIG. 73 is an arrangement which has a membrane 736 on the outside of the support 732.

Figure 74:
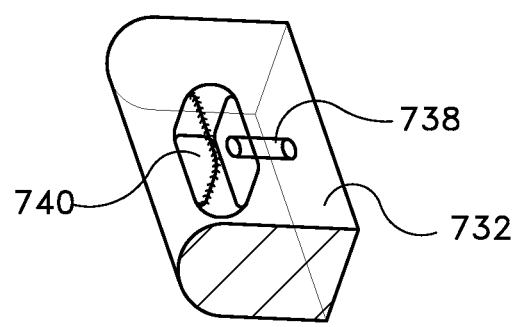

FIG. 74 is an arrangement in which a cushion 732 is provided with a channel 738 in communication with a chamber 740 arranged internally of the cushion 732. The channel 738 is in communication with a source of pressurized air or other medium, e.g., gel, such that the stiffness characteristics of the cushion can be changed.

Figure 75A:
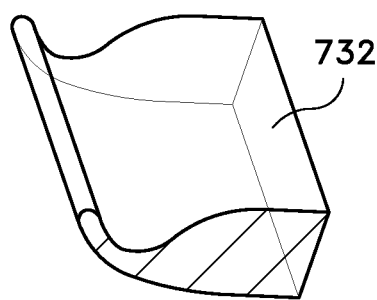
Figure 75B:
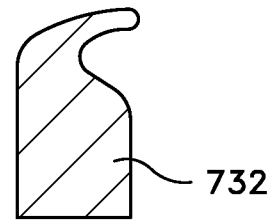
Figure 77:
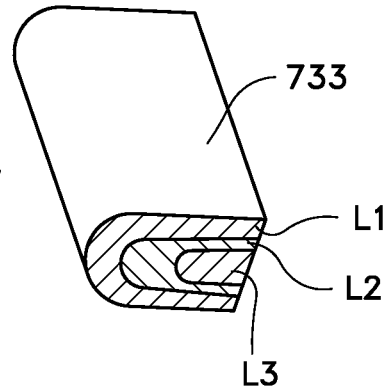
Figure 78:
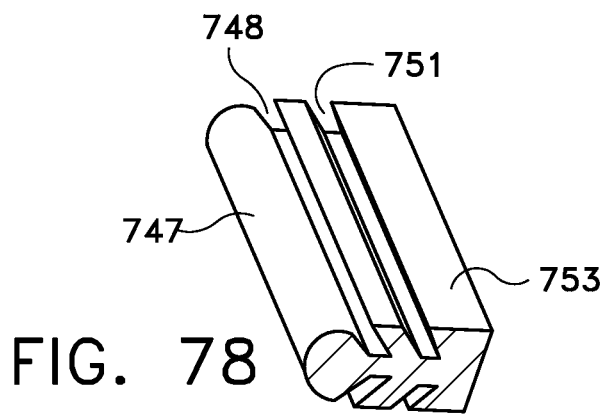
Figure 79:
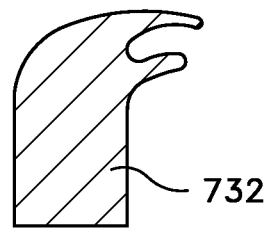

FIGS. 75A, 75B and 79 illustrate various cross sections which provide at least two spring rates as the cushion is compressed. In FIGS. 77 and 78, the cushion 732 includes at least three spring rates during compression. In FIG. 77, the cushion 732 includes three layers L1, L2 and L3, each of which has a different spring constant. FIG. 78 will have a first spring rate upon compressing head portion 747 into first groove 748, a second spring rate upon compressing central portion 749 into second groove 751, and a third spring rate upon engaging base portion 753.

Figure 76:
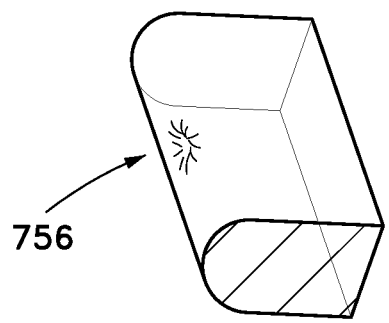

FIG. 76 illustrates a cushion 732 with a dimple 756 which may help maintain the seal, e.g., via suction, between the cushion and the patient's face.

An advantage of a foam insert as the flexible element is that foam is more compressible than silicone and thus a cushion assembly including a foam insert in accordance with the present invention achieves a better distribution of the load from the headgear.

An advantage of silicone as the flexible element is that silicone is easy to clean and possibly more biocompatible with patients. Note that each element, membrane, flexible element, and cushion flange, in the embodiments described above acts as a mechanical spring. The embodiments described above may be used in combination, for example, the flexible elements of the first and second embodiments may have multiple regions of differing stiffnesses (densities) or the individual segments of the flexible element of the second embodiment may have multiple regions of differing stiffnesses (densities). Many combinations of the disclosed membrane, flexible element and cushion flange can be used to achieve the desired comfort level.

The flexible element can be made from viscoelastic foam of a constant or multiple densities to provide the desirable effect. The flexible element can also be made from open or closed cell foam of constant or multiple densities. The flexible element may or may not be covered with a skin.

A mask assembly including a cushion assembly in accordance with an embodiment of the invention can use a four-strap headgear similar to that of the ULTRA MIRAGE™ mask system, manufactured by ResMed Limited.

A mask assembly including a cushion assembly in accordance with an embodiment of the invention can use headgear clips in accordance with U.S. Pat. No. 6,374,826, the contents of which are hereby included by cross reference.

An advantage of the cushion assemblies of the present invention to a mask system is increased comfort for the user. This is possible due to uniform distribution of the forces for people who need substantial strap tension to achieve a seal. The flexible element also helps maintain the shape of the membrane and an effective seal while the user moves during the night.

Other advantages of the cushion assemblies of the present invention include ease of manufacturing and reduced manufacturing costs. The cushion assemblies of the present invention are also less complicated than prior art cushions, for example, the ACLAIM cushion which is a three piece cushion requiring assembly before being affixed to the mask.

A further advantage of the present invention is that the flexible element results in less distortion of the membrane.

This allows the physician/clinician to fit the mask in less time with a more reliable seal.

A further advantage of the invention is that the provision of a flexible element under the membrane achieves a more stable seal. The flexible element provides a smaller variation in the leak rate between the face and the cushion due to reduced mask movement. This enhances the therapy provided by the bi-level machines.

To provide the correct force, the flexible element should have appropriate force displacement characteristics. This requirement is that the element should be soft enough to deflect initially to match the facial features but should not result in complete compression and discomfort to the user due to pressing of the rigid part of the cushion flange.

Figure 80:
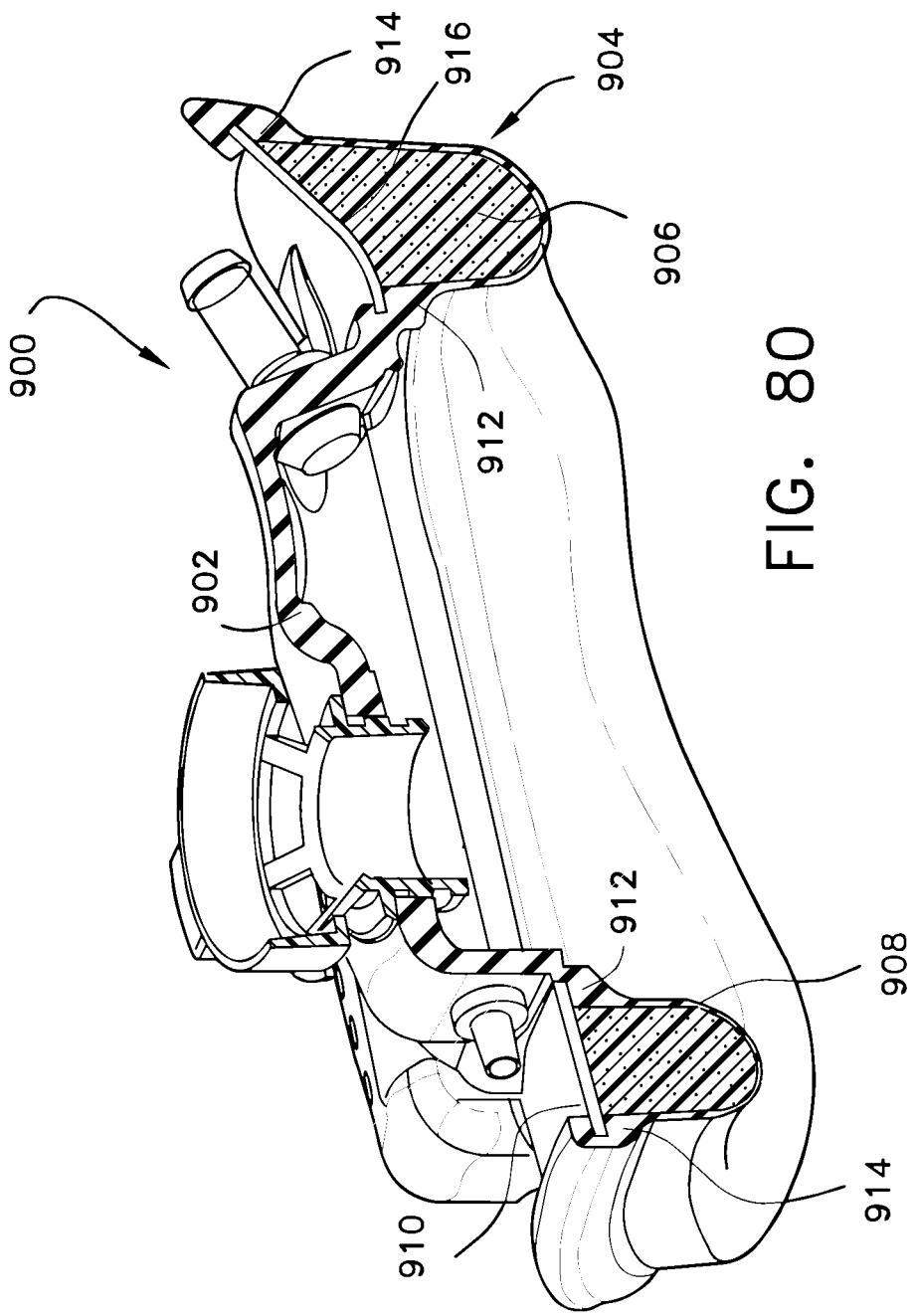
FIG. 80 illustrates a cross-sectional view of still another embodiment of the present invention.

In some of the examples described above, the cushion may be provided to the frame using adhesives. In another embodiment shown in FIG. 80, the cushion may be provided to the frame using a mechanical fastener. In the example of FIG. 80, a mask assembly 900 includes a body portion 902 and a cushion 904 provided to the body portion 902. The cushion 904 may include a neoprene cushion 906 covered with a continuous silicon membrane 908, for example. A flexible portion 910 may be provided along the perimeter of the body portion 902, for reasons described above. The body portion 902 and the membrane 908 may be formed of a single piece in this example. The membrane 908 includes an inner perimeter shoulder 912 and an outer perimeter shoulder 914 to engage a surface 916 of the flexible frame 910. The outer perimeter shoulder 914 may wrap around the edge of the flexible frame 910. Alternatively, the outer perimeter shoulder may be said to include a groove to accommodate the outer edge of the flexible frame 910. Similarly, the inner peripheral shoulder may include a groove to accommodate the inner perimeter of the flexible frame 910. Stated differently, the member 908 "snaps on" to the edges of the frame 910.

Snapping the edge of the cushion against the frame removes the necessity to glue the neoprene cushion to the frame, although gluing may be used between the neoprene cushion and the silicone membrane. This arrangement provides superior integrity of the assembly providing a more reliable connection between all the parts and also removes any problems associated with chemical compatibility between the neoprene cushion and the nylon frame necessary for adhesion.

The mask assembly is robust enough to withstand forces exerted by rigorous use, thus resulting in greater reliability and patient security. The membrane 908 provides a sealed air path which reduces air leak.

Figure 81:
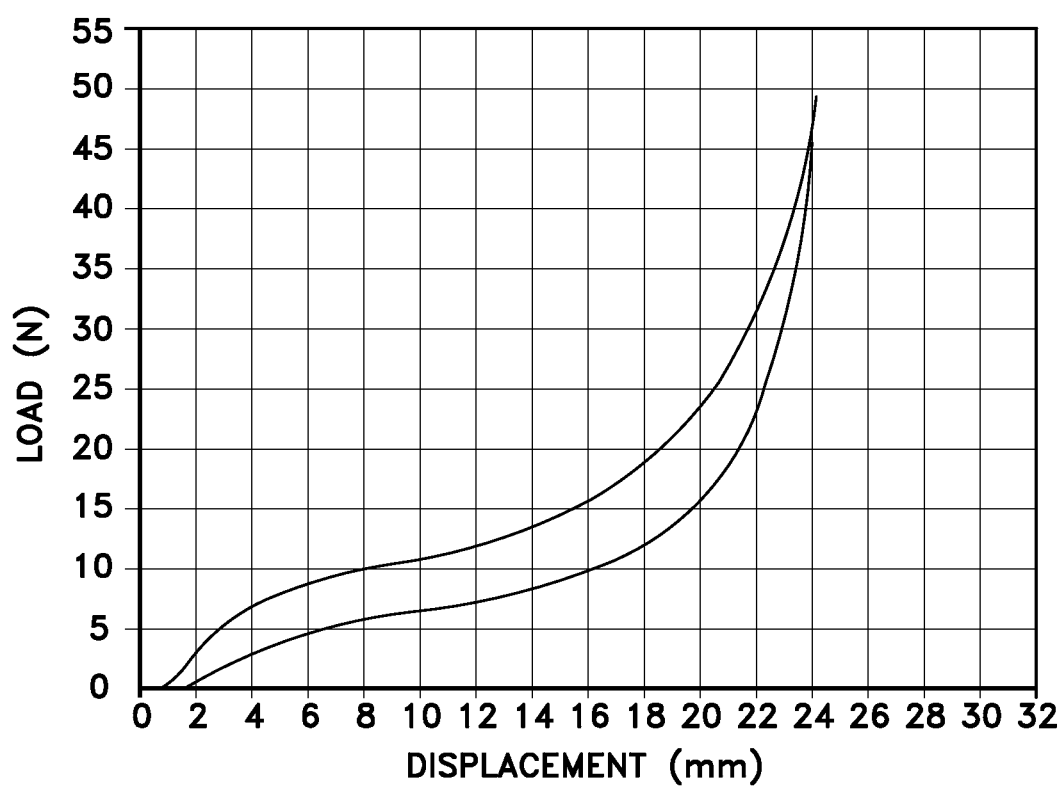
FIG. 81 is a relaxation curve for a foam suitable for use as a flexible element according to all embodiments of the present invention.

A relaxation curve for a foam suitable for use in the flexible element according to the invention is shown in FIG. 81.

The following table lists exemplary properties of a foam suitable for use in the flexible element according to all embodiments of the present invention:

| Property | Value |
|---|---|
| Density | 0.1752 (g/cm³) |
| CLD @ 25% | 1.054 (N/cm²) |
| CLD @ 65% | 3.375 (N/cm²) |
| Sag Factor | 3.20 |
| IHF | 4.36 |
| Recovery % | 57 |

The definitions which are found below were obtained from publicly available reference materials, and may not use the same units of measure as described above in relation to the above table of exemplary properties.

Density is the weight per unit volume of the foam and below expressed in pounds per cubic foot (pcf.), although the above density is measured in g/cm³. The general range of polyether flexible urethane foams is 1 to 4 pcf. This density is not a measure of firmness as is the case with latex rubber foams. For a given load bearing requirement, the higher density foam generally gives better quality and performance.

Compression load deflection (CLD) is also a measure of load bearing and is generally expressed in pounds per square inch (psi) at a given percentage deflection. The entire sample is compressed in this test and the values are independent of foam thickness, providing thickness does not exceed length and width measurements. CLD is used to specify firmness of certain types of specialty foams and some semi-flexible foams. Values also are used in determining changes in load bearing under various humid aging or heat aging conditions.

Indentation load deflection (ILD) is one measure of load bearing and is expressed in pounds load per 50 square inches at a given percentage deflection of the foam. To obtain the value, a 50 square inch circular plate (a) is pushed into the foam top surface, stopping at a given deflection and reading a load or a scale. For example, a 25 percent ILD of 30 means that it takes 30 pounds load to compress a 4 inch thick piece of foam to a 3 inch thickness. The higher the load, the firmer the foam. In this test, the foam sample size is larger than the circular plate, generally 15 by 15 inches for slab foams.

Some specifications define ILD with other plate configurations and dimensions. ILD is sometimes referred to as RMA (Rubber Manufacturers Association) from the same measurement used for latex foams. Suggested practice for specifying flexible foam is: USU (Urethane Slab Uncored); USC (Urethane Slab Cored); UMU (Urethane Molded Uncored); UMC (Urethane Molded Cored). Digits following this code specify the 25 percent ILD, such as USU—30 refers to uncored slab with a 25 percent ILD of 30. Original thickness of the foam must be specified as values are affected by the original foam thickness. (See BASF Wyandotte Technical Advisory, "Effect of Foam Thickness on ILD".)

Sag factor is the ratio of 65 percent ILD to 25 percent ILD and gives an indication of cushioning quality. A high value indicates resistance to bottoming out. Foams with low sag factors will often "bottom out" and give inferior performance. Other terms for this number are SAG factor and modulus.

Initial hardness factor (IHF) is the ratio of 25 percent ILD to the 5 percent ILD. This factor defines the surface feel. Supple or soft surface foams will have a high value while boardy or stiff surface foams will have a low value. Another term for initial hardness factor is comfort factor.

In measuring ILD, values are normally taken at 25 percent deflection, 65 percent deflection and again at 25 percent reflection as the load is removed. The value of this 25 percent deflection on release of the load divided by the original 25 percent deflection is the recovery and expressed as a percentage. High recovery values are desired for cushioning applications while low recovery would be desired for shock absorbing applications. Low recovery foams are sometimes referred to as "dead."

Indentation residual gauge load (IRGL) is another measure of load bearing and is expressed as inches at a given loading. The same 50 square inch circular plate is used as for ILD but now the plate is weighted with a given load. Normal loadings are 25, 50, or 75 pounds. The IRGL value is in inches. The original thickness of the foam must be known to make the values meaningful. This measure is frequently used in automotive foam specifications. There is no ready correlation between ILD and IRGL values.

Guide factor is the ratio of 25 percent ILD to density. This term is useful in determining the relative firmness of foams with different density. The closer the densities, the better the comparison. When densities are different, the foam with the highest guide factor has the cost advantage, but not necessarily the performance advantage. Another term for guide factor is normalized ILD.

Indentation modulus (IM) is the load required to produce an indentation of 1 percent between the limits of 20 percent ILD and 40 percent ILD. The slope of this line depends on resistance of foam cell walls to buckling.

Resilience is a measure of elasticity or springiness of foam. In this test, a steel ball is dropped on the foam and the rebound is expressed as percent resilience. As with recovery, desirable values are dependent on application. With very soft foam, resilience can be misleading because the foam bottoms out under the load of the ball. This gives low resilience values even though the foam is very "lively" or elastic. Ball rebound is another term for this property.

Tensile strength is a measure of the amount of stress required to break the foam as it is pulled apart and is expresses in pounds per square inch (psi). Tensile strength can be used as a control check for quality. One common test is the determination of change of tensile strength after heat aging.

Elongation is generally measured at the same time as tensile strength is determined. It is a measurement of the extent to which the foam can be stretched before it breaks and is expressed as a percentage of original length.

Tear strength is a measure of the force required to continue a tear in a foam after a split or break has been started and is expressed in pounds per lineal inch (pli or more commonly pi). This property is important in determining suitability of foam in application where the material is sewed, stapled or "hog-ringed."

Compression set is a measure of the deformation of a foam after it has been held compressed under controlled time and temperature conditions. The standard conditions are 22 hours at 158° F. In the test, foam is compressed to a thickness given as a percentage of its original thickness. Compression set is most commonly expressed as a percentage of original compression.

Fatigue is a measurement of the loss in load bearing under simulated service conditions and is generally expressed as a percentage load loss. The two most common fatigue tests are static fatigue and roller shear fatigue.

In a static fatigue test, the foam is compressed to 25 percent of its original thickness for 17 hours at room temperature. ILD losses are calculated as percentages of original values.

In the roller shear fatigue test, a roller, longer than the foam width, is rolled back and forth across the foam. The roller is mounted in an off-set position to impart a shearing action. Tests vary in use of constant deflection settings or constant roller weights. Losses are calculated in ILD or IRGL as specified in the test method.

Air flow is a measurement of the porosity or openness of foam expressed in cubic feet of air per minute (cfm). Air can be pulled through a foam by vacuum as specified in the ASTM procedure or blown through using apparatus as described in the BASF Wyandotte Technical Advisories, "BWC Portable Air Flow Apparatus" and "BWC Portable Air Flow Apparatus-Improved Model".

There are many other foam properties and test procedures. Many of these have been developed with specific end uses in mind. Further definition of terms and description of test methods can be found in ASTM Standard Methods D-1564 and D-2406 in specific foam specification sheets.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the present invention.

The invention claimed is:

1. A patient interface for sealed delivery of a flow of air at a continuously positive pressure with respect to ambient air pressure to an entrance to a patient's airways including at least entrance of a patient's nares, the patient interface comprising:
    a shell with a central opening configured to receive the pressurized flow of air;
    a foam cushion comprising:
        an outwardly facing surface configured to face the patient's face in use;
        an inwardly facing surface opposite the outwardly facing surface; and
        an interior surface extending from the inwardly facing surface to the outwardly facing surface; and
    an elastomeric support portion that is attached to the shell, supports the foam cushion, and forms at least part of a chamber together with the shell and the foam cushion, the elastomeric support portion comprising:
        a side wall that forms a continuous perimeter around the chamber; and
        a resiliently flexible lip that supports the foam cushion and extends from the side wall toward an interior of the chamber, the resiliently flexible lip comprising an outer perimeter that is anchored to the side wall and an unsupported inner perimeter,
    wherein the inwardly facing surface of the foam cushion is in contact with the resiliently flexible lip and extends inwardly beyond the resiliently flexible lip so that the foam cushion overhangs the inner perimeter of the resiliently flexible lip, and
    wherein the shell is more rigid than the elastomeric support portion.

2. The patient interface of claim 1, wherein a distance between the inner and outer perimeters of the resiliently flexible lip varies in size in different regions of the patient interface.

3. The patient interface of claim 1, wherein an amount by which the foam cushion overhangs the resiliently flexible lip varies in different regions of the patient interface.

4. The patient interface of claim 1, wherein the side wall and the resiliently flexible lip of the elastomeric support portion are unitarily formed as a single unit.

5. The patient interface of claim 1, wherein the side wall of the elastomeric support portion comprises a flange, and wherein the flange is connected to the shell.

6. The patient interface of claim 5, wherein the flange comprises a channel that receives an edge of the shell.

7. The patient interface of claim 1, wherein the patient interface is in the form of a full face mask.

8. The patient interface of claim 1, wherein the patient interface is in the form of a nasal mask.

9. The patient interface of claim 1, wherein a distance between the inner and outer perimeters of the resiliently flexible lip varies in size in different regions of the patient interface,
  wherein an amount by which the foam cushion overhangs the resiliently flexible lip varies in different regions of the patient interface,
  wherein the side wall and the resiliently flexible lip of the elastomeric support portion are unitarily formed as a single unit,
  wherein the side wall of the elastomeric support portion comprises a flange,
  wherein the flange is connected to the shell, and
  wherein the patient interface is in the form of a full face mask or a nasal mask.

10. A patient interface assembly comprising:
  the patient interface of claim 1;
  headgear configured to support the patient interface on the patient's head; and
  an air delivery tube configured to deliver the pressurized flow of air to the patient interface.

11. The patient interface assembly of claim 10, further comprising a connector configured to attach the air delivery tube to the shell at the central opening of the shell.

12. The patient interface of claim 1, wherein the foam cushion is covered with a layer that is configured to contact the patient's skin in use.

13. A patient interface for sealed delivery of a flow of air at a continuously positive pressure with respect to ambient air pressure to an entrance to a patient's airways including at least entrance of a patient's nares, the patient interface comprising:
  a shell with a central opening configured to receive the pressurized flow of air;
  a foam cushion comprising:
    an outwardly facing surface configured to face the patient's face in use;
    an inwardly facing surface opposite the outwardly facing surface; and
    an interior surface extending from the inwardly facing surface to the outwardly facing surface; and
  an elastomeric side wall with an inwardly extending lip at a first end and a connection interface at a second end,
  wherein the foam cushion is supported by the inwardly extending lip,
  wherein the inwardly facing surface of the foam cushion is in contact with the inwardly extending lip and extends inwardly beyond the inwardly extending lip so that the foam cushion overhangs the inwardly extending lip,
  wherein the elastomeric side wall is attached to an edge of the shell at the connection interface,
  wherein the shell, the foam cushion, and the elastomeric side wall together form a plenum chamber,
  wherein the shell is more rigid than the elastomeric side wall.

14. The patient interface of claim 13, wherein the inwardly extending lip extends a distance into the plenum chamber, and wherein the distance varies in different regions of the patient interface.

15. The patient interface of claim 13, wherein an amount by which the foam cushion overhangs the inwardly extending lip varies in different regions of the patient interface.

16. The patient interface of claim 13, wherein the connection interface of the elastomeric side wall comprises a flange, and wherein the flange is connected to the shell.

17. The patient interface of claim 16, wherein the flange comprises a channel that receives the edge of the shell.

18. The patient interface of claim 13, wherein the patient interface is in the form of a full face mask.

19. The patient interface of claim 13, wherein the patient interface is in the form of a nasal mask.

20. The patient interface of claim 13, wherein the inwardly extending lip extends a distance into the plenum chamber, and wherein the distance varies in different regions of the patient interface,
  wherein an amount by which the foam cushion overhangs the inwardly extending lip varies in different regions of the patient interface,
  wherein the connection interface of the elastomeric side wall comprises a flange,
  wherein the flange is connected to the shell, and
  wherein the patient interface is in the form of a full face mask or a nasal mask.

21. A patient interface assembly comprising:
  the patient interface of claim 13;
  headgear configured to support the patient interface on the patient's head; and
  an air delivery tube configured to deliver the pressurized flow of air to the patient interface.

22. The patient interface assembly of claim 21, further comprising a connector configured to attach the air delivery tube to the shell at the central opening of the shell.

23. The patient interface of claim 13, wherein the foam cushion is covered with a layer that is configured to contact the patient's skin in use.

* * * * *